(12) United States Patent
Finn et al.

(10) Patent No.: US 7,652,036 B2
(45) Date of Patent: Jan. 26, 2010

(54) CARBAMIC ACID COMPOUNDS COMPRISING A BICYCLIC HETEROARYL GROUP AS HDAC INHIBITORS

(75) Inventors: Paul W. Finn, Abingdon (GB); Ivars Kalvinsh, Riga (LV); Einars Loza, Riga (LV); Victor Andrianov, Riga (LV); Olga Habarova, Riga (LV); Daina Lolya, Riga (LV); Irina Piskunova, Riga (LV)

(73) Assignee: Topotarget UK Limited, Oxford (GB)

( * ) Notice: Subject to any disclaimer, the term of this patent is extended or adjusted under 35 U.S.C. 154(b) by 455 days.

(21) Appl. No.: 10/546,153

(22) PCT Filed: Feb. 25, 2004

(86) PCT No.: PCT/GB2004/000765

§ 371 (c)(1),
(2), (4) Date: Aug. 22, 2005

(87) PCT Pub. No.: WO2004/076386

PCT Pub. Date: Sep. 10, 2004

(65) Prior Publication Data

US 2006/0079528 A1 Apr. 13, 2006

Related U.S. Application Data

(60) Provisional application No. 60/449,394, filed on Feb. 25, 2003.

(51) Int. Cl.
C07D 215/38 (2006.01)
A61K 31/48 (2006.01)

(52) U.S. Cl. .................. 514/311; 514/312; 546/159; 546/163

(58) Field of Classification Search ............ 546/159, 546/163; 514/311, 312
See application file for complete search history.

(56) References Cited

U.S. PATENT DOCUMENTS

| | | | |
|---|---|---|---|
| 3,912,748 A | 10/1975 | Evans et al. | |
| 4,285,962 A | 8/1981 | Franzone | |
| 4,769,461 A | 9/1988 | Musser et al. | |
| 5,804,593 A | 9/1998 | Warpehoski et al. | |
| 5,834,249 A | 11/1998 | Furukawa et al. | |
| 6,172,057 B1 | 1/2001 | Venkatesan et al. | |
| 6,235,753 B1 * | 5/2001 | Bailey et al. | 514/311 |
| 6,420,427 B1 | 7/2002 | Takahashi et al. | |
| 6,444,704 B1 * | 9/2002 | Venkatesan et al. | 514/575 |

FOREIGN PATENT DOCUMENTS

| | | |
|---|---|---|
| DE | 1974-2404413 | 8/1974 |
| EP | 0 342 682 | 11/1989 |
| EP | 0 570 594 | 11/1993 |
| EP | 0 737 671 | 10/1996 |
| EP | 0 827 742 | 3/1998 |
| EP | 0 887 348 | 12/1998 |
| FR | 2338041 | 8/1977 |
| JP | 10114681 | 5/1998 |
| WO | WO 96/11917 | 4/1996 |
| WO | WO 97/43249 | 11/1997 |
| WO | WO 99/67201 | 12/1999 |
| WO | WO 00/05218 | 2/2000 |
| WO | WO 00/03413 | 6/2000 |
| WO | WO 00/69827 | 11/2000 |
| WO | WO 01/38322 | 5/2001 |
| WO | WO 01/70675 | 9/2001 |
| WO | WO 02/22577 | 3/2002 |
| WO | WO 02/26696 | 4/2002 |
| WO | WO 02/26703 | 4/2002 |
| WO | WO 02/30879 | 4/2002 |
| WO | WO 02/076941 | 10/2002 |
| WO | WO 02/090534 | 11/2002 |
| WO | WO 03/082288 | 10/2003 |

OTHER PUBLICATIONS

Bailey, Bioorg & Med Chem Lett, vol. 9(21), pp. 3165-3170, 1999.*
McLaughlin, Current Drug targets Inflamm Allergy, vol. 3(2), pp. 213-219, Jun. 2004.*
Andrews et al., 2000, "Anti-malarial effect of histone deacetylation inhibitors and mammalian tumour cytodifferentiating agents," *Int. J. Parasitol.*, vol. 30, No. 6, pp. 761-768.
Babichev et al., 1968, "Benzo-2-thiazolyl)alkane(arene)carboxylic acids and their derivatives. VII. Hydrazides, hydroxamic acids, nitriles and thioamides from (benzo-2-thiazolyl)alkanecarboxylic acids," *Ukrainskii Khimicheskii Zhurnal*, vol. 34, No. 9, pp. 933-936 (with English abstract).

(Continued)

*Primary Examiner*—D. Margaret Seaman
(74) *Attorney, Agent, or Firm*—Nixon & Vanderhye P.C.

(57) ABSTRACT

This invention pertains to certain carbamic acid compounds of the following formula, which inhibit HDAC (histone deacetylase) activity wherein: A is independently an unsubstituted or substituted bicyclic $C_{9-10}$heteroaryl group (e.g., quinolinyl; quinoxalinyl; benzoxazolyl; benzothiazolyl); Q is an acid leader group, and is independently an unsubstituted or substituted, saturated or unsaturated $C_{1-7}$alkylene group having a backbone length of 4 or less; with the proviso that if A is unsubstituted benzothiazol-2-yl, then Q is an unsaturated group; and with the proviso that if A is unsubstituted quinolin-6-yl, then Q is unsubstituted at the α-position; and with the proviso that A is not benzimidazol-2-yl; and pharmaceutically acceptable salts, solvates, amides, esters, ethers, chemically protected forms, and prodrugs thereof. The present invention also pertains to pharmaceutical compositions comprising such compounds, and the use of such compounds and compositions, both in vitro and in vivo, to inhibit HDAC, and in the treatment of conditions mediated by HDAC, cancer, proliferative conditions, psoriasis, etc.

38 Claims, No Drawings

OTHER PUBLICATIONS

Badaev, F.A. et al., 1973 "Antiviral activity of synthetic compounds", *Veterinariya*, vol. 6, pp. 44-46 (with English abstract).

Barbier, C. et al., 2000, Preparation of Lavendamycin Analogues, *Heterocycles*, vol. 5, pp. 37-48.

Bernhard, D. et al., 1999, "Apoptosis induced by the histone deacetylase inhibitor sodium butyrate in human leukemic lymphoblasts," *FASEB J.*, vol. 13, No. 14, pp. 1991-2001.

Bernstein et al., 2000, "Genomewide studies of histone deacetylase function in yeast," *Proc. Natl. Acad. Sci. USA*, vol. 97, No. 25, pp. 13708-13713.

Brehm, A., et al., 1998, "Retinoblastoma protein recruits histone deacetylase to repress transcription," *Nature*, 1998, vol. 391, pp. 597-601.

Buchi, von J. et al., 1956, "Synthese und pharmakologische wirkung einiger thiosemicarbazone von 8-hydroxychinolin-derivaten," *Helv. Chim. Acta*, vol. 39, pp. 1676-1683 (with English language summary).

Chang et al., 2000, "Activation of the BRLF1 promotor and lytic cycle of Epstein-Barr virus by histone acetylation," *Nucleic Acids Res.*, vol. 28, No. 20, pp. 3918-3925.

Conte, M., et al., 1967, "Synthèse et propriétés physico-chemiques de bases de Schiff en série benzothiazolique", *Bull. Soc. Chim. Fr.*, pp. 2834-2841 (with English abstract—CA 68:78190k).

Dangond et al., 1998, Differential Display Cloning of a Novel Human Histone Deacetylase (HDAC3) cDNA from PHA-Activated Immune Cells, *Biochem. Biophys. Res. Commun.*, vol. 242, No. 3, pp. 648-652.

David, G., et al., 1998, "Histone deaetylase associated with mSin3A mediates repression by the acute promyelocytic leukemia-associated PLZF protein," *Oncogene*, vol. 16(19), pp. 2549-2556.

Davie, J.R., 1998, "Covalent modifications of histones: expression from chromatic templates," *Curr. Opin. Genet. Dev.*, vol. 8, pp. 173-178.

Desai, D., et al., 1999, "Chemopreventive efficacy of suberanilohydroxamic acid (SAHA), a cytodifferentiating agent, against tobacco-specific nitrosamine 4-(methylnitros-amino)-1-(3-pyridyl)-1-butanone (NNK)-induced lung tumorigenesis in female A/J mice," *Proceedings of the American Association for Cancer Research*, Prevention/Basic Science and Clinical Studies 4, vol. 40, p. 362, Abstract No. 2396.

Desmarets, C. et al., 2001, "Nickel-catalysed sequential amination of aryl- and heteroaryl di- and trichlorides," *Tetrahedron*, vol. 57, pp. 7657-7664.

Emiliani, S., et al., 1998, "Characterization of a human RPD3 ortholog, HDAC3," *Proc. Natl. Acad. Sci. USA*, vol. 95, p. 2795-2800.

Finnin et al., 1999, "Structures of a histone deacetylase homologue bound to the TSA and SAHA inhibitors," *Nature*, vol. 401, pp. 188-193.

Franke, U. et al., "Synthese von 3-(2-indolyl)-acrylsaurederivaten," *Arch. Pharm. (Weinheim)*, vol. 310, pp. 975-979 (with English abstract—CA 88:105054r).

Frank, W.C. et al., 1978, "Palladium-catalyzed vinylic substitution reactions with heterocyclic bromides", *J. Org. Chem.*, vol. 43, pp. 2947-2949.

Gall, von R. et al., 1955, "Über einige derivate heterocyclischer carbonsäuren IV," *Helv. Chim. Acta.*, vol. 38, pp. 1421-1423 (with English language summary).

Gordon, M. et al., 1964, "The swamping catalyst effect. VI. The Halogenation of isoquinoline and quinoline", *J. Org. Chem.*, vol. 39, pp. 329-332.

Grozinger et al., 1999, "Three proteins define a class of human histone deacetylases related to yeast Hdalp," *Proc. Natl. Acad. Sci. USA*, vol. 96, pp. 4868-4873.

Günes, H.S. et al., 1992, "Synthesis of some hydroxamic acid derivatives of benzimidazole and their antibacterial and antifungal activities," *Arzneimittel-Forschung*, vol. 42, No. 8, pp. 1045-1048.

Hartwig, J.F., et al., 1999, "Room-Temperature Palladium-Catalyzed Amination of Aryl Bromides and Chlorides and Extended Scope of Aromatic C-N Bond Formation with a Commercial Ligand," *J. Org. Chem.*, vol. 64, pp. 5575-5580.

Hoshikawa, Y., et al., 1994, "Trichostatin A Induces Morphological Changes and Gelsolin Expression by Inhibiting Histone Deacetylase in Human Carcinoma Cell Lines," *Exp. Cell. Res.*, vol. 214(1), pp. 189-197.

Howe, L., et al., 1999, "Histone Acetyltransferase Complexes and Their Link to Transcription," *Crit. Rev. Eukaryot. Gene Expr.*, vol. 9(3-4), pp. 231-243.

Iavarone et al., 1999, "E2F and Histone Deacetylase Mediate Transforming Growth Factor β Repression of *cdc25A* during Keratinocyte Cell Cycle Arrest," *Mol. Cell Biol.*, vol. 19, No. 1, pp. 916-922.

Iwao, M. et al., 1978, "The facile synthesis of some N-heteroarylacetic esters", *J. Heteroc. Chem.*, vol. 15, pp. 1425-1430.

Kao et al., 2000, "Isolation of a novel histone deacetylase reveals that class I and class II deacetylases promote SMRT-mediated repression," *Genes & Dev.*, vol. 14, p. 55-66.

Kepez, M. 1989, "Oxidation of 2,3-dimethyl-quinoxaline and 2,4-dimethyl-quinazoline with selenium dioxide," *Monatsh. Chem.*, vol. 120, pp. 127-130 (with English abstract—CA 111:134088d).

Kijima et al., 1993, "Trapoxin, an Antitumor Cyclic Tetrapeptide, Is an Irreversible Inhibitor of Mammalian Histone Deacetylase*," *J. Biol. Chem.*, vol. 268, pp. 22429-22435.

Kim et al., 1999, "Oxamflatin is a novel antitumor compound that inhibits mammalian histone deacetylase," *Oncogene*, vol. 18(15), pp. 2461-2470.

Kim, M.S., et al., 2001 "Histone deacetylases induce angiogenesis by negative regulation of tumour suppressor genes," *Nature Medicine*, vol. 7, No. 4, pp. 437-443.

Kimura et al., 1994, "Dual Modes of Action of Platelet-Derived Growth Factor and Its Inhibition by Trichostatin-A for DNA Synthesis in Primary Cultured Smooth Muscle Cells of Rat Aorta," *Biol. Pharm. Bull.*, vol. 17, No. 3, pp. 399-402.

Kitamura, K., et al., 2000, "Histone deacetylase inhibitor but not arsenic trioxide differentiates acute promyelocytic leukaemia cells with t(11;17) in combination with all-trans retinoic acid," *Br. J. Haematol.*, vol. 108(4), pp. 696-702.

Kloc, K. et al., 1984, "A novel approach to functionalization of azines. Oxiranyl and thiiranyl derivatives of pyridine, quinoline and isoquinoline," *Heterocycles*, vol. 22, No. 11, pp. 2517-2522.

Kolar, P. et al., 1991, "Heterocycles from amino acids. A novel synthetic approach for imidazo[1,5-α]pyridines and imidazo[1,5-α]quinolines," *J. Heteroc. Chem.*, vol. 28, pp. 1715-1720.

Kouzarides, T., 1999, "Histone acetylases and deacetylases in cell proliferation," *Curr. Opin. Genet. Dev.*, vol. 9, No. 1, pp. 40-48.

Kuusisto et al., 2001, "Ubiquitin-Binding Protein p62 Expression is Induced during Apoptosis and Proteasomal Inhibition in Neuronal Cells," *Biochem. Biophys. Res. Commun.*, vol. 280, No. 1, pp. 223-228.

Kwon et al., 1998, "Depudecin induces morphological reversion of transformed fibroblasts via the inhibition of histone deacetylase," *Proc. Natl. Acad. Sci. USA*, vol. 95, pp. 3356-3361.

Laherty, C.D., et al., 1997, "Histone Deacetylases Associated with the mSin3 Corepressor Mediate Mad Transcriptional Repression," *Cell*, vol. 89(3), pp. 349-356.

Laske, R. et al., 1989, "Investigations on the antiproliferative effects of amino acid antagonists targeting for aminoacyl-tRNA synthetases", *Arch. Pharm. (Weinheim)*, vol. 322, pp. 857-862.

Lea and Tulsyan, 1995, "Discordant Effects of Butyrate Analogues on Erythroleukemia Cell Proliferation, Differentiation and Histone Deacetylase," *Anticancer Res.*, vol. 15, pp. 879-883.

Lea et al., 1999, "Increased acetylation of histones induced by diallyl disulfide and structurally related molecules," *Int. J. Oncol.*, vol. 2, pp. 347-352.

Lin, R.J., et al., 1998, "Role of the histone deacetylase complex in acute promyelocytic leukaemia," *Nature*, vol. 391(6669), pp. 811-814.

Mathes, S., 1956, "Über einige substituierte aldehyde der chinolin- und pyridinreihe," *Chem. Ber.*, vol. 89, pp. 758-761 (with English language summary).

McCaffrey et al., 1997, "Induction of γ-Globin by Histone Deacetylase Inhibitors," *Blood*, vol. 90, No. 5, pp. 2075-2083.

Mielnicki, L.M., et al., 1999, "Epigenetic Regulation of Gelsolin Expression in Human Breast Cancer Cells," *Exp. Cell. Res.*, vol. 249(1), pp. 161-176.

Musser et al., "N-[arylmethoxy)phenyl] carboxylic acids, hydroxamic acids, tetrazoles, and sulfonyl carboxamides. Potent orally active leukotriene $D_4$ antagonists of novel structure," 1990, *J. Med. Chem.*, vol. 33, pp. 240-245.

Nakajima et al., 1998, "FR901228, a Potent Antitumor Antibiotic, Is a Novel Histone Deacetylase Inhibitor," *Exp. Cell Res.*, vol. 241, pp. 126-133.

Ng, H.H. and Bird, A., 2000, "Histone deacetylases: silencers for hire," *Trends Biochem. Sci.*, vol. 25(3), pp. 121-126.

Niki et al., 1999, "A Histone Deacetylase Inhibitor, Trichostatin A, Suppresses Myofibroblastic Differentiation of Rat Hepatic Stellate Cells in Primary Culture," *Hepatology*, vol. 29, No. 3, pp. 858-867.

Onishi et al., 1996, "Antibacterial Agents That Inhibit Lipid A Biosynthesis," *Science*, vol. 274, pp. 980-982. OR 939-940????

Parrish et al., 2001, "Use of polymer-supported dialkylphosphinobiphenyl ligands for palladium-catalyzed amination and Suzuki reactions,", *J. Org. Chem.*, vol. 66, pp. 3820-3827.

Pazin, M.J., et al., 1997, "What's up and down with histone deacetylation and transcription?," *Cell*, vol. 89, No. 3, pp. 325-328.

Phillips, A.P., 1948, "Cinchoninaldehyde and reactive methylene compounds. IV," *J. Am. Chem. Soc.*, vol. 70, pp. 452-454.

Richon et al, 1996, "Second generation hybrid polar compounds are potent inducers of transformed cell differentiation," *Proc. Natl. Acad. Sci. USA*, vol. 93, pp. 5705-5708.

Richon et al., 1998, "A class of hybrid poler inducers of transformed cell differentiation inhibits histone deacetylases," *Proc. Natl. Acad. Sci. USA*, vol. 95, pp. 3003-3007.

Ried et al., 1956, "Uber heterocyclisch substituierte Aminosaeuren, V. Mitteil: Synthesen einiger β-heterocyclisch substituierter Acryl- and β-Aminosaeuren," *Chem. Ber.*, vol. 89, No. 11, pp. 2578-2583.

Saito et al., 1999, "A synthetic inhibitor of histone deacetylase, MS-27-275, with marked in vivo antitumor activity against human tumors," *Proc. Natl. Acad. Sci. USA*, vol. 96, pp. 4592-4597.

Saunders, N. et al, 1999 "Histone deacetylase inhibitors as potential anti-skin cancer agents," *Cancer Res.*, vol. 59, No. 2 pp. 399-404.

Sonoda, H. et al., 1996, "Oxamflatin: a novel compound which reverses malignant phenotype to normal one via induction of JunD," *Oncogene*, vol. 13, pp. 143-149.

Spencer, V.A. and Davie, J.R., 1999, "Role of covalent modifications of histones in regulating gene expression," *Gene*, vol. 240(1), pp. 1-12.

Strakov et al., 1972, "Hydrolytic cleavage of 3,3,6-trimethyl-2,3,4,5-tetrahydro-1H-dibenzo(b,e)-1,4-diazepin-5-one," *Latvijas PSR Zinatnu Akademijas Vestis, Kimijas Serija*, vol. 3, pp. 355-359 (with English Abstract—CA 77:75195r).

Suzuki et al., 1999, "Synthesis and histone deactylase inhibitory activity of new benzamide derivatives," *J. Med. Chem.*, vol. 42, pp. 3001-3003.

Takahashi, I., et al, 1996, "Selective inhibition of IL-2 gene expression by trichostatin A, a potent inhibitor of mammalian histone deacetylase," *J. Antibiot.* (Tokyo), vol. 49, No. 5, pp. 453-457.

Taunton, J., et al., 1996, "A mammalian histone deacetylase related to the yeast transcriptional regulator Rpd3p," *Science*, vol. 272, pp. 408-411.

Tsuji et al., 1976, "A New Antifungal Antibiotic, Trichostatin*," *J. Antibiot.* (Tokyo), vol. 29, No. 1, pp. 1-6.

Ueda, H., et al., 1994, "FR901228, a novel antitumor bicyclic depsipeptide produced by *Chromobacterium violaceum* No. 968," *J. Antibiot.* (Tokyo), vol. 47(3), pp. 315-323.

Van den Wyngaert et al., "Cloning and characterization of human histone deacetylase 8," 2000, *FEBS*, vol. 478, pp. 77-83.

Vigushin et al., 2001, "Trichostatin A Is a Histone Deacetylase Inhibitor with Potent Antitumor Activity against Breast Cancer in vivo[1]," *Clin. Cancer Res.*, vol. 7, No. 4, pp. 971-976.

Wada et al., 1973, "A new nonsteroidal anti-inflammatory agent 2 substituted 5 benzothiazoleacetic-acid or 6 benzothiazole acetic-acid and their derivatives," *Journal of Medicinal Chemistry*, vol. 8, pp. 930-934.

Warrell et al., 1998, "Therapeutic Targeting of Transcription in Acute Promyelocytic Leukemia by Use of an Inhibitor of Histone Deacetylase," *J. Natl. Cancer Inst.*, vol. 90, pp. 1621-1625.

Weygand, F., et al., 1962, Eine neue methode zur umwandlung von α-aminosären in α-ketosäuren*Justus Liebigs Ann. Chem.*, vol. 658, pp. 128-150 (with English language summary).

Wolfe, J.P. et al., 2000, "Scope and limitations of the Pd/BINAP-catalyzed amination of aryl bromides," *J. Org. Chem.*, vol. 65, pp. 1144-1157.

Wolfe, J.P. et al., 2000, "Simple, efficient catalyst system for the palladium-catalyzed amination of aryl chlorides, bromides, and triflates," *J. Org. Chem.*, vol. 65, pp. 1158-1174.

Wong, J., et al., 1998, "Distinct requirements for chromatin assembly in transcriptional repression by thyroid hormone receptor and histone deacetylase," *EMBO J.*, vol. 17(2), pp. 520-534.

Yang, W.M., et al., 1996, "Transcriptional repression of YY1 is mediated by interaction with a mammalian homolog of the yeast global regulator RPD3," *Proc. Natl. Acad. Sci. USA*, vol. 93, pp. 12845-12850.

Yang, W.M., et al., 1997, "Isolation and characterization of cDNAs corresponding to an additional member of the human histone deacetylase gene family," *J. Biol. Chem.*, vol. 272, pp. 28001-28007.

Yoshida et al., 1995, "Trichostatin A and trapoxin: novel chemical probes for the role of histone acetylation in chromatin structure and function," *Bioessays*, vol. 17, pp. 423-430.

Yoshida, M. and Horinouchi, S., 1999, "Inhibition of Histone Deacetylation and Signal-Dependent Nuclear Export," *Ann. N. Y. Acad. Sci.*, vol. 886, pp. 23-36.

Yoshida, M., Beppu, T., 1988, "Reversible arrest of proliferation of rat 3Y1 fibroblasts in both G1 and G2 phases by trichostatin A," *Exp. Cell. Res.*, vol. 177, pp. 122-131.

Yoshida, M., et al., 1990a, "Potent and Specific Inhibition of Mammalian Histone Deacetylase Both in Vivo and in Vitro by Trichostatin A*," *J. Biol. Chem.*, vol. 265(28), pp. 17174-17179.

Yoshida, M., et al., 1990b, "Structural specificity for biological activity of trichostatin A, a specific inhibitor of mammalian cell cycle with potent differentiation-inducing activity in friend leukemia cells," *J. Antibiot.* (Tokyo), vol. 43(9), pp. 1101-1106.

\* cited by examiner

CARBAMIC ACID COMPOUNDS COMPRISING A BICYCLIC HETEROARYL GROUP AS HDAC INHIBITORS

RELATED APPLICATION

This application is the US national phase of international application PCT/GB2004/000765, filed 25 Feb. 2004, which designated the U.S. and claims benefit of U.S. 60/449,394, dated 25 Feb. 2003, the entire contents of each of which are hereby incorporated by reference.

TECHNICAL FIELD

This invention pertains generally to the field of biologically active compounds, and more specifically to certain carbamic acid compounds which inhibit HDAC (histone deacetylase) activity. The present invention also pertains to pharmaceutical compositions comprising such compounds, and the use of such compounds and compositions, both in vitro and in vivo, to inhibit HDAC, and in the treatment of conditions mediated by HDAC, cancer, proliferative conditions, psoriasis, etc.

BACKGROUND

Throughout this specification, including any claims which follow, unless the context requires otherwise, the word "comprise," and variations such as "comprises" and "comprising," will be understood to imply the inclusion of a stated integer or step or group of integers or steps, but not the exclusion of any other integer or step or group of integers or steps.

It must be noted that, as used in the specification and any appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

DNA in eukaryotic cells is tightly complexed with proteins (histones) to form chromatin. Histones are small, positively charged proteins which are rich in basic amino acids (positively charged at physiological pH), which contact the phosphate groups (negatively charged at physiological pH) of DNA. There are five main classes of histones, H1, H2A, H2B, H3, and H4. The amino acid sequences of histones H2A, H2B, H3, and H4 show remarkable conservation between species, whereas H1 varies somewhat, and in some cases is replaced by another histone, e.g., H5. Four pairs of each of H2A, H2B, H3, and H4 together form a disk-shaped octomeric protein core, around which DNA (about 140 base pairs) is wound to form a nucleosome. Individual nucleosomes are connected by short stretches of linker DNA associated with another histone molecule (e.g., H1, or in certain cases, H5) to form a structure resembling a beaded string, which is itself arranged in a helical stack, known as a solenoid.

The majority of histones are synthesised during the S phase of the cell cycle, and newly synthesised histones quickly enter the nucleus to become associated with DNA. Within minutes of its synthesis, new DNA becomes associated with histones in nucleosomal structures.

A small fraction of histones, more specifically, the amino side chains thereof, are enzymatically modified by post-translational addition of methyl, acetyl, or phosphate groups, neutralising the positive charge of the side chain, or converting it to a negative charge. For example, lysine and arginine groups may be methylated, lysine groups may be acetylated, and serine groups may be phosphorylated. For lysine, the $-(CH_2)_4-NH_2$ sidechain may be acetylated, for example by an acetyltransferase enzyme, to give the amide $-(CH_2)_4-NHC(=O)CH_3$. Methylation, acetylation, and phosphorylation of amino termini of histones which extend from the nucleosomal core affects chromatin structure and gene expression. (See, for example, Spencer and Davie, 1999).

Acetylation and deacetylation of histones Is associated with transcriptional events leading to cell proliferation and/or differentiation. Regulation of the function of transcription factors is also mediated through acetylafton. Recent reviews of histone deacetylation include Kouzarides, 1999 and Pazin et al., 1997.

The correlation between the acetylation status of histones and the transcription of genes has been known for over 30 years (see, for example, Howe et al., 1999). Certain enzymes, specifically acetylases (e.g., histone acetyltransferase, HAT) and deacetylases (e.g., histone deacetylase, HDAC), which regulate the acetylation state of histones have been identified in many organisms and have been implicated in the regulation of numerous genes, confirming the link between acetylation and transcription. See, for example, Davie, 1998. In general, histone acetylation correlates with transcriptional activation, whereas histone deacetylation is associated with gene repression.

A growing number of histone deacetylases (HDACs) have been identified (see, for example, Ng and Bird, 2000). The first deacetylase, HDAC1, was identified in 1996 (see, for example, Taunton et al., 1996). Subsequently, two other nuclear mammalian deacetylases were found, HDAC2 and HDAC3 (see, for example, Yang et al., 1996, 1997, and Emiliani et al., 1998). See also, Grozinger et al., 1999; Kao et al., 2000; and Van den Wyngaert et al., 2000.

Eleven (11) human HDACs have been cloned so far:
 HDAC1 (Genbank Accession No. NP_004955)
 HDAC2 (Genbank Accession No. NP_001518)
 HDAC3 (Genbank Accession No. O15379)
 HDAC4 (Genbank Accession No. AAD29046)
 HDAC5 (Genbank Accession No. NP_005465)
 HDAC6 (Genbank Accession No. NP_006035)
 HDAC7 (Genbank Accession No. AAF63491)
 HDAC8 (Genbank Accession No. AAF73428)
 HDAC9 (Genbank Accession No. AAK66821)
 HDAC10 (Genbank Accession No. AAK84023)
 HDAC11 (Genbank Accession No. NM_024827

These eleven human HDACs fall in two distinct classes: HDACs 1, 2, 3 and 8 are in class I, and HDACs 4, 5, 6, 7, 9, 10 and 11 are in class II.

There are a number of histone deacetylases in yeast, including the following:
 RPD3 (Genbank Accession No. NP_014069)
 HDA1 (Genbank Accession No. P53973)
 HOS1 (Genbank Accession No. Q12214)
 HOS2 (Genbank Accession No. P53096)
 HOS3 (Genbank Accession No. Q02959)

There are also numerous plant deacetylases, for example, HD2, in *Zea mays* (Genbank Accession No. AF254073_1).

HDACs function as part of large multiprotein complexes, which are tethered to the promoter and repress transcription. Well characterised transcriptional repressors such as Mad (Laherty et al., 1997), pRb (Brehm et al., 1998), nuclear receptors (Wong et al., 1998) and YY1 (Yang et al., 1997) associate with HDAC complexes to exert their repressor function.

The study of inhibitors of histone deacetylases indicates that these enzymes play an important role in cell proliferation and differentiation. The inhibitor Trichostatin A (TSA) (Yoshida et al., 1990a) causes cell cycle arrest at both G1 and G2 phases (Yoshida and Beppu, 1988), reverts the transformed phenotype of different cell lines, and induces differentiation of Friend leukaemia cells and others (Yoshida et al., 1990b). TSA (and SAHA) have been reported to inhibit cell growth, induce terminal differentiation, and prevent the formation of tumours in mice (Finnin et al., 1999).

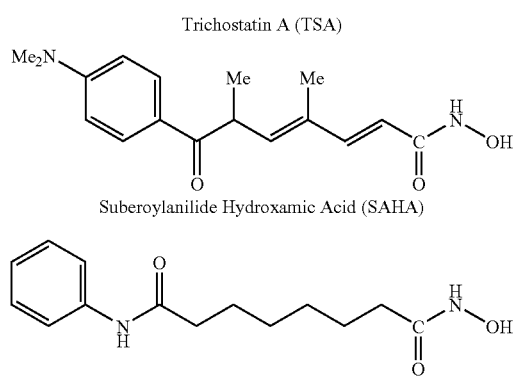

Cell cycle arrest by TSA correlates with an increased expression of gelsolin (Hoshikawa et al., 1994), an actin regulatory protein that is down regulated in malignant breast cancer (Mielnicki et al., 1999). Similar effects on cell cycle and differentiation have been observed with a number of deacetylase inhibitors (Kim et al., 1999).

Trichostatin A has also been reported to be useful in the treatment of fibrosis, e.g., liver fibrosis and liver cirrhosis. See, e.g., Geerts et al., 1998.

Recently, certain compounds that induce differentiation have-been reported to inhibit histone deacetylases. Several experimental antitumour compounds, such as trichostatin A (TSA), trapoxin, suberoylanilide hydroxamic acid (SAHA), and phenylbutyrate have been reported to act, at least in part, by inhibiting histone deacetylase (see, e.g., Yoshida et al., 1990; Richon et al., 1998; Kijima et al., 1993). Additionally, diallyl sulfide and related molecules (see, e.g., Lea et al., 1999), oxamflatin (see, e.g., Kim et al., 1999; Sonoda et al., 1996), MS-27-275, a synthetic benzamide derivative (see, e.g., Saito et al., 1999; Suzuki et al., 1999; note that MS-27-275 was later re-named as MS-275), butyrate derivatives (see, e.g., Lea and Tulsyan, 1995), FR901228 (see, e.g., Nokajima et al., 1998), depudecin (see, e.g., Kwon et al., 1998), and m-carboxycinnamic acid bishydroxamide (see, e.g., Richon et al., 1998) have been reported to inhibit histone deacetylases. In vitro, some of these compounds are reported to inhibit the growth of fibroblast cells by causing cell cycle arrest in the G1 and G2 phases, and can lead to the terminal differentiation and loss of transforming potential of a variety of transformed cell lines (see, e.g., Richon et al, 1996; Kim et al., 1999; Yoshida et al., 1995; Yoshida & Beppu, 1988). In vivo, phenybutyrate is reported to be effective in the treatment of acute promyelocytic leukemia in conjunction with retinoic acid (see, e.g., Warrell et al., 1998). SAHA is reported to be effective in preventing the formation of mammary tumours in rats, and lung tumours in mice (see, e.g., Desai et al., 1999).

The clear involvement of HDACs in the control of cell proliferation and differentiation suggests that aberrant HDAC activity may play a role in cancer. The most direct demonstration that deacetylases contribute to cancer development comes from the analysis of different acute promyelocytic leukemias (APL). In most APL patients, a translocation of chromosomes 15 and 17 (t(15;17)) results in the expression of a fusion protein containing the N-terminal portion of PML gene product linked to most of RARα (retinoic acid receptor). In some cases, a different translocation (t(11;17)) causes the fusion between the zinc finger protein PLZF and RARα. In the absence of ligand, the wild type RARα represses target genes by tethering HDAC repressor complexes to the promoter DNA. During normal hematopoiesis, retinoic acid (RA) binds RARα and displaces the repressor complex, allowing expression of genes implicated in myeloid differentiation. The RARα fusion proteins occurring in APL patients are no longer responsive to physiological levels of RA and they interfere with the expression of the RA-inducible genes that promote myeloid differentiation. This results in a clonal expansion of promyelocytic cells and development of leukaemia. In vitro experiments have shown that TSA is capable of restoring RA-responsiveness to the fusion RARα proteins and of allowing myeloid differentiation. These results establish a link between HDACs and oncogenesis and suggest that HDACs are potential targets for pharmaceutical intervention in APL patients. (See, for example, Kitamura et al., 2000; David et al., 1998; Lin et al., 1998).

Furthermore, different lines of evidence suggest that HDACs may be important therapeutic targets in other types of cancer. Cell lines derived from many different cancers (prostate, colorectal, breast, neuronal, hepatic) are induced to differentiate by HDAC inhibitors (Yoshida and Horinouchi, 1999). A number of HDAC inhibitors have been studied in animal models of cancer. They reduce tumour growth and prolong the lifespan of mice bearing different types of transplanted tumours, including melanoma, leukaemia, colon, lung and gastric carcinomas, etc. (Ueda et al., 1994; Kim et al., 1999).

Psoriasis is a common chronic disfiguring skin disease which is characterised by well-demarcated, red, hardened scaly plaques: these may be limited or widespread. The prevalence rate of psoriasis is approximately 2%, i.e., 12.5 million sufferers in the triad countries (US/Europe/Japan). While the disease is rarely fatal, it clearly has serious detrimental effects upon the quality of life of the patient: this is further compounded by the lack of effective therapies. Present treatments are either ineffective, cosmetically unacceptable, or possess undesired side effects. There is therefore a large unmet clinical need for effective and safe drugs for this condition.

Psoriasis is a disease of complex etiology. Whilst there is clearly a genetic component, with a number of gene loci being involved, there are also undefined environmental triggers. Whatever the ultimate cause of psoriasis, at the cellular level, it is characterised by local T-cell mediated inflammation, by keratinocyte hyperproliferation, and by localised angiogenesis. These are all processes in which histone deacetylases have been implicated (see, e.g., Saunders et al., 1999; Bernhard et al, 1999; Takahashi et al, 1996; Kim et al , 2001). Therefore HDAC inhibitors may be of use in therapy for psoriasis. Candidate drugs may be screened, for example, using proliferation assays with T-cells and/or keratinocytes.

Thus, one aim of the present invention Is the provision of compounds which are potent inhibitors of histone deacetylases (HDACs). There is a pressing need for such compounds, particularly for use as antiproliferatives, for example, anticancer agents, agents for the treatment of psoriasis, etc.

Such molecules desirably have one or more of the following properties and/or effects:
(a) easily gain access to and act upon tumour cells;
(b) down-regulate HDAC activity;
(c) inhibit the formation of HDAC complexes;
(d) inhibit the interactions of HDAC complexes;
(e) inhibit tumour cell proliferation;
(e) promote tumour cell apoptosis;
(f) inhibit tumour growth; and,
(g) complement the activity of traditional chemotherapeutic agents.

A number of carbamic acid compounds have been described.

Certain classes of carbamic acid compounds which inhibit HDAC are described in Watkins et al., 2002a, 2002b, 2002c, 2003.

Quinolines

Kato et al., 1996, describe certain carbamic acid compounds bearing a quinolin-2-yl group (shown below) as potential agents for the treatment of neurodegenerative disorders.

| Cmpd. | Page | Structure | CAS No. |
|---|---|---|---|
| 1-3 | 41 | 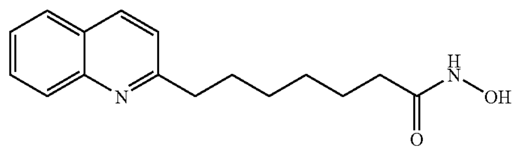 | 183965-19-7P |
| 1-4 | 42 | 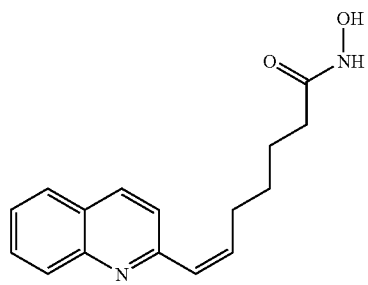 | 183965-21-1P |
| 1-5 | 42 | 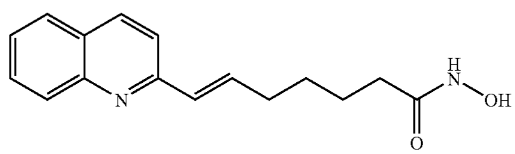 | 183965-22-2P |
| 2-1 | 44 | 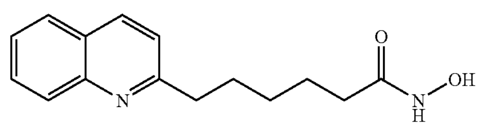 | 183965-25-5P |
| 2-2 | 44 | 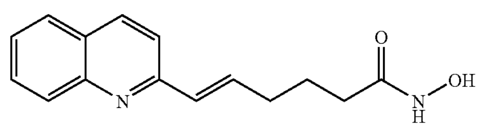 | 183965-26-6P |
| 2-3 | 45 | 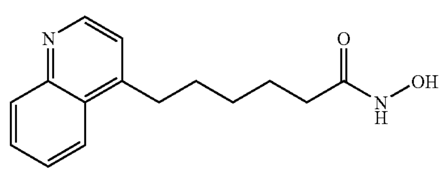 | 183965-27-7P |
| 2-4 | 45 | 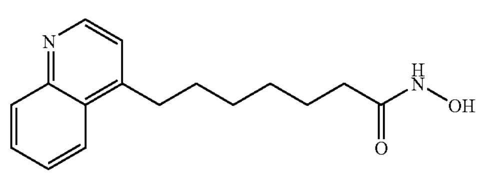 | 183965-28-8P |

-continued

| Cmpd. | Page | Structure | CAS No. |
|---|---|---|---|
| 2-7 | 47 | 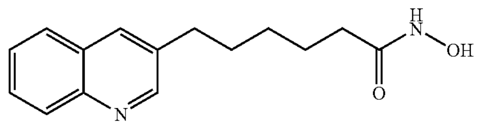 | 183965-31-3P |
| 2-8 | 47 | 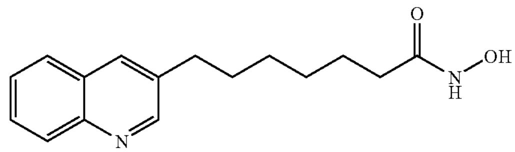 | 183965-32-4P |
| 2-9 | 47 | 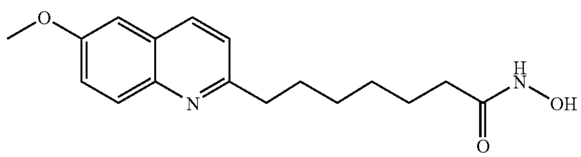 | 183965-33-5P |
| 2-10 | 47 | 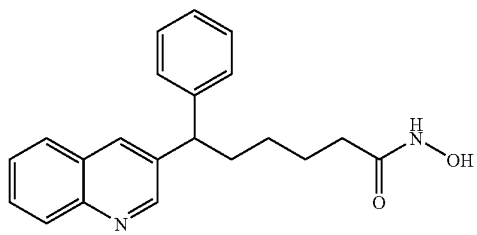 | 183965-34-6P |
| 2-11 | 48 | 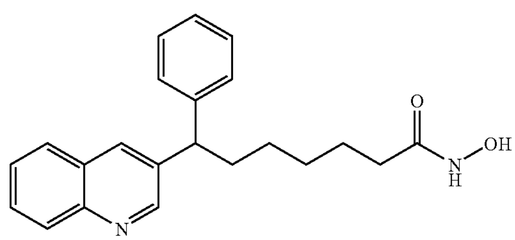 | 183965-35-7P |
| 12 | 37 | 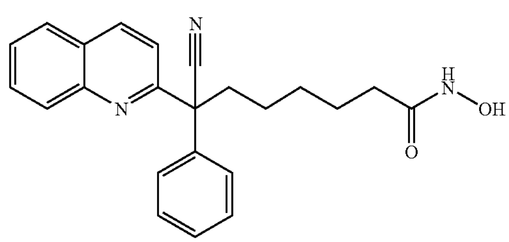 | 186522-77-0P |
| 26 | 41 | 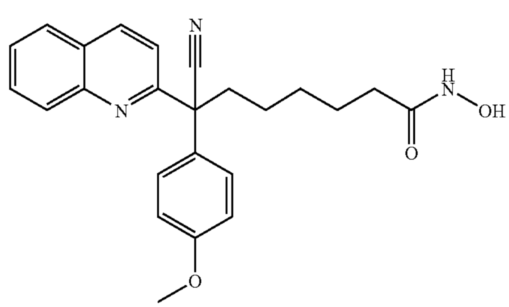 | 186522-97-4P |

-continued

| Cmpd. | Page | Structure | CAS No. |
|---|---|---|---|
| 27 | 41 | (quinolin-2-yl with CN, naphthalen-2-yl, and hexanoyl hydroxamic acid chain) | 186522-98-5P |
| 28 | 41 | (quinolin-2-yl with CN, thiophen-2-yl, and hexanoyl hydroxamic acid chain) | 186522-99-6P |

Musser et al., 1988, describes carbamic acid compounds (including one bearing a quinolin-2-yl group, linked via a methylene-oxy-meta-phenylene ether group) as inhibitors of 5-lipoxygenase/cyclooxygenase and leukotriene antagonists for the treatment of inflammatory and allergic diseases.

| Cmpd | Page | Structure | CAS No. |
|---|---|---|---|
| 4 | 8 | (quinolin-2-yl-methoxy-phenyl hydroxamic acid) | 118308-98-8 |

Benzoxazoles and Related Compounds

Kato et al., 1996, describe a carbamic acid compound bearing a benzoxazol-2-yl group (shown below) as a potential agent for the treatment of neurodegenerauive disorders.

Venkatesan et al., 2001, describe a carbamic acid compound bearing a quinolin-6-yl group (shown below) as an inhibitor of matrix metalloproteases and TNFα converting enzyme (TACE).

| Cmpd. | Column | Structure | CAS No. |
|---|---|---|---|
| 67 | 50 | (quinolin-6-yl-methyl with methoxyphenylsulfonyl hydroxamic acid) | 212766-63-7P |

| Structure | CAS No. |
|---|---|
| [benzoxazole-(CH2)4-C(=O)NHOH] | 183963-81-7P |

Turin et al., 1996, describe certain carbamic acids compounds bearing a furobenzoxazole group (shown below) as potential bronchodilators.

| Structure | CAS No. |
|---|---|
| [methyl-furobenzoxazole-CH2-C(=O)NHOH] | 65874-35-3P |
| [methyl-furobenzoxazole-CH2-C(=O)NHOH isomer] | 65874-38-6P |

Fauran et al, 1974, describe a carbamic acid compound bearing a furobenzoxazole group (shown below) as a potential bronchodilator and hypotensive agent.

| Structure | CAS No. |
|---|---|
| [dimethoxy-furobenzoxazole-CH2-C(=O)NHOH] | 54414-41-4P |

Benzothiazoles

Baxter et al., 2000, describe a carbamic acid compound bearing a benzothiazol-2-yl group (shown below) as an inhibitor of matrix metalloproteases for use in therapy of a number of diseases, including cancer.

| Structure | CAS No. |
|---|---|
| [benzothiazole-(CH2)2-C(=O)NHOH] | 21344-60-5P |

Kato et al., 1996, describe certain carbamic acid compounds bearing a benzothiazol-2-yl group (shown below) as agents for the treatment of neurodegenerative disease:

| Structure | CAS No. |
|---|---|
| [benzothiazole-(CH2)4-C(=O)NHOH] | 183963-77-1P |
| [benzothiazole-(CH2)5-C(=O)NHOH] | 183963-85-1P |

Babichev et al., 1968, describe the synthesis of certain carbamic acid compounds bearing a benzothiazol-2-yl group (shown below).

| Structure | CAS No. |
|---|---|
| [benzothiazole-(CH2)2-C(=O)NHOH] | 21344-60-5P |
| [benzothiazole-(CH2)3-C(=O)NHOH] | 21344-61-6P |
| [benzothiazole-(CH2)4-C(=O)NHOH] | 21344-62-7P |

Benzimidazoles

Strakov et al., 1972 describes the synthesis of a carbamic acid compound bearing a benzimidazol-2-yl group (shown below).

| Structure | CAS No. |
|---|---|
| [benzimidazole-CH2-C(Me)2-CH2-C(=O)NHOH] | 37454-68-5P |

Guines et al., 1992 describes certain carbamic acids compound bearing a benzimidazol-2-yl group (shown below) that apparently have antifungal properties.

| Structure | CAS No. |
|---|---|
| [structure] | 143949-73-9P |
| [structure] | 143949-76-2P |

SUMMARY OF THE INVENTION

One aspect of the invention pertains to active carbamic acid compounds, as described herein.

Another aspect of the invention pertains to active compounds, as described herein, which inhibit HDAC activity.

Another aspect of the invention pertains to active compounds, as described herein, which treat conditions which are known to be mediated by HDAC, or which are known to be treated by HDAC inhibitors (such as, e.g., trichostatin A).

Another aspect of the invention pertains to active compounds, as described herein, which (a) regulate (e.g., inhibit) cell proliferation; (b) inhibit cell cycle progression; (c) promote apoptosis; or (d) a combination of one or more of these.

Another aspect of the invention pertains to active compounds, as described herein, which are anti-HDAC agents, and which treat a condition mediated by HDAC.

Another aspect of the invention pertains to active compounds, as described herein, which are anticancer agents, and which treat cancer.

Another aspect of the invention pertains to active compounds, as described herein, which are antiproliferative agents, and which treat a proliferative condition.

Another aspect of the invention pertains to active compounds, as described herein, which are antipsoriasis agents, and which treat psoriasis.

Another aspect of the present invention pertains to a composition comprising a compound, as described herein, and a carrier.

Another aspect of the present invention pertains to a composition comprising a compound, as described herein, and a pharmaceutically acceptable carrier.

Another aspect of the present invention pertains to methods of inhibiting HDAC in a cell, comprising contacting said cell with an effective amount of an active compound, as described herein, whether in vitro or in vivo.

Another aspect of the present invention pertains to methods of (a) regulating (e.g., inhibiting) cell proliferation; (b) inhibiting cell cycle progression; (c) promoting apoptosis; or (d) a combination of one or more of these, comprising contacting a cell with an effective amount of an active compound, as described herein, whether in vitro or in vivo.

Another aspect of the present invention pertains to methods of treating a condition which is known to be mediated by HDAC, or which is known to be treated by HDAC inhibitors (such as, e.g., trichostatin A), comprising administering to a subject in need of treatment a therapeutically-effective amount of an active compound, as described herein.

Another aspect of the present invention pertains to methods of treating cancer, comprising administering to a subject in need of treatment a therapeutically-effective amount of an active compound, as described herein.

Another aspect of the present invention pertains to methods of treating a proliferative condition comprising administering to a subject in need of treatment a therapeutically-effective amount of an active compound, as described herein.

Another aspect of the present invention pertains to methods of treating psoriasis comprising administering to a subject in need of treatment a therapeutically-effective amount of an active compound, as described herein.

Another aspect of the present invention pertains to an active compound, as described herein, for use in a method of treatment of the human or animal body by therapy.

Another aspect of the present invention pertains to use of an active compound, as described herein, for the manufacture of a medicament for use in the treatment of a condition mediated by HDAC, a condition known to be treated by HDAC inhibitors (such as, e.g., trichostatin A), cancer, a proliferative condition, psoriasis, or other condition as described herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspects of the invention.

DETAILED DESCRIPTION OF THE INVENTION

Compounds

In one aspect, the present invention pertains to carbamic acid compounds of the formula:

$$A-Q-\overset{O}{\underset{}{C}}-\underset{H}{N}-OH \quad (1)$$

wherein:

A is independently an unsubstituted or substituted bicyclic $C_{9-10}$heteroaryl group;

Q is an acid leader group, and is independently an unsubstituted or substituted, saturated or unsaturated $C_{1-7}$alkylene group having a backbone length of 4 or less;

with the proviso that if A is unsubstituted benzothiazol-2-yl, then Q is an unsaturated group; and with the proviso that if A is unsubstituted quinolin-6-yl, then Q is unsubstituted at the α-position; and with the proviso that A is not benzimidazol-2-yl;

and pharmaceutically acceptable salts, solvates, amides, esters, ethers, chemically protected forms, and prodrugs thereof.

In preferred embodiments, the carbamic acid group, —C(=O)NHOH, is unmodified (e.g., is not an ester).

Provisos

In some aspects of the invention (e.g., compounds per se), the compounds are further limited, for example, by a proviso.

For example, in some aspects, the compounds are further limited by the proviso that A is not benzothiazolyl (e.g., unsubstituted benzothiazolyl; e.g., benzothiazol-2-yl; e.g., unsubstituted benzothiazol-2-yl).

For example, in some aspects, the compounds are further limited by the proviso that if A is benzothiazolyl (e.g., unsubstituted benzothiazolyl; e.g., benzothiazol-2-yl; e.g., unsubstituted benzothiazol-2-yl), then Q is an unsaturated group.

For example, in some aspects, the compounds are further limited by the proviso that if A is benzothiazolyl (e.g., unsubstituted benzothiazolyl; e.g., benzothiazol-2-yl; e.g., unsubstituted benzothiazol-2-yl), then Q is unsubstituted at the α-position.

For example, in some aspects, the compounds are further limited by the proviso that if A is benzothiazolyl (e.g., unsubstituted benzothiazolyl; e.g., benzothiazol-2-yl; e.g., unsubstituted benzothiazol-2-yl), then Q is unsubstituted.

For example, in some aspects, the compounds are further limited by the proviso that A is not quinolin-6-yl (e.g., unsubstituted quinolin-6-yl).

For example, in some aspects, the compounds are further limited by the proviso that if A is quinolin-6-yl (e.g., unsubstituted quinolin-6-yl), then Q is an unsaturated group.

For example, in some aspects, the compounds are further limited by the proviso that if A is quinolin-6-yl (e.g., unsubstituted quinolin-6-yl), then Q is unsubstituted at the α-position.

For example, in some aspects, the compounds are further limited by the proviso that if A is quinolin-6-yl (e.g., unsubstituted quinolin-6-yl), then Q is unsubstituted.

For example, in some aspects, the compounds are further limited by the proviso that A is not benzimidazol-2-yl (e.g., benzimidazolyl).

For example, in some aspects, the compounds are further limited by the proviso that if A is benzimidazol-2-yl (e.g., benzimidazolyl), then Q is an unsaturated group.

In some embodiments (e.g., methods of inhibiting HDAC; methods of treatment of proliferative conditions; etc.), one or more of the provisos need not apply (though optionally they may apply).

Heteroaryl Group, A

The heteroaryl group, A, is a bicyclic $C_{9-10}$heteroaryl group, and is optionally substituted.

In one embodiment, A is a bicyclic $C_{9-10}$heteroaryl group selected from:

bicyclic $C_9$heteroaryl groups having a first five-membered ring fused to a second six-membered ring, wherein said first and second rings share exactly two ring atoms (e.g., as in indole); and, bicyclic $C_{10}$heteroaryl groups having a first six-membered ring fused to a second six-membered ring, wherein said first and second rings share exactly two ring atoms (e.g., as in quinoline).

In one embodiment, A is defined both as set out immediately above, and is further limited as set out elsewhere herein.

In one embodiment, A is a bicyclic $C_{9-10}$heteroaryl group having:

1 or 2 aromatic nitrogen ring atoms; and
0 or 1 aromatic oxygen ring atoms; and
0 or 1 aromatic sulfur ring atoms;
and is optionally substituted.

In one embodiment, A is a bicyclic $C_{9-10}$heteroaryl group having:

1 aromatic nitrogen ring atom; or
2 aromatic nitrogen ring atoms; or
1 aromatic nitrogen ring atom and 1 aromatic oxygen ring atom; or
1 aromatic nitrogen ring atom and 1 aromatic sulfur ring atom;
and is optionally substituted.

In one embodiment, A is a bicyclic $C_{9-10}$heteroaryl group having:

1 aromatic nitrogen ring atom, and no other aromatic ring heteroatoms; or
2 aromatic nitrogen ring atoms, and no other aromatic ring heteroatoms; or
1 aromatic nitrogen ring atom and 1 aromatic oxygen ring atom, and no other aromatic ring heteroatoms; or
1 aromatic nitrogen ring atom and 1 aromatic sulfur ring atom, and no other aromatic ring heteroatoms;
and is optionally substituted.

In one embodiment, A is derived from:
quinoline; isoquinoline;
cinnoline; quinazoline; quinoxaline; phthalazine; or naphthyridine;
indole; isoindole;
benzoxazole; or
benzothiazole.

In one embodiment, A is derived from:
quinoline; quinoxaline; benzoxazole; or benzothiazole.

In one embodiment, A is a bicyclic $C_{9-10}$heteroaryl group having the following formula:

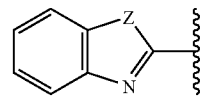

wherein Z is:
—CH=CH— (giving quinolin-2-yl);
—N=CH— (giving quinoxalin-2-yl);
—O— (giving benzoxazol-2-yl); or
—S— (giving benzothiazol-2-yl);
and is optionally substituted.

Heteroaryl Group, A: 1 or 2 Aromatic Nitrogen Ring Atoms

In one embodiment, A is a bicyclic $C_{9-10}$heteroaryl group having 1 or 2 aromatic nitrogen ring atoms, and is optionally substituted.

In one embodiment, A is a bicyclic $C_{9-10}$heteroaryl group having 1 or 2 aromatic nitrogen ring atoms, and no other aromatic ring heteroatoms, and is optionally substituted.

Heteroaryl Group, A: 1 or 2 Aromatic Nitrogen Ring Atoms: $C_{10}$heteroaryl

In one embodiment, A is a bicyclic $C_{10}$heteroaryl group having 1 or 2 aromatic nitrogen ring atoms, and no other aromatic ring heteroatoms, and is optionally substituted.

In one embodiment, A is a bicyclic C₁₀heteroaryl group derived from quinoline; isoquinoline; cinnoline; quinazoline; quinoxaline; phthalazine; or naphthyridine; and is optionally substituted.

In one embodiment, A is quinolinyl; isoquinolinyl; cinnolinyl; quinazolinyl; quinoxalinyl; or phthalazinyl; and is optionally substituted.

In one embodiment, A is a bicyclic C₁₀heteroaryl group derived from quinoline or quinoxaline; and is optionally substituted.

In one embodiment, A is quinolinyl or quinoxalinyl; and is optionally substituted.

In one embodiment, A is quinolin-2-yl; quinolin-3-yl; quinolin-4-yl; quinolin-5-yl; quinolin-6-yl; quinolin-7-yl; quinolin-8-yl; quinoxalin-2-yl; or quinoxalin-3-yl; and is optionally substituted.

Heteroaryl Group, A: 1 or 2 Aromatic Nitrogen Ring Atoms: C₉heteroaryl

In one embodiment, A is a bicyclic C₉heteroaryl group having 1 or 2 aromatic nitrogen ring atoms, and no other aromatic ring heteroatoms, and is optionally substituted.

In one embodiment, A is a bicyclic C₉heteroaryl group derived from: indole; or isoindole; and is optionally substituted.

indole    isoindole

In one embodiment, A is indolyl; or isoindolyl; and is optionally substituted.

Heteroaryl Group, A: 1 Aromatic Nitrogen Ring Atom

In one embodiment, A is a bicyclic C₉₋₁₀heteroaryl group having 1 aromatic nitrogen ring atom, and is optionally substituted.

In one embodiment, A is a bicyclic C₉₋₁₀heteroaryl group having 1 aromatic nitrogen ring atom, and no other aromatic ring heteroatoms, and is optionally substituted.

Heteroaryl Group, A: 1 Aromatic Nitrogen Ring Atom: C₁₀heteroaryl

In one embodiment, A is a bicyclic C₁₀heteroaryl group having 1 aromatic nitrogen ring atom, and no other aromatic ring heteroatoms, and is optionally substituted.

In one embodiment, A is a bicyclic C₁₀heteroaryl group derived from quinoline or isoquinoline, and is optionally substituted.

quinoline    isoquinoline

In one embodiment, A is a quinolinyl or isoquinolinyl, and is optionally substituted.

In one embodiment, A is a bicyclic C₁₀heteroaryl group derived from quinoline, and is optionally substituted.

In one embodiment, A is quinolinyl, and is optionally substituted.

In one embodiment, A is quinolin-2-yl; quinolin-3-yl; quinolin-4-yl; quinolin-5-yl; quinolin-6-yl; quinolin-7-yl; or quinolin-8-yl; and is optionally substituted.

In one embodiment, A is quinolin-2-yl, and is optionally substituted.

In one embodiment, A is quinolin-3-yl, and is optionally substituted.

In one embodiment, A is quinolin-4-yl, and is optionally substituted.

In one embodiment, A is quinolin-5-yl, and is optionally substituted.

In one embodiment, A is quinolin-6-yl, and is optionally substituted.

In one embodiment, A is quinolin-7-yl, and is optionally substituted.

In one embodiment, A is quinolin-8-yl, and is optionally substituted.

In one embodiment, A is a group of the following formula, wherein n is 0, 1, 2, 3, or 4; m is 0, 1, or 2; and each $R^A$ is independently a heteroaryl group substituent, as defined herein:

Heteroaryl Group, A: 2 Aromatic Nitrogen Ring Atoms

In one embodiment, A is a bicyclic C₉₋₁₀heteroaryl group having 2 aromatic nitrogen ring atoms, and is optionally substituted.

In one embodiment, A is a bicyclic C₉₋₁₀heteroaryl group having 2 aromatic nitrogen ring atoms, and no other aromatic ring heteroatoms, and is optionally substituted.

Heteroaryl Group, A: 2 Aromatic Nitrogen Ring Atoms: C₁₀heteroaryl

In one embodiment, A is a bicyclic C₁₀heteroaryl group having 2 aromatic nitrogen ring atoms, and no other aromatic ring heteroatoms, and is optionally substituted.

In one embodiment, A is a bicyclic C₁₀heteroaryl group derived from cinnoline; quinazoline; quinoxaline; phthalazine; 1,8-naphthyridine; 1,7-naphthyridine; 1,6-naphthyridine; 1,5-naphthyridine; 2,7-naphthyridine; or 2,6-naphthyridine; and is optionally substituted.

cinnoline    quinazoline    quinoxaline phthalazine    1,8-naphthyridine    1,7-naphthyridine
(pyrido[3,4-b]pyridine)

1,6-naphthyridine    1,5-naphthyridine    2,7-naphthyridine
(pyrido[4,3-b]pyridine)    (pyrido[3,2-b]pyridine)

-continued

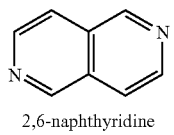

2,6-naphthyridine

In one embodiment, A is a cinnolinyl; quinazolinyl; quinoxalinyl; phthalazinyl; 1,8-naphthyridinyl; 1,7-naphthyridinyl; 1,6-naphthyridinyl; 1,5-naphthyridinyl; 2,7-naphthyridinyl; or 2,6naphthyridinyl; and is optionally substituted.

In one embodiment, A is a bicyclic $C_{10}$heteroaryl group derived from cinnoline, quinazoline, quinoxaline, or phthalazine, and is optionally substituted.

In one embodiment, A is cinnoliny, quinazolinyl, quinoxalinyl, or phthalazinyl, and is optionally substituted.

In one embodiment, A is a bicyclic $C_{10}$heteroaryl group derived from quinoxaline, and is optionally substituted.

In one embodiment, A is quinoxalinyl, and is optionally substituted.

In one embodiment, A is quinoxalin-2-yl or quinoxalin-3-yl, and is optionally substituted. (Note that "quinoxalin-2-yl" and "quinoxalin-3-yl" may refer to the same species, for example, if the quinoxalinyl group is unsubstituted.)

In one embodiment, A is quinoxalin-2-yl, and is optionally substituted.

In one embodiment, A is a group of the following formula, wherein n is 0, 1, 2, 3, or 4; p is 0 or 1; and each $R^A$ is independently a heteroaryl group substituent, as defined herein:

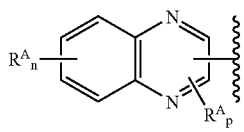

Heteroaryl Group, A:

1 Aromatic Nitrogen Ring Atom and 1 Aromatic Oxygen or Sulfur Ring Atom

In one embodiment, A is a bicyclic $C_{9-10}$heteroaryl group having 1 aromatic nitrogen ring atom and 1 aromatic oxygen or sulfur ring atom, and is optionally substituted.

In one embodiment, A is a bicyclic $C_{9-10}$heteroaryl group having 1 aromatic nitrogen ring atom and 1 aromatic oxygen or sulfur ring atom, and no other aromatic ring heteroatoms, and is optionally substituted.

Heteroaryl Group, A:

1 Aromatic Nitrogen Ring Atom and 1 Aromatic Oxygen Ring Atom

In one embodiment, A is a bicyclic $C_{9-10}$heteroaryl group having 1 aromatic nitrogen ring atom and 1 aromatic oxygen ring atom, and is optionally substituted.

In one embodiment, A is a bicyclic $C_{9-10}$heteroaryl group having 1 aromatic nitrogen ring atom and 1 aromatic oxygen ring atom, and no other aromatic ring heteroatoms, and is optionally substituted.

Heteroaryl Group, A:

1 Aromatic Nitrogen Ring Atom and 1 Aromatic Oxygen Ring Atom: $C_9$heteroaryl

In one embodiment, A is a bicyclic $C_9$heteroaryl group having 1 aromatic nitrogen ring atom and 1 aromatic oxygen ring atom, and is optionally substituted.

In one embodiment, A is a bicyclic $C_9$heteroaryl group having 1 aromatic nitrogen ring atom and 1 aromatic oxygen ring atom, and no other aromatic ring heteroatoms, and is optionally substituted.

In one embodiment, A is a bicyclic $C_9$heteroaryl group derived from benzoxazole, and is optionally substituted.

benzoxazole

In one embodiment, A is benzoxazolyl, and is optionally substituted.

In one embodiment, A is benzoxazol-2-yl, and is optionally substituted.

In one embodiment, A is a group of the following formula, wherein n is 0, 1, 2, 3, or 4, and each $R^A$ is independently a heteroaryl group substituent, as defined herein:

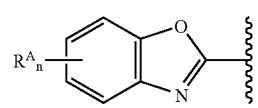

Heteroaryl Group, A:

1 Aromatic Nitrogen Ring Atom and 1 Aromatic Sulfur Ring Atom

In one embodiment, A is a bicyclic $C_{9-10}$heteroaryl group having 1 aromatic nitrogen ring atom and 1 aromatic sulfur ring atom, and is optionally substituted.

In one embodiment, A is a bicyclic $C_{9-10}$heteroaryl group having 1 aromatic nitrogen ring atom and 1 aromatic sulfur ring atom, and no other aromatic ring heteroatoms, and is optionally substituted.

Heteroaryl Group, A:

1 Aromatic Nitrogen Ring Atom and 1 Aromatic Sulfur Ring Atom: $C_9$heteroaryl

In one embodiment, A is a bicyclic $C_9$heteroaryl group having 1 aromatic nitrogen ring atom and 1 aromatic sulfur ring atom, and no other aromatic ring heteroatoms, and is optionally substituted.

In one embodiment, A is a bicyclic $C_9$heteroaryl group derived from benzothiazole, and is optionally substituted.

benzothiazole

In one embodiment, A is benzothiazolyl, and is optionally substituted.

In one embodiment, A is benzothiazol-2-yl, and is optionally substituted.

In one embodiment, A is a group of the following formula, wherein n is 0, 1, 2, 3, or 4, and each $R^A$ is independently a heteroaryl group substituent, as defined herein:

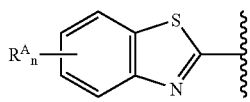

Heteroaryl Group, A: Some Preferred Classes

In one embodiment, A is a bicyclic $C_{9-10}$heteroaryl group derived from: quinoline; isoquinoline; cinnoline; quinazoline; quinoxaline; phthalazine; naphthyridine, benzoxazole; or benzothiazole; and is optionally substituted.

In one embodiment, A is a bicyclic $C_{9-10}$heteroaryl group derived from: quinoline; isoquinoline; cinnoline; quinazoline; quinoxaline; phthalazine; naphthyridine; or benzoxazole; and is optionally substituted.

In one embodiment, A is quinolinyl; isoquinolinyl; cinnolinyl; quinazolinyl; quinoxalinyl; phthalazinyl; naphthyridinyl; benzoxazolyl; benzothiazolyl; and is optionally substituted.

In one embodiment, A is quinolinyl; isoquinolinyl; cinnolinyl; quinazolinyl; quinoxalinyl; phthalazinyl; naphthyridinyl; or benzoxazolyl; and is optionally substituted.

In one embodiment, A is a bicyclic $C_{9-10}$heteroaryl group derived from: quinoline; quinoxaline; benzoxazole; or benzothiazole; and is optionally substituted.

In one embodiment, A is a bicyclic $C_{9-10}$heteroaryl group derived from: quinoline; quinoxaline; or benzoxazole; and is optionally substituted.

In one embodiment, A is quinolinyl; quinoxalinyl; benzoxazolyl; or benzothiazolyl; and is optionally substituted.

In one embodiment, A is quinolinyl; quinoxalinyl; or benzoxazolyl; and is optionally substituted.

In one embodiment, A is quinolin-2-yl; quinolin-3-yl; quinolin-4-yl; quinolin-5-yl; quinolin-6-yl; quinolin-7-yl; quinolin-8-yl; quinoxalin-2-yl; quinoxalin-3-yl; benzoxazol-2-yl; or benzothiazol-2-yl; and is optionally substituted.

In one embodiment, A is quinolin-2-yl; quinolin-3-yl; quinolin-4-yl; quinolin-5-yl; quinolin-6-yl; quinolin-7-yl; quinolin-8-yl; quinoxalin-2-yl; quinoxalin-3-yl; or benzoxazol-2-yl; and is optionally substituted.

Heteroaryl Group Substituents

In one embodiment, A is independently unsubstituted or substituted.

In one embodiment, A is independently substituted.

In one embodiment, A is independently unsubstituted.

If the heteroaryl group, A, has less than the full complement of ring substituents, the ring substituents may be arranged in any combination.

Note that it is not intended that substituents on the heteroaryl group, A, give rise to an additional fused ring. For example, it is not intended that two substituents on A together form a bidentate substituent attached to A, such as —O—CH$_2$—O—, —O—CH$_2$—CH$_2$—O—, —CH=CH—O—, —CH=CH—CH=CH—, etc. It is not intended that A forms part of a larger tricyclic, tetracyclic, etc., group. For example, it is not intended that A be acridinyl, phenanthridinyl, phenazinyl, furobenzoxazolyl, furobenzothiazolyl, etc.

Examples of substituents on A (e.g., $R^A$), include, but are not limited to, those described under the heading "Substituents" below.

In one embodiment, each of the substituents on A (e.g., $R^A$) is independently selected from:

(1) carboxylic acid; (2) ester; (3) amido; (4) acyl; (5) halo; (6) cyano; (7) nitro; (8) hydroxy; (9) ether; (10) thiol; (11) thioether; (12) acyloxy; (13) amino; (14) acylamino; (15) aminoacylamino; (16) sulfonamino; (17) sulfonyl; (18) sulfonate; (19) sulfonamido; (20) $C_{5-20}$aryl-$C_{1-7}$alkyl; (21) $C_{5-20}$aryl; (22) $C_{3-20}$heterocyclyl; (23) $C_{1-7}$alkyl; (24) oxo; (25) imino; (26) hydroxyimino.

In one embodiment, each of the substituents on A (e.g., $R^A$) is independently selected from:

(1) —C(=O)OH;
(2) —C(=O)OR$^1$, wherein R$^1$ is independently as defined in (20), (21), (22) or (23);
(3) —C(=O)NR$^2$R$^3$, wherein each of R$^2$ and R$^3$ is independently —H; or as defined in (20), (21), (22) or (23); or R$^2$ and R$^3$ taken together with the nitrogen atom to which they are attached form a ring having from 3 to 7 ring atoms;
(4) —C(=O)R$^4$, wherein R$^4$ is independently as defined in (20), (21), (22) or (23);
(5) —F, —Cl, —Br, —I;
(6) —CN;
(7) —NO$_2$;
(8) —OH;
(9) —OR$^5$, wherein R$^5$ is independently as defined in (20), (21), (22) or (23);
(10) —SH;
(11) —SR$^6$, wherein R$^6$ is independently as defined in (20), (21), (22) or (23);
(12) —OC(=O)R$^7$, wherein R$^7$ is independently as defined in (20), (21), (22) or (23);
(13) —NR$^8$R$^9$, wherein each of R$^8$ and R$^9$ is independently —H; or as defined in (20), (21), (22) or (23); or R$^8$ and R$^9$ taken together with the nitrogen atom to which they are attached form a ring having from 3 to 7 ring atoms;
(14) —NR$^{10}$C(=O)R$^{11}$, wherein R$^{10}$ is independently —H; or as defined in (20), (21), (22) or (23); and R$^{11}$ is independently —H, or as defined in (20), (21), (22) or (23);
(15) —NR$^{12}$C(=O)NR$^{13}$R$^{14}$ or —NR$^{12}$C(=S)NR$^{13}$R$^{14}$, wherein R$^{12}$ is independently —H; or as defined in (20), (21); (22) or (23); and each of R$^{13}$ and R$^{14}$ is independently —H; or as defined in (20), (21), (22) or (23); or R$^{13}$ and R$^{14}$ taken together with the nitrogen atom to which they are attached form a ring having from 3 to 7 ring atoms;
(16) —NR$^{15}$SO$_2$R$^{16}$, wherein R$^{15}$ is independently —H; or as defined in (20), (21), (22) or (23); and R$^{16}$ is independently —H, or as defined in (20), (21), (22) or (23);
(17) —SO$_2$R$^{17}$, wherein R$^{17}$ is independently as defined in (20), (21), (22) or (23);
(18) —OSO$_2$R$^{18}$, wherein R$^{18}$ is independently as defined in (20), (21), (22) or (23);
(19) —SO$_2$NR$^{19}$R$^{20}$, wherein each of R$^{19}$ and R$^{20}$ is independently —H; or as defined in (20), (21), (22) or (23); or R$^{19}$ and R$^{20}$ taken together with the nitrogen atom to which they are attached form a ring having from 3 to 7 ring atoms;
(20) $C_{5-20}$aryl-$C_{1-7}$alkyl, for example, wherein $C_{5-20}$aryl is as defined in (21); unsubstituted or substituted with one or more groups as defined in (1) to (26);
(21) $C_{5-20}$aryl, including $C_{6-20}$carboaryl and $C_{5-20}$heteroaryl; unsubstituted or substituted with one or more groups as defined in (1) to (26);
(22) $C_{3-20}$heterocyclyl; unsubstituted or substituted with one or more groups as defined in (1) to (26);
(23) $C_{1-7}$alkyl, including:
  unsaturated $C_{1-7}$alkyl, e.g., $C_{2-7}$alkenyl and $C_{2-7}$alkynyl;

cyclic $C_{1-7}$alkyl, e.g., $C_{3-7}$cycloalkyl $C_{3-7}$cycloalkenyl, $C_{3-7}$cycloalkynyl;

$C_{1-7}$alkyl substituted with one or more groups as defined in (1) to (22) and (24) to (26),
e.g., halo-$C_{1-7}$alkyl;
e.g., amino-$C_{1-7}$alkyl (e.g., —$(CH_2)_w$-amino, w is 1, 2, 3, or 4);
e.g., carboxy-$C_{1-7}$alkyl (e.g., —$(CH_2)_w$—COOH, w is 1, 2, 3, or 4);
e.g., hydroxy-$C_{1-7}$alkyl (e.g., —$(CH_2)_w$—OH, w is 1, 2, 3, or 4);
e.g., $C_{1-7}$alkoxy-$C_{1-7}$alkyl (e.g., —$(CH_2)_w$—O—$C_{1-7}$alkyl, w is 1, 2, 3, or 4);

(24) =O;
(25) =$NR^{21}$, wherein $R^{21}$ is independently —H; or as defined in (20), (21), (22) or (23);
(26) =NOH.

In one embodiment, each of the substituents on A (e.g., $R^A$) is independently selected from:

(1) —C(=O)OH;
(2) —C(=O)OMe, —C(=O)OEt, —C(=O)O(iPr), —C(=O)O(tBu); —C(=O)O(cPr);
—C(=O)OCH$_2$CH$_2$OH, —C(=O)OCH$_2$CH$_2$OMe, —C(=O)OCH$_2$CH$_2$OEt;
—C(=O)OPh, —C(=O)OCH$_2$Ph;
(3) —(C=O)NH$_2$, —(C=O)NMe$_2$, —(C=O)NEt$_2$, —(C=O)N(iPr)$_2$, —(C=O)N(CH$_2$CH$_2$OH)$_2$;
—(C=O)-morpholino, —(C=O)NHPh, —(C=O)NHCH$_2$Ph;
(4) —(C=O)Me, —(C=O)Et, —(C=O)(tBu), —(C=O)-cHex, —(C=O)Ph; —(C=O)CH$_2$Ph;
(5) —F, —Cl, —Br, —I;
(6) —CN;
(7) —NO$_2$;
(8) —OH;
(9) —OMe, —OEt, —O(iPr), —O(tBu), —OPh, —OCH$_2$Ph;
—OCF$_3$, —OCH$_2$CF$_3$;
—OCH$_2$CH$_2$OH, —OCH$_2$CH$_2$OMe, —OCH$_2$CH$_2$OEt;
—OCH$_2$CH$_2$NH$_2$, —OCH$_2$CH$_2$NMe$_2$, —OCH$_2$CH$_2$N(iPr)$_2$;
—OPh-Me, —OPh-OH, —OPh-OMe, —OPh-F, —OPh-Cl, —OPh-Br, —OPh-I;
(10) —SH;
(11) —SMe, —SEt, —SPh, —SCH$_2$Ph;
(12) —OC(=O)Me, —OC(=O)Et, —OC(=O)(iPr), —OC(=O)(tBu); —OC(=O)(cPr);
—OC(=O)CH$_2$CH$_2$OH, —OC(=O)CH$_2$CH$_2$OMe, —OC(=O)CH$_2$CH$_2$OEt;
—OC(=O)Ph, —OC(=O)CH$_2$Ph;
(13) —NH$_2$, —NHMe, —NHEt, —NH(iPr), —NMe$_2$, —NEt$_2$, —N(iPr)$_2$, —N(CH$_2$CH$_2$OH)$_2$;
—NHPh, —NHCH$_2$Ph; piperidino, piperazino, morpholino;
(14) —NH(C=O)Me, —NH(C=O)Et, —NH(C=O)Ph, —NHC(=O)CH$_2$Ph;
—NMe(C=O)Me, —NMe(C=O)Et, —NMe(C=O)Ph, —NMeC(=O)CH$_2$Ph;
(15) —NH(C=O)NH$_2$, —NH(C=O)NHMe, —NH(C=O)NHEt, —NH(C=O)NPh,
—NH(C=O)NHCH$_2$Ph; —NH(C=S)NH$_2$, —NH(C=S)NHMe, —NH(C=S)NHEt,
—NH(C=S)NPh, —NH(C=S)NHCH$_2$Ph;
(16) —NHSO$_2$Me, —NHSO$_2$Et, —NHSO$_2$Ph, —NHSO$_2$PhMe, —NHSO$_2$CH$_2$Ph;
—NMeSO$_2$Me, —NMeSO$_2$Et, —NMeSO$_2$Ph, —NMeSO$_2$PhMe, —NMeSO$_2$CH$_2$Ph;
(17) —SO$_2$Me, —SO$_2$CF$_3$, —SO$_2$Et, —SO$_2$Ph, —SO$_2$PhMe, —SO$_2$CH$_2$Ph;
(18) —OSO$_2$Me, —OSO$_2$CF$_3$, —OSO$_2$Et, —OSO$_2$Ph, —OSO$_2$PhMe, —OSO$_2$CH$_2$Ph;
(19) —SO$_2$NH$_2$, —SO$_2$NHMe, —SO$_2$NHEt, —SO$_2$NMe$_2$—, —SO$_2$NEt$_2$, —SO$_2$-morpholino, —SO$_2$NHPh, —SO$_2$NHCH$_2$Ph;
(20) —CH$_2$Ph, —CH$_2$Ph-Me, —CH$_2$Ph-OH, —CH$_2$Ph-F, —CH$_2$Ph-Cl;
(21) -Ph, -Ph-Me, -Ph-OH, -Ph-OMe, -Ph-F, -Ph-Cl, -Ph-Br, -Ph-I;
pyridyl, pyrazinyl, pyrimidinyl, pyridazinyl; furanyl, thiophenyl, pyrrolyl, imidazolyl, pyrazolyl, oxazolyl, thiazolyl;
(22) pyrrolidinyl, piperidinyl, azepinyl, tetrahydropyranyl, morpholinyl, azetidinyl, piperazinyl, imidazolinyl; iperazinedionyl, and oxazolinonyl;
(23) —Me, -Et, -nPr, -iPr, -nBu, -iBu, -sBu, -tBu, -nPe; -cPr, -cHex; —CH=CH$_2$, —CH$_2$—CH=CH$_2$;
—CF$_3$, —CHF$_2$, —CH$_2$F, —CCl$_3$, —CBr$_3$, —CH$_2$CH$_2$F, —CH$_2$CHF$_2$, and —CH$_2$CF$_3$;
—CH$_2$OH, —CH$_2$OMe, —CH$_2$OEt, —CH$_2$NH$_2$, —CH$_2$NMe$_2$;
—CH$_2$CH$_2$OH, —CH$_2$CH$_2$OMe, —CH$_2$CH$_2$OEt, —CH$_2$CH$_2$CH$_2$NH$_2$, —CH$_2$CH$_2$NMe$_2$;
(24) =O;
(25) =NH, =NMe; =NEt;
(26) =NOH.

In one embodiment, each of the substituents on A (e.g., each $R^A$), is independently selected from:

(2) —C(=O)OMe, —C(=O)O(Pr);
(3) —C(=O)NHMe;
(4) —C(=O)Et, —C(=O)Ph;
(5) —F, —Cl;
(7) —NO$_2$;
(9) —OMe, —OEt, —OPh, —OCH$_2$CH$_2$OH, —O—CH$_2$-Ph;
(13) —NMe$_2$;
(17) —SO$_2$Me, —SO$_2$Me$_2$;
(20) —CH$_2$-Ph;
(21) -Ph, -Ph-F, -Ph-Cl;
(23) -Me, -Et, -nPr, iPr, —CF$_3$, —CH$_2$CH$_2$OH, —CH$_2$CH$_2$NMe$_2$.

In one embodiment, each of the substituents on A (e.g., each $R^A$), is independently selected from:

(5) —F, —Cl;
(9) —OMe, —OEt, —OPh, —O—CH$_2$-Ph;
(20) —CH$_2$-Ph;
(21) -Ph;
(23) -Me, -Et.

The Acid Leader Group, Q

In one embodiment, the acid leader group, Q, is independently an unsubstituted or substituted, saturated or unsaturated $C_{1-7}$alkylene group having a backbone length of 4 or less.

In one embodiment, Q is independently $C_{1-7}$alkylene, and is optionally substituted and has a backbone length of 4 or less.

In one embodiment, Q is independently a saturated $C_{1-7}$alkylene group and has a backbone length of 4 or less.

In one embodiment, Q is independently an unsaturated (e.g., partially unsaturated, fully unsaturated) $C_{2-7}$alkylene group and has a backbone length of 4 or less.

In one embodiment, Q is independently an aliphatic $C_{1-7}$alkylene group and has a backbone length of 4 or less.

In one embodiment, Q is independently a linear $C_{1-7}$alkylene group and has a backbone length of 4 or less.

In one embodiment, Q is independently a branched $C_{2-7}$alkylene group and has a backbone length of 4 or less.

In one embodiment, Q is independently an alicyclic $C_{3-7}$alkylene group and has a backbone length of 4 or less.

In one embodiment, Q is independently a saturated aliphatic $C_{1-7}$alkylene group and has a backbone length of 4 or less.

In one embodiment, Q is independently a saturated linear $C_{1-7}$alkylene group and has a backbone length of 4 or less.

In one embodiment, Q is independently a saturated branched $C_{2-7}$alkylene group and has a backbone length of 4 or less.

In one embodiment, Q is independently a saturated alicyclic $C_{3-7}$alkylene group and has a backbone length of 4 or less.

In one embodiment, Q is independently a partially unsaturated aliphatic $C_{2-7}$alkylene group and has a backbone length of 4 or less.

In one embodiment, Q is independently a partially unsaturated linear $C_{2-7}$alkylene group and has a backbone length of 4 or less.

In one embodiment, Q is independently a partially unsaturated branched $C_{2-7}$alkylene group and has a backbone length of 4 or less.

In one embodiment, Q is independently a partially unsaturated-alicyclic $C_{3-7}$alkylene group and has a backbone length of 4 or less.

The Acid Leader Group, Q: Backbone Length

The acid leader group, Q, has a backbone length, as determined by the number of chain atoms in the shortest continuous chain of atoms linking an aromatic ring atom of the aryl group, A, and the carbamic acid group, —C(═O)NHOH.

Some examples of backbone length calculations are shown below.

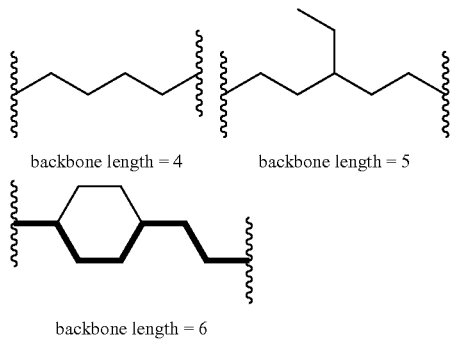

backbone length = 4    backbone length = 5 backbone length = 6

In one embodiment, the Q backbone is independently a carbon backbone.

In one embodiment, the backbone of "atoms" is a backbone of "carbon atoms."

When Q is $C_{1-7}$alkylene, it necessarily has a backbone length of at least 1 atom.

In one embodiment, Q has a backbone length of at least 1 atom.

In one embodiment, Q has a backbone length of at least 2 atoms.

In one embodiment, Q has a backbone length of at least 3 atoms.

In one embodiment, Q has a backbone length of from 1 to 2 atoms (i.e., 1, 2).

In one embodiment, Q has a backbone length of from 1 to 3 atoms (i.e., 1, 2, 3).

In one embodiment, Q has a backbone length of from 1 to 4 atoms (i.e., 1, 2, 3, 4).

In one embodiment, Q has a backbone length of from 2 to 4 atoms (i.e., 2, 3, 4).

In one embodiment, Q has a backbone length of from 2 to 3 atoms (i.e., 2, 3).

In one embodiment, Q has a backbone length of from 3 to 4 atoms (i.e., 3, 4).

In one embodiment, Q has a backbone length of 1 atom.

In one embodiment, Q has a backbone length of 2 atoms.

In one embodiment, Q has a backbone length of 3 atoms.

In one embodiment, Q has a backbone length of 4 atoms

Note that, for embodiments which are characterised by, or further characterised by, a backbone length limitation, corresponding changes in the description of that embodiment may be implicit. For example, for an embodiment wherein (a) Q is a $C_{1-7}$alkylene group, (b) Q is partially unsaturated, and (c) Q has a backbone length of at least 3, the term "$C_{1-7}$alkylene" group is necessarily, and implicitly, interpreted as "$C_{3-7}$alkylene."

The Acid Leader Group, Q: Substitution

In one embodiment, Q is independently unsubstituted or substituted.

In one embodiment, Q is independently substituted.

In one embodiment, Q is independently unsubstituted.

The backbone atoms of the acid leader group, Q, which link the heteroaryl group and the carbamic acid group (—C(═O)NHOH), are denoted α, β, γ, δ, etc., starting with the backbone atom adjacent to the carbamic acid group. An example is illustrated below.

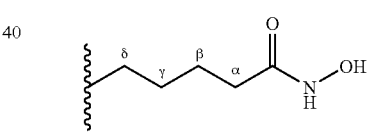

Without wishing to be bound to any particular theory, it is believed that groups (e.g., substituents), particularly bulky groups (e.g., substituents), at the α-position, or at either or both of the α- and β-positions, prevent or reduce the interaction of the carbamic acid group (—C(═O)NHOH) with HDAC (or its complexes), and thereby reduce the compound's activity as an HDAC inhibitor.

In one embodiment, Q is, additionally, unsubstituted at the α-position.

In one embodiment, Q is, additionally, unsubstituted at the α-position and unsubstituted at the β-position.

Note that, in some embodiments, Q may have a non-linear alkylene group (for example, a branched alkylene) adjacent to the carbamic acid group. An example, wherein Q is a branched saturated $C_5$-alkylene, having a methyl group at the α-position, is shown below. Although there is a group (i.e., a methyl group) at the α-position, such compounds are unsubstituted at the α-position, because the α-methyl group itself is considered to be part of the unsubstituted Q. Another example, wherein Q is a branched saturated $C_5$-alkylene, having an amino group at the α-position and a methyl group at the β-position, is shown below; such compounds are α-substituted, β-unsubstituted.

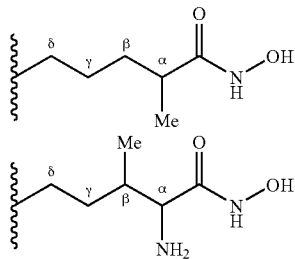

In one embodiment, in which Q is a group as defined herein having an alkylene group adjacent to the carbamic acid group:

(a) Q is, additionally, unsubstituted at the α-position and/or:

(b) that adjacent alkylene group has a —$CH_2$— or =CH— group adjacent to the carbamic acid group (that is, at the α-position) and/or:

(c) that adjacent alkylene group has a —$CH_2$— group adjacent to the carbamic acid group (that is, at the α-position) and/or:

(d) that adjacent alkylene group has a =CH— group adjacent to the carbamic acid group (that is, at the α-position).

In one embodiment, in which Q is a group as defined herein having an alkylene group adjacent to the carbamic acid group:

(a) Q is, additionally, unsubstituted at the a-position and unsubstituted at the β-position and/or:

(b) that adjacent alkylene group has a —$CH_2CH_2$—, —CH=CH—, or —C≡C— group adjacent to the carbamic acid group (that is, at the α,β-position) and/or:

(c) that adjacent alkylene group has a —$CH_2CH_2$— or —CH=CH— group adjacent to the carbamic acid group (that is, at the α,β-position) and/or:

(d) that adjacent alkylene group has a —$CH_2CH_2$— group adjacent to the carbamic acid group (that is, at the α,β-position) and/or:

(e) that adjacent alkylene group has a —CH=CH— group adjacent to the carbamic acid group (that is, at the α,β-position).

The Acid Leader Group, Q: Substituents

Examples of substituents on Q include, but are not limited to, those described under the heading "Substituents" below.

Further examples of substituents Q include, but are not limited to, those described under the heading "Heteroaryl Group Substituents" above (but excluding (23) $C_{1-7}$alkyl, since the alkyl portion thereof would be considered to be part of Q).

In one embodiment, substituents on Q, if present, are independently selected from:

(3) amido; (4) acyl; (5) halo; (7) nitro; (8) hydroxy; (9) ether; (13) amino; (14) acylamino; (20) $C_{5-20}$aryl-$C_{1-7}$alkyl; (21) $C_{5-20}$aryl; (24) oxo; (25) imino; (26) hydroxyimino.

In one embodiment, substituents on Q, if present, are independently selected from:

(3) —$CONH_2$, —$CONMe_2$;
(4) —C(=O)Me;
(5) —F, —Cl, —Br, —I;
(7) —$NO_2$;
(8) —OH;
(9) —OMe, —OEt, —O(iPr);
(13) —$NH_2$, —$NMe_2$, —$NEt_2$, morpholino;
(14) —NHCOMe;
(21) -Ph;
(24) =O;
(25) =NH, =NMe;
(26) =NOH.

The Acid Leader Group, Q: Alkylene: Examples

Note that, for embodiments excluding, e.g., certain backbone lengths, absence of adjacent carbon-carbon double bonds, etc., it is to be understood that the corresponding species listed below are similarly excluded from the respective embodiments discussed below.

In one embodiment, Q is selected from:

—$CH_2$—, —$(CH_2)_2$—, —$(CH_2)_3$—, —$(CH_2)_4$—;
—$CH(CH_3)$—;
—$CH(CH_3)CH_2$—, —$CH_2CH(CH_3)$—;
—$CH(CH_3)CH_2CH_2$—, —$CH_2CH(CH_3)CH_2$—, —$CH_2CH_2CH(CH_3)$—;
—$CH(CH_3)CH_2CH_2CH_2$—, —$CH_2CH(CH_3)CH_2CH_2$—, —$CH_2CH_2CH(CH_3)CH_2$—, —$CH_2CH_2CH_2CH(CH_3)$—;
—$CH(CH_2CH_3)$—;
—$CH(CH_2CH_3)CH_2$—, —$CH_2CH(CH_2CH_3)$—;
—$CH(CH_2CH_3)CH_2CH_2$—, —$CH_2CH(CH_2CH_3)CH_2$—, —$CH_2CH_2CH(CH_2CH_3)$—;
—$CH(CH_2CH_3)CH_2CH_2CH_2$—, —$CH_2CH(CH_2CH_3)CH_2CH_2$—, —$CH_2CH_2CH(CH_2CH_3)CH_2$—, —$CH_2CH_2CH_2CH(CH_2CH_3)$—;
—CH=CH—;
—CH=$CHCH_2$—, —$CH_2$CH=CH—;
—CH=$CHCH_2CH_2$—, —$CH_2$CH=$CHCH_2$—, —$CH_2CH_2$CH=CH—;
—C($CH_3$)=CH—, —CH=C($CH_3$)—;
—C($CH_3$)=$CHCH_2$—, —CH=C($CH_3$)$CH_2$—, —CH=CHCH($CH_3$)—;
—CH($CH_3$)CH=CH—, —$CH_2$C($CH_3$)=CH—, —$CH_2$CH=C($CH_3$)—;
—CH=CHCH=CH—;
—C($CH_3$)=CHCH=CH—, —CH=C($CH_3$)CH=CH—, —CH=CHC($CH_3$)=CH—, —CH=CHCH=C($CH_3$)—;
—C≡C—;
—C≡$CCH_2$—, —$CH_2$C≡C—; —C≡CCH($CH_3$)—, —CH($CH_3$)C≡C—;
—C≡$CCH_2CH_2$—, —$CH_2$C≡$CCH_2$—, —$CH_2CH_2$C≡C—;
—C≡CCH($CH_3$)$CH_2$—, —C≡$CCH_2$CH($CH_3$)—;
—CH($CH_3$)C≡$CCH_2$—, —$CH_2$C≡CCH($CH_3$)—;
—CH($CH_3$)$CH_2$C≡C—, —$CH_2$CH($CH_3$)C≡C—;
—C≡CCH=CH—, —CH=CHC≡C—, —C≡CC≡C—;
—C($CH_3$)=CHC≡C—, —CH=C($CH_3$)C≡C—, —C≡CC($CH_3$)=CH—, —C≡CCH=C($CH_3$)— cyclopentylene cyclopentenylene;
cyclohexylene, cyclohexenylene, cyclohexadienylene;

(cyclopent-1,3-ylene) (4-cyclopenten-1,3-ylene) (cyclohex-1,4-ylene)

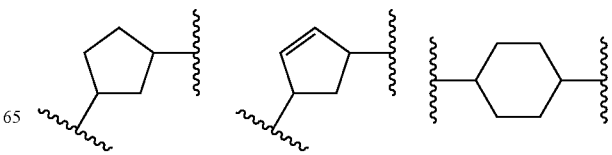

(cyclohex-1,3-ylene)    (2,5-cyclohexadien-1,4-ylene)

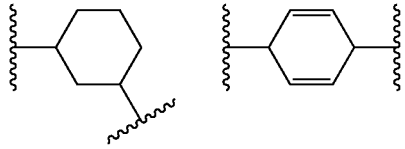

(2-cyclohexen-1,4-ylene)

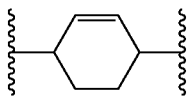

In one preferred embodiment, Q is selected from:
—CH$_2$—, —(CH$_2$)$_2$—, —(CH$_2$)$_3$—, —(CH$_2$)$_4$—;
—CH=CH—;
—CH=CHCH$_2$—;
—CH$_2$CH=CHCH$_2$—;
—CH=CHCH=CH—;
—CH$_2$CH$_2$CH=CH—; and

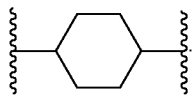

In one preferred embodiment, Q is selected from:
—CH$_2$—, —(CH$_2$)$_2$—, —(CH$_2$)$_3$—, —(CH$_2$)$_4$—;
—CH=CH—;
—CH=CHCH$_2$—;
—CH$_2$CH=CHCH$_2$—;
—CH=CHCH=CH—;
—CH$_2$CH$_2$CH=CH—.

In one preferred embodiment, Q is —CH=CH—, —CH$_2$CH$_2$—, —CH(CH$_3$)CH$_2$—, or —CH$_2$CH(CH$_3$)—.

In one preferred embodiment, Q is —CH=CH— or —CH$_2$CH$_2$—.

In one preferred embodiment, Q is ethenylene (vinylene) (—CH=CH—).

In one preferred embodiment, Q is ethylene (—CH$_2$CH$_2$—).

Other Q Groups: Ethers and Thioethers

In one embodiment, Q is an ether linkage, —R$^2$—X—R$^3$—, wherein X is an ether heteroatom, and is —O— or —S—; and, each of R$^2$ and R$^3$ (the ether groups) is independently:

(a) C$_{1-7}$alkylene;
and is optionally substituted; or
(b) C$_{5-20}$arylene;
and is optionally substituted; or
(c) C$_{5-20}$arylene—C$_{1-7}$alkylene;
C$_{1-7}$alkylene—C$_{5-20}$arylene; or,
C$_{1-7}$alkylene-C$_{5-20}$arylene-C$_{1-7}$alkylene;
and is optionally substituted;
with the proviso that if R$^2$ is C$_{1-7}$alkylene and R$^3$ is C$_{5-20}$arylene, then R$^3$ is not meta-phenylene.

Examples of suitable substituents on C$_{1-7}$alkylene include those described above under the heading "The Acid Leader Group, Q: Substituents." Examples of suitable substituents on C$_{5-20}$arylene include those described above under the heading "Heteroaryl Group Substituents."

In one embodiment, (a) is an aliphatic C$_{1-7}$alkylene group.
In one embodiment, (a) is a saturated C$_{1-7}$alkylene group.
In one embodiment, (a) is a saturated aliphatic C$_{1-7}$alkylene group.
In one embodiment, (a) is —(CH$_2$)$_n$—, wherein n is an integer from 1 to 5.
In one embodiment, (a) is —CH$_2$—, —CH$_2$CH$_2$—, or —CH=CH—.
In one embodiment, (b) is phenylene; and is optionally substituted. In one embodiment, the phenylene is meta or para. In one embodiment, the phenylene is para.
In one embodiment, (c) is phenylene-C$_{1-7}$alkylene; C$_{1-7}$alkylene-phenylene; or, C$_{1-7}$alkylene-phenylene-C$_{1-7}$alkylene; and is optionally substituted. In one embodiment, the phenylene is meta or para. In one embodiment, the phenylene is para.

In one embodiment, each of the ether groups, R$^2$ and R$^3$, is independently (a) C$_{1-7}$alkylene (e.g., as defined above under the heading "The Acid Leader Group, Q"); and is optionally substituted. In one embodiment, one of the ether groups, R$^2$ and R$^3$, is independently (a) C$_{1-7}$alkylene; and is optionally substituted; and the other is as defined herein (with the proviso).

In one embodiment, the group —R$^2$—X—R$^3$— is independently selected from groups of the formulae: —(CH$_2$)$_y$—O—(CH$_2$)$_z$— and —(CH$_2$)$_y$—S—(CH$_2$)$_z$—; wherein each y and each z is independently an integer from 1 to 5 (i.e., 1, 2, 3, 4, or 5).

In one embodiment, each of the ether groups, R$^2$ and R$^3$, is independently (b) C$_{5-20}$arylene; and is optionally substituted. In one embodiment, one of the ether groups, R$^2$ and R$^3$, is independently (b) C$_{5-20}$arylene; and is optionally substituted; and the other is as defined herein. In one embodiment, each of the ether groups, R$^2$ and R$^3$, is independently (b) phenylene; and is optionally substituted. In one embodiment, one of the ether groups, R$^2$ and R$^3$, is independently (b) phenylene; and is optionally substituted; and the other is as defined herein (with the proviso).

In one embodiment, each of the ether groups, R$^2$ and R$^3$, is independently (c) C$_{5-20}$arylene-C$_{1-7}$alkylene; C$_{1-7}$alkylene-C$_{5-20}$arylene; or, C$_{1-7}$alkylene-C$_{5-20}$arylene-C$_{1-7}$alkylene: and is optionally substituted. In one embodiment, one of the ether groups, R$^2$ and R$^3$, is independently (c) C$_{5-20}$arylene-C$_{1-7}$alkylene; C$_{1-7}$alkylene-C$_{5-20}$arylene; or, C$_{1-7}$alkylene-C$_{5-20}$arylene-C$_{1-7}$alkylene; and is optionally substituted; and the other is as defined herein. In one embodiment, each of the ether groups, R$^2$ and R$^3$, is independently (c) phenylene-C$_{1-7}$alkylene; C$_{1-7}$alkylene-phenylene; or, C$_{1-7}$alkylene-phenylene-C$_{1-7}$alkylene; and is optionally substituted. In one embodiment, one of the ether groups, R$^2$ and R$^3$, is independently (c) phenylene-C$_{1-7}$alkylene; C$_{1-7}$alkylene-phenylene; or, C$_{1-7}$alkylene-phenylene-C$_{1-7}$alkylene; and is optionally substituted; and the other is as defined herein.

EXAMPLES OF SPECIFIC EMBODIMENTS

Some individual embodiments of the present invention include the following compounds.

| | | | |
|---|---|---|---|
| 1. | Quinolin-2-yl | 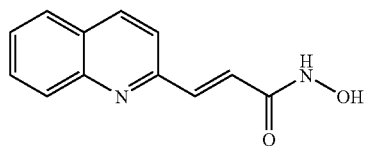 | PX117449 |
| 2. | Quinolin-2-yl | 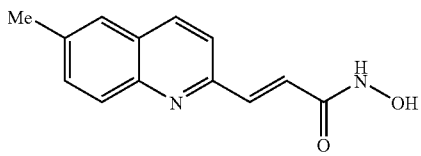 | PX118839 |
| 3. | Quinolin-2-yl | 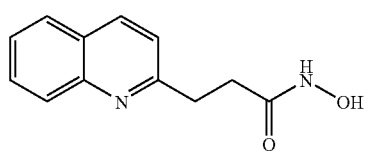 | PX118828 |
| 4. | Quinolin-2-yl | 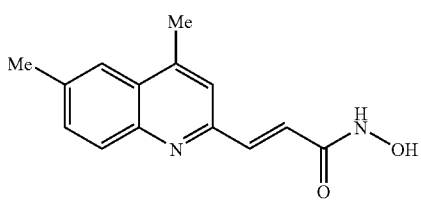 | PX118864 |
| 5. | Quinolin-2-yl | 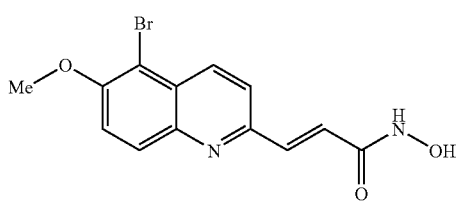 | PX118865 |
| 6. | Quinolin-2-yl | 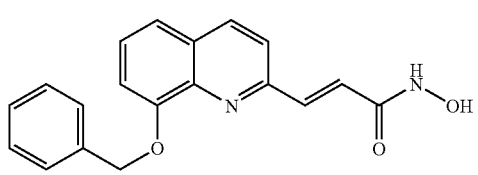 | PX118867 |
| 7. | Quinolin-2-yl | 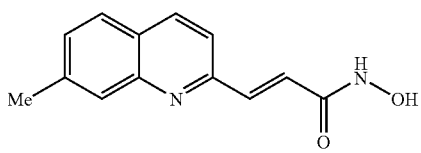 | PX118869 |
| 8. | Quinolin-2-yl | 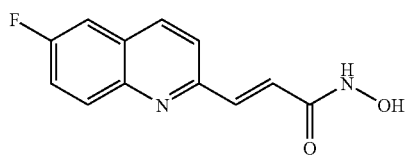 | PX118886 |
| 9. | Quinolin-2-yl | 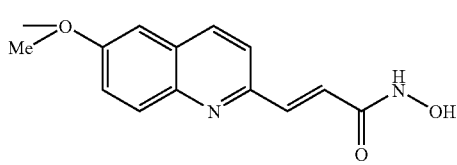 | PX118887 |

-continued
| | | | |
|---|---|---|---|
| 10. | Quinolin-2-yl | 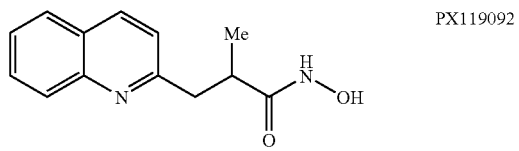 | PX119092 |
| 11. | Quinolin-2-yl | 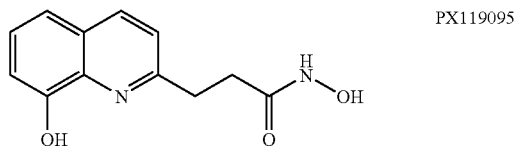 | PX119095 |
| 12. | Quinolin-2-yl | 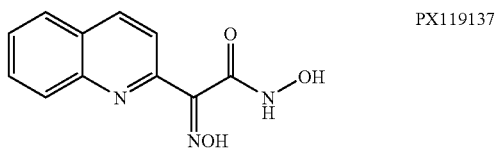 | PX119137 |
| 13. | Quinolin-2-yl | 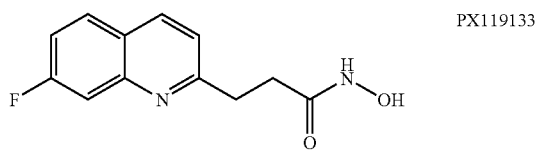 | PX119133 |
| 14. | Quinolin-2-yl | 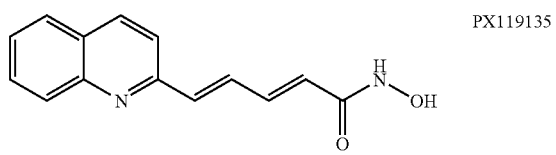 | PX119135 |
| 15. | Quinolin-2-yl | 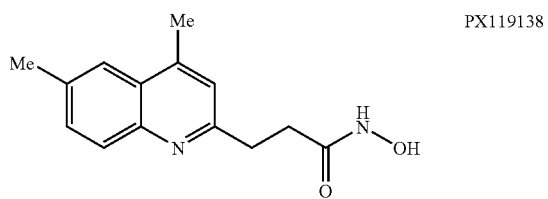 | PX119138 |
| 16. | Quinolin-3-yl | 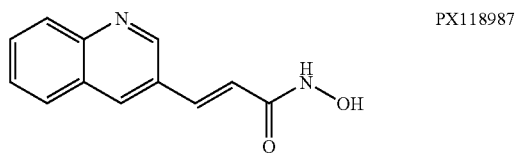 | PX118987 |
| 17. | Quinolin-4-yl | 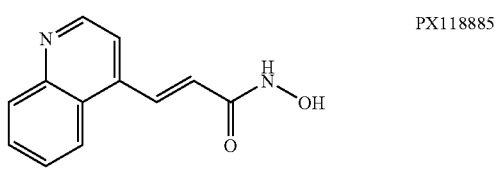 | PX118885 |
| 18. | Quinolin-5-yl | 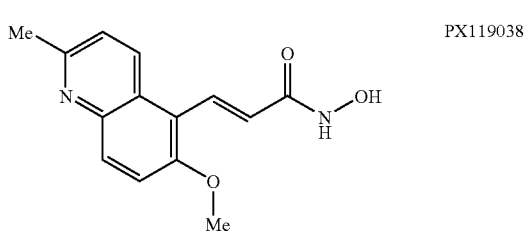 | PX119038 |

-continued
| | | | |
|---|---|---|---|
| 19. | Quinolin-5-yl | 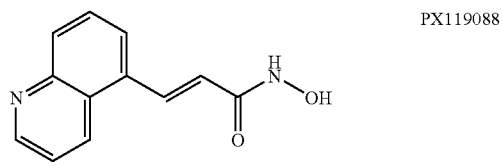 | PX119088 |
| 20. | Quinolin-6-yl | 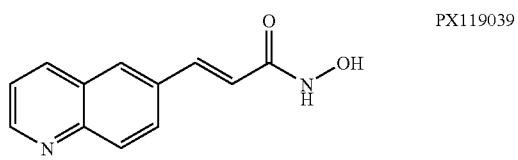 | PX119039 |
| 21. | Quinolin-7-yl | 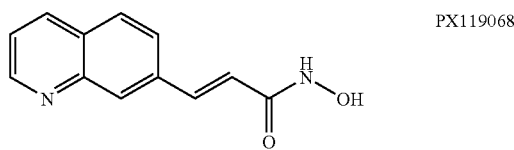 | PX119068 |
| 22. | Quinolin-8-yl | 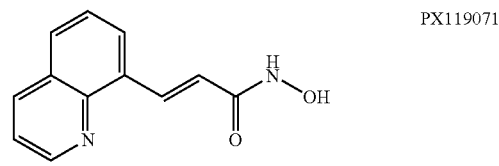 | PX119071 |
| 23. | Quinoxalin-2-yl | 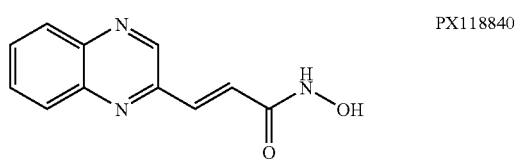 | PX118840 |
| 24. | Quinoxalin-2-yl | 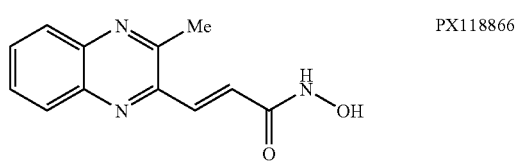 | PX118866 |
| 25. | Quinoxalin-2-yl | 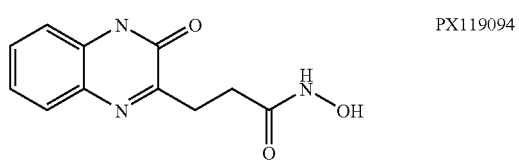 | PX119094 |
| 26. | Benzoxazol-2-yl | 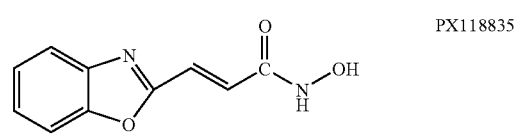 | PX118835 |
| 27. | Benzothiazol-2-yl | 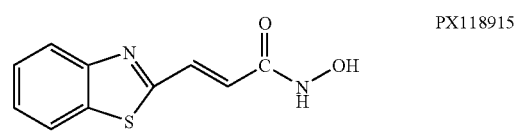 | PX118915 |

| | | |
|---|---|---|
| 28. | Quinolin-2-yl (ether) | 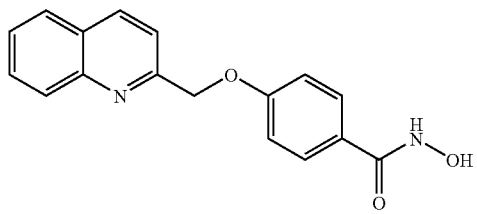 PX119141 |

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/or groups which do not have any carbon-carbon double bonds or carbon-carbon triple bonds.

The term "unsaturated," as used herein, pertains to compounds and/or groups which have at least one carbon-carbon double bond or carbon-carbon triple bond. Examples of unsaturation include partially unsaturated and fully unsaturated.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene), bridged (e.g., as in norbornane), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alkylidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substituents. The term "substituent" is used herein in the conventional sense and refers to a chemical moiety which is covalently attached to, appended to, or if appropriate, fused to, a parent group. A wide variety of substituents are well known, and methods for their formation and introduction into a variety of parent groups are also well known.

The substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated, partially unsaturated, or fully unsaturated. Thus, the term "alkyl" includes the sub-classes alkenyl, alkynyl, cycloalkyl, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Cycloalkyl: The term "cycloalkyl," as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 20 ring atoms (unless otherwise specified). Preferably, each ring has from 3 to 7 ring atoms.

Examples of (unsubstituted) saturated cylcoalkyl groups include, but are not limited to, those derived from: cyclopropane ($C_3$), cyclobutane ($C_4$), cyclopentane ($C_5$), cyclohexane ($C_6$), cycloheptane ($C_7$), norbornane ($C_7$), norpinane ($C_7$), norcarane ($C_7$), adamantane ($C_{10}$), and decalin (decahydronaphthalene) ($C_{10}$).

Examples of (substituted) saturated cycloalkyl groups, which are also referred to herein as "alkyl-cycloalkyl" groups, include, but are not limited to, methylcyclopropyl, dimethylcyclopropyl, methylcyclobutyl, dimethylcyclobutyl, methylcyclopentyl, dimethylcyclopentyl, methylcyclohexyl, and dimethylcyclohexyl, menthane, thujane, carane, pinane, bornane, norcarane, and camphene.

Examples of (substituted) unsaturated cyclic alkenyl groups, which are also referred to herein as "alkyl-cycloalkenyl" groups, include, but are not limited to, methylcyclopropenyl, dimethylcyclopropenyl, methylcyclobutenyl, dimethylcyclobutenyl, methylcyclopentenyl, dimethylcyclopentenyl, methylcyclohexenyl, and dimethylcyclohexenyl.

Examples of (substituted) cycloalkyl groups, with one or more other rings fused to the parent cycloalkyl group, include, but are not limited to, those derived from: indene ($C_9$), indan (e.g., 2,3-dihydro-1H-indene) ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), aceanthrene ($C_{16}$). For example, 2H-inden-2-yl is a $C_5$cycloalkyl group with a substituent (phenyl) fused thereto.

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=$CH_2$), 1-propenyl (—CH=CH—$CH_3$), 2-propenyl (allyl, —CH—CH=$CH_2$), isopropenyl (—C($CH_3$)=$CH_2$), butenyl ($C_4$), pentenyl ($C_5$), and hexenyl ($C_6$).

Examples of (unsubstituted) unsaturated cyclic alkenyl groups, which are also referred to herein as "cycloalkenyl" groups, include, but are not limited to, cyclopropenyl ($C_3$), cyclobutenyl ($C_4$), cyclopentenyl ($C_5$), and cyclohexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —$CH_2$—C≡CH).

Alkylidene: The term "alkylidene," as used herein, pertains to a divalent monodentate moiety obtained by removing two hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidene groups include $C_{1-4}$alkylidene, $C_{1-7}$alkylidene, $C_{1-20}$alkylidene.

Examples of alkylidene groups include, but are not limited to, methylidene (=$CH_2$), ethylidene (=CH—$CH_3$), vinylide (=C=$CH_2$), and isopropylidene (=C($CH_3$)$_2$). An example of a substituted alkylidene is benzylidene (=CH-Ph).

Alkylidyne: The term "alkylidyne," as used herein, pertains to a trivalent monodentate moiety obtained by removing three hydrogen atoms from a carbon atom of a hydrocarbon compound having from 1 to 20 carbon atoms (unless otherwise specified), which may be aliphatic or alicyclic, or a combination thereof, and which may be saturated, partially unsaturated, or fully unsaturated. Examples of groups of alkylidyne groups include $C_{1-4}$alkylidyne, $C_{1-7}$alkylidyne, $C_{1-20}$alkylidyne.

Examples of alkylidyne groups include, but are not limited to, methylidyne (≡CH) and ethylidyne (≡C—$CH_3$).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$carbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{3-7}$-heterocyclyl, $C_{5-7}$-heterocyclyl, and $C_{5-6}$heterocyclyl.

Examples of (non-aromatic) monocyclic heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2;5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahiydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include saccharides, in cyclic form, for-example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{5-20}$, $C_{5-12}$, $C_{5-6}$, $C_{5-7}$ etc.) denote the number of ring atoms, or range of number of ring atoms, whether carbon atoms or heteroatoms. For example, the term "$C_{5-6}$aryl," as used herein, pertains to an aryl group having 5 or 6 ring atoms. Examples of groups of aryl groups include $C_{5-20}$aryl, $C_{5-12}$aryl, $C_{5-7}$aryl, and $C_{5-6}$aryl.

The ring atoms may be all carbon atoms, as in "carboaryl groups" (e.g., $C_{5-20}$carboaryl).

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indene ($C_9$), isoindene ($C_9$), and fluorene ($C_{13}$).

Alternatively, the ring atoms may include one or more heteroatoms, as in "heteroaryl groups" (e.g., $C_{5-20}$heteroaryl).

In this context, the prefixes (e.g., $C_{5-20}$, $C_{5-12}$, $C_{5-7}$, $C_{5-6}$, etc.) denote the number of ring atoms, or range of number of ring atoms, whether carbon atoms or heteroatoms. For example, the term "$C_{9-10}$heteroaryl," as used herein, pertains to a heteroaryl group having 9 or 10 ring atoms. Exampdesof groups of heteroaryl groups include $C_{5-20}$heteroaryl, $C_{5-12}$heteroaryl, $C_{5-7}$heteroaryl, and $C_{5-6}$heteroaryl.

Examples of monocyclic heteroaryl groups include, but are not limited to, those derived from:

$N_1$: pyrrole (azole) ($C_5$), pyridine (azine) ($C_6$);

$O_1$: furan (oxole) ($C_5$);

$S_1$: thiophene (thiole) ($C_5$);

$N_1O_1$: oxazole ($C_5$), isoxazole ($C_5$), isoxazine ($C_6$);

$N_2O_1$: oxadiazole (furazan) ($C_5$);

$N_3O_1$: oxatriazole ($C_5$);

$N_1S_1$: thiazole ($C_5$), isothiazole ($C_5$);

$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);

$N_3$: triazole ($C_5$), triazine ($C_6$); and, $N_4$: tetrazole ($C_5$).

Examples of heterocyclic groups (some of which are also heteroaryl groups) which comprise fused rings, include, but are not limited to:

$C_9$heterocyclic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocyclic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{13}$heterocyclic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$heterocyclic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenothiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methypyrrole. Examples of N-substituents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N⁺(→O-)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms. Monocyclic examples of such groups include, but are not limited to, those derived from:

$C_5$: cyclopentanone, cyclopentenone, cyclopentadienone;

$C_6$: cyclohexanone, cyclohexenone, cyclohexadienone;

$O_1$: furanone ($C_5$), pyrone ($C_6$);

$N_1$: pyrrolidone (pyrrolidinone) ($C_5$), piperidinone (piperidone) ($C_6$), piperidinedione ($C_6$):

$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);

$N_1S_1$: thiazolone ($C_5$), isothiazolone ($C_5$);

$N_1O_1$: oxazolinone ($C_5$).

Polycyclic examples of such groups include, but are not limited to, those derived from:
- $C_9$: indenedione;
- $C_{10}$: tetralone, decalone;
- $C_{14}$: anthrone, phenanthrone;
- $N_1$: oxindole ($C_9$);
- $O_1$: benzopyrone (e.g., coumarin, isocoumarin, chromone) ($C_{10}$);
- $N_1O_1$: benzoxazolinone ($C_9$), benzoxazolinone ($C_{10}$);
- $N_2$: quinazolinedione ($C_{10}$);
- $N_4$: purinone ($C_9$) (e.g., guanine).

Still more examples of cyclic groups which bear one or more oxo (=O) groups on ring carbon atoms include, but are not limited to, those derived from:
- cyclic anhydrides (—C(=O)—O—C(=O)— in a ring), including but not limited to maleic anhydride ($C_5$), succinic anhydride ($C_5$), and glutaric anhydride ($C_6$);
- cyclic carbonates (—O—C(=O)—O— in a ring), such as ethylene carbonate ($C_5$) and 1,2-propylene carbonate ($C_5$);
- imides (—C(=O)—NR—C(=O)— in a ring), including but not limited to, succinimide ($C_5$), maleimide ($C_5$), phthalimide, and glutarimide ($C_6$);
- lactones (cyclic esters, —O—C(=O)— in a ring), including, but not limited to, β-propiolactone, γ-butyrolactone, δ-valerolactone (2-piperidone), and ε-caprolactone;
- lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);
- cyclic carbamates (—O—C(=O)—NR— in a ring), such as 2-oxazolidone ($C_5$);
- cyclic ureas (—NR—C(=O)—NR— in a ring), such as 2-imidazolidone ($C_5$) and pyrimidine-2,4-dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic" acetal group, R$^1$ and R$^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein R$^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where R$^1$ and R$^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where R$^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, =NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Oxycarboyloxy: —OC(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —OC(=O)OCH$_3$, —OC(=O)OCH$_2$CH$_3$, —OC(=O)OC(CH$_3$)$_3$, and —OC(=O)OPh.

Amido (carbamoyl, carbamyl, aminocarbonyl, carboxamide): —C(=O)NR$^1$R$^2$, wherein R$^1$ and R$^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —$NR^1C(=O)R^2$, wherein $R^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and $R^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —$NHC(=O)CH_3$, —$NHC(=O)CH_2CH_3$, and —$NHC(=O)Ph$. $R^1$ and $R^2$ may together form a cyclic structure, as in, for example, succinimidyl, maleimidyl, and phthalimidyl:

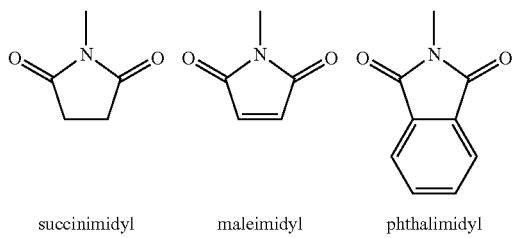

succinimidyl    maleimidyl    phthalimidyl

Aminocarbonyloxy: —$OC(=O)NR^1R^2$, wherein $R^1$ and $R^2$ are independently amino substituents, as defined for amino groups. Examples of aminocarbonyloxy groups include, but are not limited to, —$OC(=O)NH_2$, —$OC(=O)NHMe$, —$OC(=O)NMe_2$, and —$OC(=O)NEt_2$.

Thioamido (thiocarbamyl): —$C(=S)NR^1R^2$, wherein $R^1$ and $R^2$ are independently amino substituents, as defined for amino groups. Examples of amido groups include, but are not limited to, —$C(=S)NH_2$, —$C(=S)NHCH_3$, —$C(=S)N(CH_3)_2$, and —$C(=S)NHCH_2CH_3$.

Ureido: —$N(R^1)CONR^2R^3$ wherein $R^2$ and $R^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —$NHCONH_2$, —$NHCONHMe$, —$NHCONHEt$, —$NHCONMe_2$, —$NHCONEt_2$, —$NMeCONH_2$, —$NMeCONHMe$, —$NMeCONHEt$, —$NMeCONMe_2$, and —$NMeCONEt_2$.

Guanidino: —$NH—C(=NH)NH_2$.

Tetrazolyl: a five membered aromatic ring having four nitrogen atoms and one carbon atom,

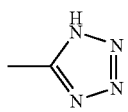

Amino: —$NR^1R^2$, wherein $R^1$ and $R^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—$NH_2$), secondary (—$NHR^1$), or tertiary (—$NHR^1R^2$), and in cationic form, may be quaternary (—$^+NR^1R^2R^3$). Examples of amino groups include, but are not limited to, —$NH_2$, —$NHCH_3$, —$NHC(CH_3)_2$, —$N(CH_3)_2$, —$N(CH_2CH_3)_2$, and —$NHPh$. Examples of cyclic amino groups include, but are not limited to, aziridino, azetidino, pyrrolidino, piperidino, piperazino, morpholino, and thiomorpholino.

Imino: =$NR$, wherein R is an imino substituent, for example, for example, hydrogen, a $C_{1-7}$alkyl group, a $C_{3-20}$heterocyclyl group, or a $C_{5-20}$aryl group, preferably H or a $C_{1-7}$alkyl group. Examples of imino groups include, but are not limited to, =$NH$, =$NMe$, and =$NEt$.

Amidine (amidino): —$C(=NR)NR_2$, wherein each R is an amidine substituent, for example, hydrogen, a $C_{1-7}$alkyl group, a $C_{3-20}$heterocyclyl group, or a $C_{5-20}$aryl group, preferably H or a $C_{1-7}$alkyl group. Examples of amidine groups include, but are not limited to, —$C(=NH)NH_2$, —$C(=NH)NMe_2$, and —$C(=NMe)NMe_2$.

Nitro: —$NO_2$.

Cyano (nitrile, carbonitrile): —CN.

Isocyano: —NC.

Cyanato: —OCN.

Isocyanato: —NCO.

Isothiocyano (isothieeyanato): —NCS.

Sulfhydryl (thiol, mercapto): —SH.

Thioether (sulfide): —SR, wherein R is a thioether substituent, for example, a $C_{1-7}$alkyl group (also referred to as a $C_{1-7}$alkylthio group), a $C_{3-20}$heterocyclyl group, or a $C_{5-20}$aryl group, preferably a $C_{1-7}$alkyl group. Examples of $C_{1-7}$alkylthio groups include, but are not limited to, —$SCH_3$, and —$SCH_2CH_3$.

Disulfide: —SS—R, wherein R is a disulfide substituent, for example, a $C_{1-7}$alkyl group, a $C_{3-20}$heterocyclyl group, or a $C_{5-20}$aryl group, preferably a $C_{1-7}$alkyl group (also referred to herein as $C_{1-7}$alkyl disulfide). Examples of $C_{1-7}$alkyl disulfide groups include, but are not limited to, —$SSCH_3$ and —$SSCH_2CH_3$.

Sulfine (sulfinyl, sulfoxide): —$S(=O)R$, wherein R is a sulfine substituent, for example, a $C_{1-7}$alkyl group, a $C_{3-20}$heterocyclyl group, or a $C_{5-20}$aryl group, preferably a $C_{1-7}$alkyl group. Examples of sulfine groups include, but are not limited to, —$S(=O)CH_3$ and —$S(=O)CH_2CH_3$.

Sulfone (sulfonyl): —$S(=O)_2R$, wherein R is a sulfone substituent, for example, a $C_{1-7}$alkyl group, a $C_{3-20}$heterocyclyl group, or a $C_{5-20}$aryl group, preferably a $C_{1-7}$alkyl group, including, for example, a fluorinated or perfluorinated $C_{1-7}$alkyl group. Examples of sulfone groups include, but are not limited to, —$S(=O)_2CH_3$ (methanesulfonyl, mesyl), —$S(=O)_2CF_3$ (triflyl), —$S(=O)_2CH_2CH_3$ (esyl), —$S(=O)_2C_4F_9$ (nonaflyl), —$S(=O)_2CH_2CF_3$ (tresyl), —$S(=O)_2CH_2CH_2NH_2$ (tauryl), —$S(=O)_2Ph$ (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfinic acid (sulfino): —$S(=O)OH$, —$SO_2H$.

Sulfonic acid (sulfo): —$S(=O)_2OH$, —$SO_3H$.

Sulfinate (sulfinic acid ester): —$S(=O)OR$; wherein R is a sulfinate substituent, for example, a $C_{1-7}$alkyl group, a $C_{3-20}$heterocyclyl group, or a $C_{5-20}$aryl group, preferably a $C_{1-7}$alkyl group. Examples of sulfinate groups include, but are not limited to, —$S(=O)OCH_3$ (methoxysulfinyl; methyl sulfinate) and —$S(=O)OCH_2CH_3$ (ethoxysulfinyl; ethyl sulfinate).

Sulfonate (sulfonic acid ester): —$S(=O)_2OR$, wherein R is a sulfonate substituent, for example, a $C_{1-7}$alkyl group, a $C_{3-20}$heterocyclyl group, or a $C_{5-20}$aryl group, preferably a $C_{1-7}$alkyl group. Examples of sulfonate groups include, but are not limited to, —S(=O)$_2$OCH$_3$ (methoxysulfonyl; methyl sulfonate) and —S(=O)$_2$OCH$_2$CH$_3$ (ethoxysulfonyl; ethyl sulfonate).

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfate: —OS(=O)$_2$OR; wherein R is a sulfate substituent, for example, a C$_{1-7}$alkyl group, a C$_{3-20}$heterocyclyl group, or a C$_{5-20}$aryl group, preferably a C$_{1-7}$alkyl group. Examples of sulfate groups include, but are not limited to, —OS(=O)$_2$OCH$_3$ and —SO(=O)$_2$OCH$_2$CH$_3$.

Sulfamyl (sulfamoyl; sulfinic acid amide; sulfinamide): —S(=O)NR$^1$R$^2$, wherein R$^1$ and R$^2$ are independently amino substituents, as defined for amino groups. Examples of sulfamyl groups include, but are not limited to, —S(=O) NH$_2$, —S(=O)NH(CH$_3$), —S(=O)N(CH$_3$)$_2$, —S(=O)NH (CH$_2$CH$_3$), —S(=O)N(CH$_2$CH$_3$)$_2$, and —S(=O)NHPh.

Sulfonamido (sulfinamoyl; sulfonic acid amide; sulfonamide): —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N (CH$_3$)$_2$, —S(=O)$_2$NH(CH$_2$CH$_3$), —S(=O)$_2$N(CH$_2$CH$_3$)$_2$, and —S(=O)$_2$NHPh.

Sulfamino: —NR$^1$S(=O)$_2$OH, wherein R$^1$ is an amino substituent, as defined for amino groups. Examples of sulfamino groups include, but are not limited to, —NHS(=O)$_2$ OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S (=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

In many cases, substituents may themselves be substituted. For example, a C$_{1-7}$alkyl group may be substituted with, for example, hydroxy (also referred to as a C$_{1-7}$hydroxyalkyl group), C$_{1-7}$alkoxy (also referred to as a C$_{1-7}$alkoxyalkyl group), amino (also referred to as a C$_{1-7}$aminoalkyl group), halo (also referred to as a C$_{1-7}$haloalkyl group), carboxy (also referred to as a C$_{1-7}$carboxyalkyl group), and C$_{5-20}$aryl (also referred to as a C$_{5-20}$aryl-C$_{1-7}$alkyl group).

Similarly, a C$_{5-20}$aryl group may be substituted with, for example, hydroxy (also referred to as a C$_{5-20}$hydroxyaryl group), halo (also referred to as a C$_{5-20}$haloaryl group), amino (also referred to as a C$_{5-20}$aminoaryl group, e.g., as in aniline), C$_{1-7}$alkyl (also referred to as a C$_{1-7}$alkyl-C$_{5-20}$aryl group, e.g., as in toluene), and C$_{1-7}$alkoxy (also referred to as a C$_{1-7}$alkoxy-C$_{5-20}$aryl group, e.g., as in anisole).

These and other specific examples of such substituted-substituents are described below.

Hydroxy-C$_{1-7}$alkyl: The term "hydroxy-C$_{1-7}$alkyl," as used herein, pertains to a C$_{1-7}$alkyl group in which at least one hydrogen atom (e.g., 1, 2, 3) has been replaced with a hydroxy group. Examples of such groups include, but are not limited to, —CH$_2$OH, —CH$_2$CH$_2$OH, and —CH(OH)CH$_2$OH.

Halo-C$_{1-7}$alkyl group: The term "halo-C$_{1-7}$alkyl," as used herein, pertains to a C$_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a C$_{1-7}$perhaloalkyl group." Examples of such groups include, but are not limited to, —CF$_3$, —CHF$_2$, —CH$_2$F, —CCl$_3$, —CBr$_3$, —CH$_2$CH$_2$F, —CH$_2$CHF$_2$, and —CH$_2$CF$_3$.

Amino-C$_{1-7}$alkyl: The term "amino-C$_{1-7}$alkyl," as used herein, pertains to a C$_{1-7}$alkyl group in which at least one hydrogen atom (e.g., 1, 2, 3) has been replaced with an amino group. Examples of such groups include, but are not limited to, —CH$_2$NH$_2$, —CH$_2$CH$_2$NH$_2$, and —CH$_2$CH$_2$N(CH$_3$)$_2$.

Carboxy-C$_{1-7}$alkyl: The term "carboxy-C$_{1-7}$alkyl," as used herein, pertains to a C$_{1-7}$alkyl group in which at least one hydrogen atom (e.g., 1, 2, 3) has been replaced with a carboxy group. Examples of such groups include, but are not limited to, —CH$_2$COOH and —CH$_2$CH$_2$COOH.

C$_{1-7}$alkoxy-C$_{1-7}$alkyl: The term "C$_{1-7}$alkoxy-C$_{1-7}$alkyl," as used herein, pertains to a C$_{1-7}$alkyl group in which at least one hydrogen atom (e.g., 1, 2, 3) has been replaced with a C$_{1-7}$alkoxy group. Examples of such groups include, but are not limited to, —CH$_2$OCH$_3$, —CH$_2$CH$_2$OCH$_3$, and, —CH$_2$CH$_2$OCH$_2$CH$_3$ C$_{5-20}$aryl-C$_{1-7}$alkyl: The term "C$_{5-20}$aryl-C$_{1-7}$alkyl," as used herein, pertains to a C$_{1-7}$alkyl group in which at least one hydrogen atom (e.g., 1, 2, 3) has been replaced with a C$_{5-20}$aryl group. Examples of such groups include, but are not limited to, benzyl (phenylmethyl, PhCH$_2$—), benzhydryl (Ph$_2$CH—), trityl (triphenylmethyl, Ph$_3$C—), phenethyl (phenylethyl, Ph-CH$_2$CH$_2$—), styryl (Ph-CH=CH—), cinnamyl (Ph-CH=CH—CH$_2$—).

Hydroxy-C$_{5-20}$aryl: The term "hydroxy-C$_{5-20}$aryl," as used herein, pertains to a C$_{5-20}$aryl group in which at least one hydrogen atom (e.g., 1, 2, 3) has been substituted with an hydroxy group. Examples of such groups include, but are not limited to, those derived from: phenol, naphthol, pyrocatechol, resorcinol, hydroquinone, pyrogallol, phloroglucinol.

Halo-C$_{5-20}$aryl: The term "halo-C$_{5-20}$aryl," as used herein, pertains to a C$_{5-20}$aryl group in which at least one hydrogen atom (e.g., 1, 2, 3) has been substituted with a halo (e.g., F, Cl, Br, I) group. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

C$_{1-7}$alkyl-C$_{5-20}$aryl. The term "C$_{1-7}$alkyl-C$_{5-20}$aryl," as used herein, pertains to a C$_{5-20}$aryl group in which at least one hydrogen atom (e.g., 1, 2, 3) has been substituted with a C$_{1-7}$alkyl group. Examples of such groups include, but are not limited to, tolyl (from toluene), xylyl (from xylene), mesityl (from mesitylene), and cumenyl (or cumyl, from cumene), and duryl (from durene).

Hydroxy-C$_{1-7}$alkoxy: —OR, wherein R is a hydroxy-C$_{1-7}$ alkyl group. Examples of hydroxy-C$_{1-7}$ailkoxy groups include, but are not limited to, —OCH$_2$OH, —OCH$_2$CH$_2$OH, and —OCH$_2$CH$_2$CH$_2$OH.

Halo-$C_{1-7}$alkoxy: —OR, wherein R is a halo-$C_{1-7}$alkyl group. Examples of halo-$C_{1-7}$alkoxy groups include, but are not limited to, —OCF$_3$, —OCHF$_2$, —OCH$_2$F, —OCCl$_3$, —OCBr$_3$, —OCH$_2$CH$_2$F, —OCH$_2$CHF$_2$, and —OCH$_2$CF$_3$.

Carboxy-$C_{1-7}$alkoxy: —OR, wherein R is a carboxy-$C_{1-7}$alkyl group. Examples of carboxy-$C_{1-7}$alkoxy groups include, but are not limited to, —OCH$_2$COOH, —OCH$_2$CH$_2$COOH, and —OCH$_2$CH$_2$CH$_2$COOH.

$C_{1-7}$alkoxy-$C_{1-7}$alkoxy: —OR, wherein R is a $C_{1-7}$alkoxy-$C_{1-7}$alkyl group. Examples of $C_{1-7}$alkoxy-$C_{1-7}$alkoxy groups include, but are not limited to, —OCH$_2$OCH$_3$, —OCH$_2$CH$_2$OCH$_3$, and —OCH$_2$CH$_2$OCH$_2$CH$_3$.

$C_{5-20}$aryl-$C_{1-7}$alkoxy: —OR, wherein R is a $C_{5-20}$aryl-$C_{1-7}$alkyl group. Examples of such groups include, but are not limited to, benzyloxy, benzhydryloxy, trityloxy, phenethoxy, styryloxy, and cimmamyloxy.

$C_{1-7}$alkyl-$C_{5-20}$aryloxy: —OR, wherein R is a $C_{1-7}$alkyl-$C_{5-20}$aryl group. Examples of such groups include, but are not limited to, tolyloxy, xylyloxy, mesityloxy, cumenyloxy, and duryloxy.

Amino-$C_{1-7}$alkyl-amino: The term "amino-$C_{1-7}$alkyl-amino," as used herein, pertains to an amino group, —NR$^1$R$^2$, in which one of the substituents, R$^1$ or R$^2$, is itself a amino-$C_{1-7}$alkyl group (-$C_{1-7}$alkyl-NR$^3$R$^4$). The amino-$C_{1-7}$alkylamino group may be represented, for example, by the formula —NR$^1$-$C_{1-7}$alkyl-NR$^3$R$^4$. Examples of such groups include, but are not limited to, groups of the formula —NR$^1$(CH$_2$)$_n$NR$^1$R$^2$, where n is 1 to 6 (for example, —NHCH$_2$NH$_2$, —NH(CH$_2$)$_2$NH$_2$, —NH(CH$_2$)$_3$NH$_2$, —NH(CH$_2$)$_4$NH$_2$, —NH(CH$_2$)$_5$NH$_2$, —NH(CH$_2$)$_6$NH$_2$), —NHCH$_2$NH(Me), —NH(CH$_2$)$_2$NH(Me), —NH(CH$_2$)$_3$NH(Me), —NH(CH$_2$)$_4$NH(Me), —NH(CH$_2$)$_5$NH(Me), —NH(CH$_2$)$_6$NH(Me), —NHCH$_2$NH(Et), —NH(CH$_2$)$_2$NH(Et), —NH(CH$_2$)$_3$NH(Et), —NH(CH$_2$)$_4$NH(Et), —NH(CH$_2$)$_5$NH(Et), and —NH(CH$_2$)$_6$NH(Et).

Bidentate Substituents

The term "bidentate substituents," as used herein, pertains to substituents which have two points of covalent attachment, and which act as a linking group between two other moieties.

In some cases (A), a bidentate substituent is covalently bound to a single atom. In some cases (B), a bidentate substituent is covalently bound to two different atoms, and so serves as a linking group therebetween.

(A)

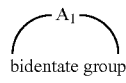
bidentate group (B)

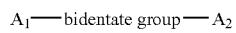
A$_1$——bidentate group——A$_2$

Within (B), in some cases (C), a bidentate substituent is covalently bound to two different atoms, which themselves are not otherwise covalently linked (directly, or via intermediate groups). In some cases (D), a bidentate substituent is covalently bound to two different atoms, which themselves are already covalently linked (directly, or via intermediate groups); in such cases, a cyclic structure results. In some cases, the bidentate group is covalently bound to vicinal atoms, that is, adjacent atoms, in the parent group.

(C)

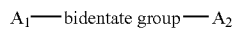
A$_1$——bidentate group——A$_2$ (D)

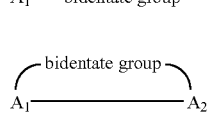

In some cases (A and D), the bidentate group, together with the atom(s) to which it is attached (and any intervening atoms, if present) form an additional cyclic structure. In this way, the bidentate substituent may give rise to a cyclic or polycyclic (e.g., fused, bridged, spiro) structure, which may be aromatic.

Examples of bidentate groups include, but are not limited to, $C_{1-7}$alkylene groups, $C_{3-20}$ heterocyclylene groups, and $C_{5-20}$arylene groups, and substituted forms thereof.

Alkylene

Alkylene: The term "alkylene," as used herein, pertains to a bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkylene," as used herein, pertains to an alkylene group having from 1 to 4 carbon atoms. Examples of groups of alkylene groups include $C_{1-4}$alkylene ("lower alkylene"), $C_{1-7}$alkylene, and $C_{1-20}$alkylene.

Examples of linear saturated $C_{1-7}$alkylene groups include, but are not limited to, —(CH$_2$)$_n$— where n is an integer from 1 to 7, for example, —CH$_2$— (methylene), —CH$_2$CH$_2$— (ethylene), —CH$_2$CH$_2$CH$_2$— (propylene), and —CH$_2$CH$_2$CH$_2$CH$_2$— (butylene).

Examples of branched saturated $C_{2-7}$alkylene groups include, but are not limited to, —CH(CH$_3$)—, —CH(CH$_3$)CH$_2$—, —CH(CH$_3$)CH$_2$CH$_2$—, —CH(CH$_3$)CH$_2$CH$_2$CH$_2$—, —CH$_2$CH(CH$_3$)CH$_2$—, —CH$_2$CH(CH$_3$)CH$_2$CH$_2$—, —CH(CH$_2$CH$_3$)—, —CH(CH$_2$CH$_3$)CH$_2$—, and —CH$_2$CH(CH$_2$CH$_3$)CH$_2$—.

Examples of linear partially unsaturated $C_{2-7}$alkylene groups include, but is not limited to, —CH=CH— (vinylene), —CH=CH—CH$_2$—, —CH=CH—CH$_2$—CH$_2$—, —CH=CH—CH$_2$—CH$_2$—CH$_2$—, —CH=CH—CH=CH—, —CH=CH—CH=CH—CH$_2$—, —CH=CH—CH=CH—CH$_2$—CH$_2$—, —CH=CH—CH$_2$—CH=CH—, and —CH=CH—CH$_2$—CH$_2$—CH=CH—.

Examples of branched partially unsaturated $C_{2-7}$alkylene groups include, but is not limited to, —C(CH$_3$)=CH—, —C(CH$_3$)=CH—CH$_2$—, and —CH=CH—CH(CH$_3$)—.

Examples of alicyclic saturated $C_{3-7}$alkylene groups include, but are not limited to, cyclopentylene (e.g., cyclopent-1,3-ylene), and cyclohexylene (e.g., cyclohex-1,4-ylene).

Examples of alicyclic partially unsaturated $C_{3-7}$alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

Arylene

Arylene: The term "arylene," as used herein, pertains to a bidentate moiety obtained by removing two hydrogen atoms, one from each of two different aromatic ring atoms of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$arylene," as used herein, pertains to an arylene group having 5 or 6 ring atoms. Examples of groups of arylene groups include C$_{3-20}$arylene, C$_{3-12}$arylene, C$_{5-12}$arylene, C$_{5-7}$arylene, and C$_{5-6}$arylene.

The ring atoms may be all carbon atoms, as in "carboarylene groups" (e.g., C$_{5-20}$carboarylene).

Alternatively, the ring atoms may include one or more heteroatoms, as in "heteroarylene groups" (e.g., C$_{5-20}$heteroarylene).

Examples of C$_{5-20}$arylene groups which do not have ring heteroatoms (i.e., C$_{5-20}$carboarylene groups) include, but are not limited to, those derived from the compounds discussed above in regard to carboaryl groups.

Examples of C$_{5-20}$heteroarylene groups include, but are not limited to, those derived from the compounds discussed above in regard to heteroaryl groups.

Includes Other Forms

Unless otherwise specified, included in the above are the well known ionic, salt, solvate, and protected forms of these substituents. For example, a reference to carboxylic acid (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Isomers, Salts, Solvates, Protected Forms, and Prodrugs

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., C$_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

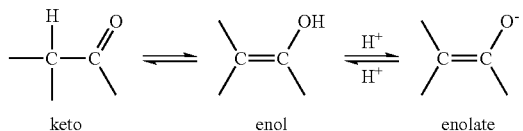

keto      enol      enolate

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e., NH$_4^+$) and substituted ammonium ions (e.g., NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g., —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two non-equivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(=O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(=O)CH$_3$, —OAc).

For example, an aldehyde or ketone group may be protected as an acetal (R—CH(OR)$_2$) or ketal (R$_2$C(OR)$_2$), respectively, in which the carbonyl group (>C=O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl-C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(=O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(=O)OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:

C$_{1-7}$alkyl (e.g., -Me, -Et, -nPr, -iPr, -nBu, -sBu, -iBu, -tBu);
C$_{1-7}$aminoalkyl (e.g., aminoethyl; 2-(N,N-diethylamino) ethyl; 2-(4-morpholino)ethyl); and acyloxy-C$_{1-7}$alkyl (e.g., acyloxymethyl;
acyloxyethyl;
pivaloyloxymethyl;
acetoxymethyl;
1-acetoxyethyl;
1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy) carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound (for example, as in ADEPT, GDEPT, LIDEPT, etc.). For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Synthesis

Methods for the chemical synthesis of compounds of the present invention are described herein. These methods may be modified and/or adapted in known ways in order to facilitate the synthesis of additional compounds within the scope of the present invention.

The compounds of the present invention may be prepared, for example, by the methods described herein, or by adapting these or other well known methods in well known ways.

In one approach, a suitable heteroaryl aldehyde is converted to the corresponding methyl propenoate, using, for example, trimethylphosphono-acetate and sodium hydride. The resulting methyl propenoate is then deprotected to yield the corresponding propenoic acid, for example, by reaction with base. The resulting carboxylic acid is then converted to the corresponding carbamic acid compound, for example, by reaction with oxalyl chloride and hydroxylamine. An example of such a method is illustrated in the following scheme.

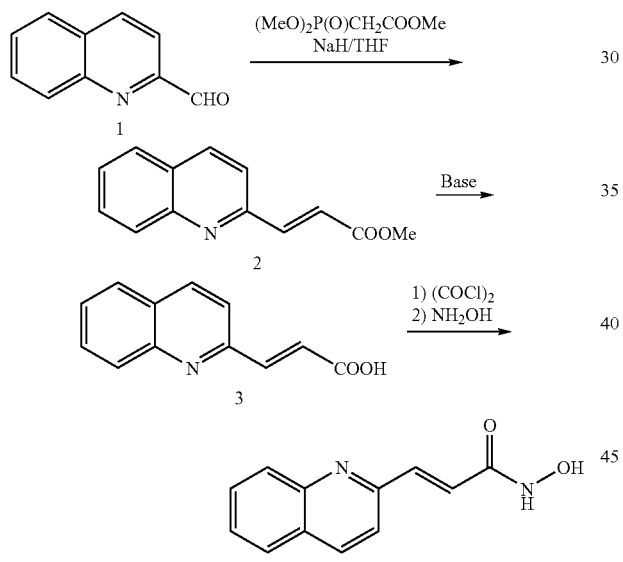

Suitable heteroaryl aldehydes may be, for example, obtained from commercial sources, or synthesized using known methods. For example, quinolin-2-carbaldehyde may be purchased from Acros; 1H-indole-2-carbaldehyde may be prepared from indole-2-carboxlyate (Acros), as described in Franke et al., 1977.

In one approach, a suitable heteroaryl aldehyde compound is converted to the corresponding methyl propenoate, using, for example, trimethylphosphono-acetate and sodium hydride. The resulting methy propenoate is then hydrogenated to yield the corresponding propanoic acid, for example, by reaction with hydrogen and palladium-on-carbon catalyst. The resulting propanoic acid is then converted to the corresponding carbamic acid compound, for example, by reaction with hydroxylamine. An example of such a method is illustrated in the following scheme.

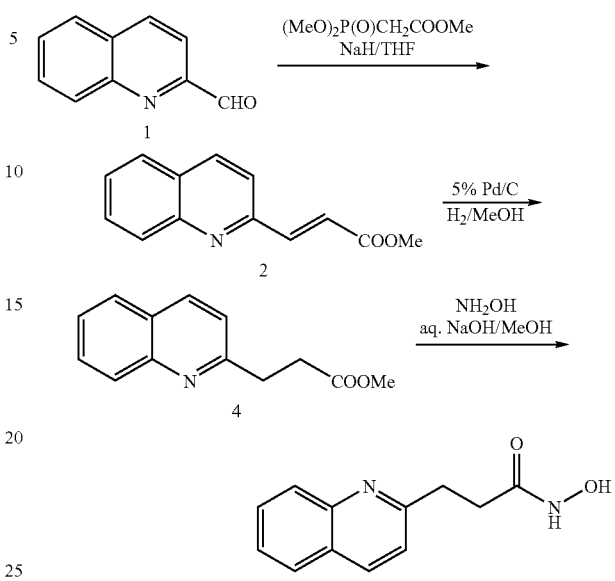

In one approach, a suitable carboxylic acid (e.g., propleric acid) compound is converted to the corresponding acyl halide, e.g., acyl chloride, using, for example, oxalyl chloride. The resulting acyl halide is then converted to the corresponding carbamic acid compound by reaction with hydroxylamine. An example of such a method is illustrated in the following scheme.

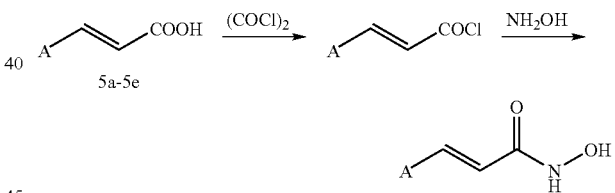

Suitable propenoic acid compounds may be, for example, obtained from commercial sources, or synthesized using known methods. See, for example, Ried et al., 1956.

In one approach, methyl heteroarenes (R—CH$_3$) are converted to the corresponding aldehydes, for example, by reaction with selenium oxide. The aldehydes are then converted to carboxylic acids, for example, by reaction with malonic acid, and then converted to acid halides, for example, by reaction with oxalyl chloride. The acid halides are then converted to carbamic acids, for example, by reaction with NH$_2$OH. An example of such a method is illustrated in the following scheme.

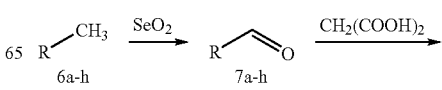

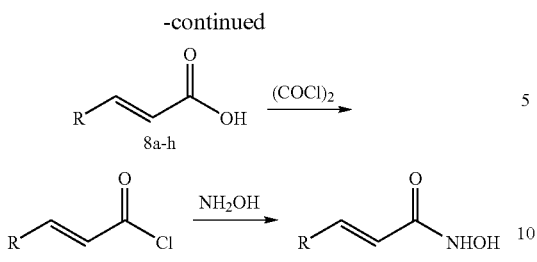

In one approach, heteroaryl-aldehydes are reacted with trimethylphosphonoacetate with tert-butoxide in DMSO to form the corresponding propenoates, which are then deprotected, for example, by reaction with base, to give the carboxylic acids. The acids are then converted to acid halides, for example, by reaction with oxalyl chloride, and then converted to carbamic acids, for example, by reaction with NH$_2$OH. An example of such a method is illustrated in the following scheme.

Scheme 5

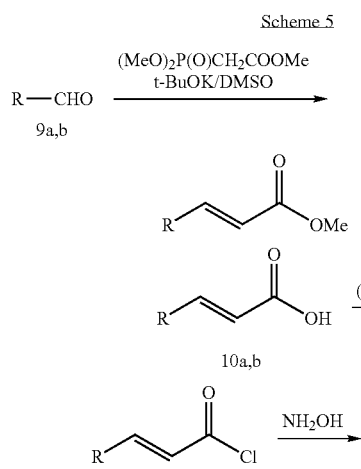

In one approach, a suitable heteroaryl propenoic acid is reduced by reaction with palladium-on-carbon, to form the corresponding heteroaryl propanoic acid, which is then esterified, for example, by reaction with methanol and thionyl chloride, and then converted to the corresponding carbamic acid by reaction with NH$_2$OH. An example of such a method is illustrated in the following scheme.

Scheme 6

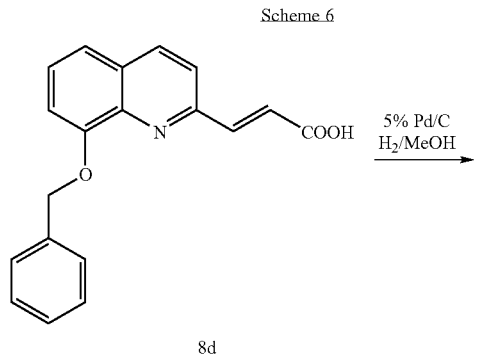

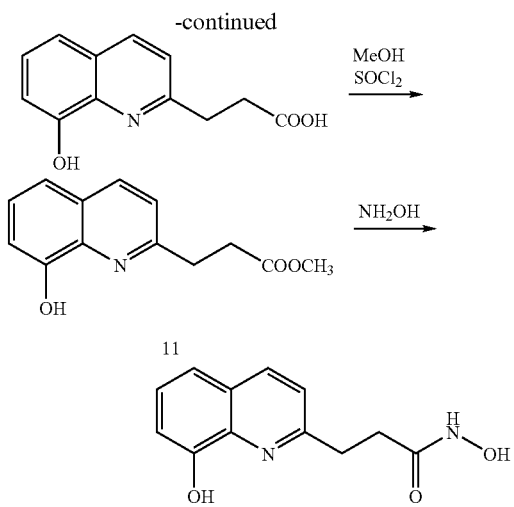

In one approach, a suitable heteroaryl propanoate (e.g., quinoxalineone) is formed, for example, by reaction of 1,2-phenylenediamine with 2-oxopentanedioate. The resulting heteroaryl propanoate is then converted to the corresponding carbamic acid by reaction with NH$_2$OH and NaOMe. An example of such a method is illustrated in the following scheme.

Scheme 7

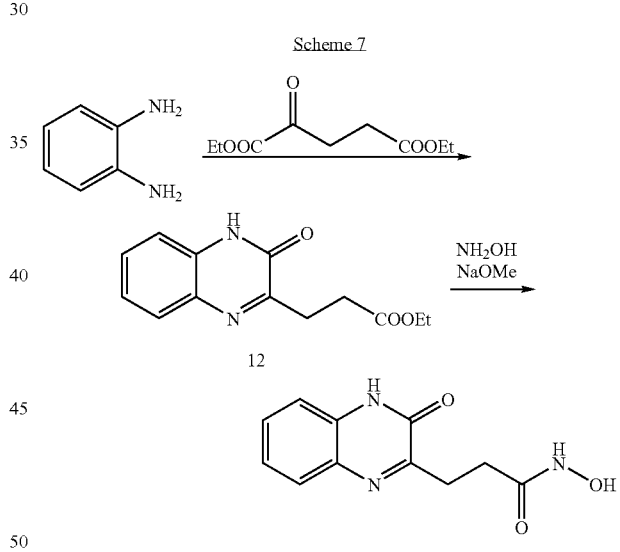

In one approach, a suitable heteroaryl-methyl-halide is reacted with a suitable hydroxy ester, for example, hydroxy benzoate. The resulting ester is converted to the corresponding carbamic acid by reaction with NH$_2$OH and NaOMe/MeOH. An example of such a method is illustrated in the following scheme.

Scheme 8

-continued

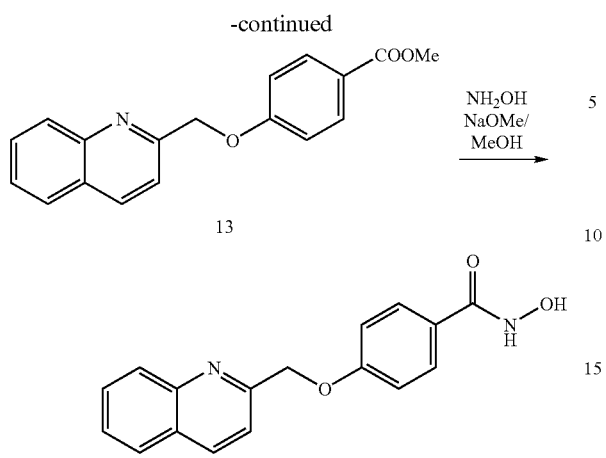

In one approach, a suitable heteroaryl halide is reacted, for example, with methyl acrylate, to form the corresponding heteroaryl propenoate. The ester group is deprotected, for example, by reaction with acid. The resulting carboxylic acid group is then converted to an acid halide group, for example, by reaction with oxalyl chloride. The resulting acid halide group is then converted to a carbamic acid group by reaction with, for example, $NH_2OH$. An example of such a method is illustrated in the following scheme.

Scheme 9

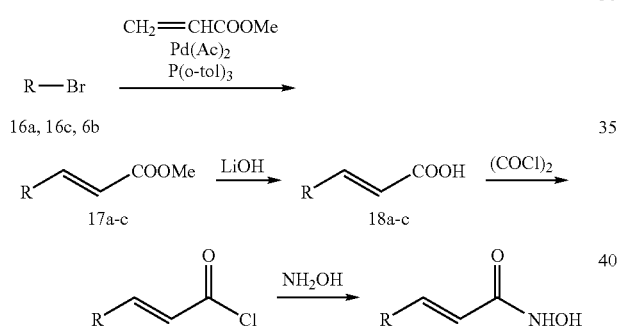

In one approach, a heteroaryl N-oxide, for example, quinoline N-oxide is reacted with, for example, methyl (3-oxobutanoic acid) ester and acetic anhydride, followed by reaction with acid, to give the corresponding heteroaryl-acetic acid methyl ester. This product is then converted to the corresponding hydroxy-imino compound, for example, by reaction with $NaNO_2$ and acetic acid. This product is then converted to the corresponding carbamic acid compound, for example, by reaction with $NH_2OH$ and NaOMe/MeOH. An example of such a method is illustrated in the following scheme.

Scheme 10

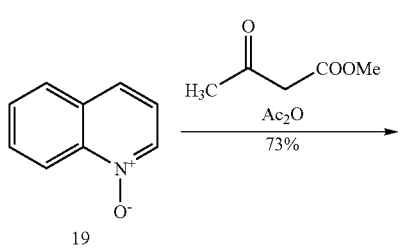

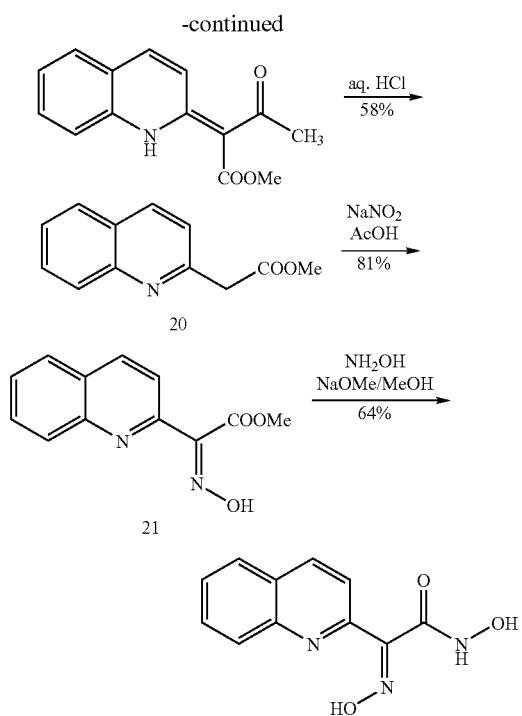

In one approach, a suitable heteroaryl propenoate is first hydrogenated, for example, by reaction with palladium-on-carbon, to give the corresponding heteroaryl propanoate, which is then converted to the corresonding carbamic acid, for example, by reaction with hydroxylamine. An example of such a method is illustrated in the following scheme.

Scheme 11

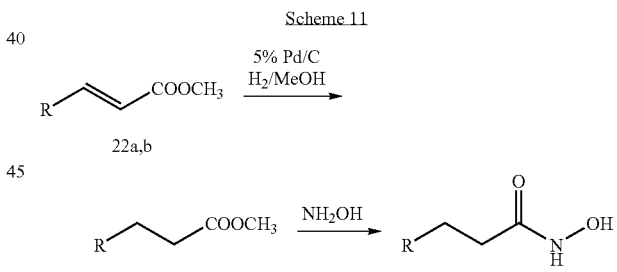

In one approach, a suitable heteroaryl alkenyl aldehyde is reacted with, for example, methyl (triphenylphoranylidene)acetate, and the resulting methyl ester is converted to the corresponding carbamic acid by reaction with, for example, $NH_2OH$. An example of such a method is illustrated in the following scheme.

Scheme 12

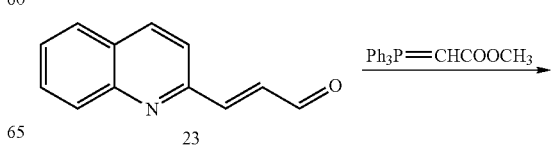

-continued

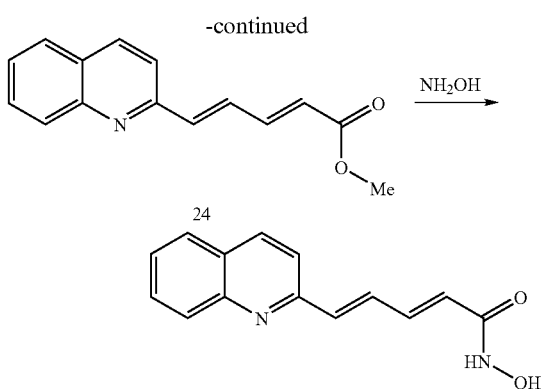

In one approach, a heteroaryl aldehyde is reacted, for example, with triethyl 2-phosphonopropionate and tert-butoxide in DMSO to form a propenoate, which is then reduced, for example, using palladium on carbon, to give the corresponding propanoate, which is then converted to the corresponding carbamic acid, for example, by reaction with NH$_2$OH and NaOMe/MeOH. An example of such a method is illustrated in the following scheme.

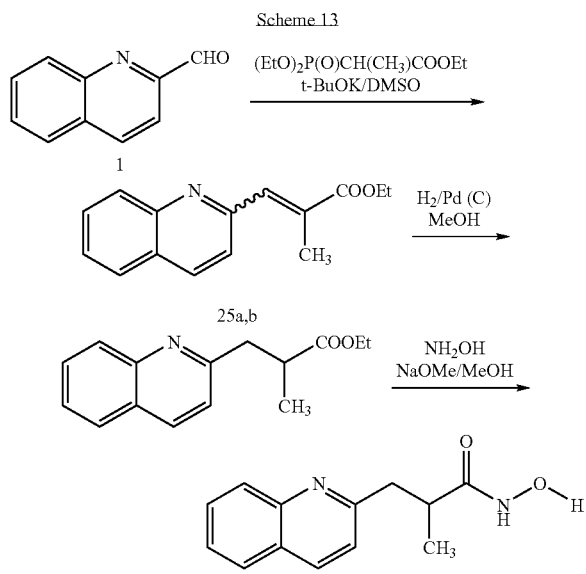

Use

The present invention provides active compounds, specifically, active carbamic acids, as described herein.

The term "active," as used herein, specifically includes both compounds with intrinsic activity (drugs) as well as prodrugs of such compounds, which prodrugs may themselves exhibit little or no intrinsic activity.

The present invention also provides active compounds which inhibit HDAC activity.

The present invention also provides methods of inhibiting HDAC in a cell, comprising contacting said cell with an effective amount of an active compound. Such a method may be practised in vitro or in vivo. In one embodiment, the method is performed in vitro. In one embodiment, the method is performed in vivo. Preferably, the active compound is provided in the form of a pharmaceutically acceptable composition.

The term "inhibiting HDAC," as used herein, includes: inhibiting HDAC activity; inhibiting the formation of HDAC complexes; and inhibiting the activity of HDAC complexes.

One of ordinary skill in the art is readily able to determine whether or not a candidate compound inhibits HDAC activity. For example, one assay which may conveniently be used in order to assess the HDAC inhibition offered by a particular compound is described in the examples below.

The present invention also provides active compounds which (a) regulate (e.g., inhibit) cell proliferation; (b) inhibit cell cycle progression; (c) promote apoptosis; or (d) a combination of one or more of these.

Thus, the present invention also provides methods of (a) regulating (e.g., inhibiting) cell proliferation; (b) inhibiting cell cycle progression; (c) promoting apoptosis; or (d) a combination of one or more of these, in vitro or in vivo, comprising contacting a cell with an effective amount of an active compound, as described herein.

One of ordinary skill in the art is readily able to determine whether or not a candidate compound regulate (e.g., inhibit) cell proliferation, etc. For example, assays which may conveniently be used to assess the activity offered by a particular compound are described in the examples below.

For example, a sample of cells (e.g., from a tumour) may be grown in vitro and an active compound brought into contact with said cells, and the effect of the compound on those cells observed. As an example of "effect," the morphological status of the cells (e.g., alive or dead, etc.) may be determined. Where the active compound is found to exert an influence on the cells, this may be used as a prognostic or diagnostic marker of the efficacy of the compound in methods of treating a patient carrying cells of the same cellular type.

Methods of Treatment, Etc.

The invention further provides methods of treatment, comprising administering to a subject in need of treatment a therapeutically-effective amount of an active compound, preferably in the form of a pharmaceutical composition.

The invention further provides active compounds for use in a method of treatment of the human or animal body by therapy, for example, in the treatment of a condition mediated by HDAC, a condition known to be treated by HDAC inhibitors (such as, e.g., trichostatin A), cancer, a proliferative condition, or other condition as described herein.

The invention further provides the use of an active compound for the manufacture of a medicament, for example, for the treatment of a condition mediated by HDAC, a condition known to be treated by HDAC inhibitors (such as, e.g., trichostatin A), cancer, a proliferative condition, or other condition as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit/risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Active compounds may also be used, as described above, in combination therapies, that is, in conjunction with other agents, for example, cytotoxic agents.

Anti-HDAC Applications

The present invention also provides active compounds which are anti-HDAC agents, and which treat a condition mediated by HDAC.

The term "a condition mediated by HDAC," as used herein pertains to a condition in which HDAC and/or the action of HDAC is important or necessary, e.g., for the onset, progress, expression, etc. of that condition, or a condition which is known to be treated by HDAC inhibitors (such as, e.g., trichostatin A).

Examples of such conditions include, but are not limited to, the following:

Cancer (see, e.g., Vigushin et al., 2001).

Psoriasis (see, e.g., Iavarone et al., 1999).

Fibroproliferative disorders (e.g., liver fibrosis) (see, e.g., Niki et al., 1999; Corneil et al., 1998).

Smooth muscle proliferative disorders (e.g., atherosclerosis, restenosis) (see, e.g., Kimura et al., 1994).

Neurodegenerative diseases (e.g., Alzheimer's, Parkinson's, Huntington's chorea, amyotropic lateral sclerosis, spino-cerebellar degeneration) (see, e.g., Kuusisto et al., 2001; Stefan et al., 2002).

Inflammatory diseases (e.g., osteoarthritis, rheumatoid arthritis) (see, e.g., Dangond et al., 1998; Takahashi et al., 1996).

Diseases involving angiogenesis (e.g., cancer, rheumatoid arthritis, psoriasis, diabetic retinopathy) (see, e.g., Kim et al., 2001).

Haematopoietic disorders (e.g., anaemia, sickle cell anaemia, thalassaeimia) (see, e.g., McCaffrey et al., 1997).

Fungal infections (see, e.g., Bernstein et al., 2000; Tsuji et al., 1976).

Parasitic infections (e.g., malaria, trypanosomiasis, helminthiasis, protozoal infections (see, e.g., Andrews et al., 2000).

Bacterial infections (see, e.g., Onishi et al., 1996).

Viral infections (see, e.g., Chang et al., 2000).

Conditions treatable by immune modulation (e.g., multiple sclerosis, autoimmune diabetes, lupus, atopic dermatitis, allergies, asthma, allergic rhinitis, inflammatory bowel disease; and for improving grafting of transplants) (see, e.g., Dangond et al., 1998; Takahashi et al., 1996).

One of ordinary skill in the art is readily able to determine whether or not a candidate compound treats a condition mediated by HDAC for any particular cell type. For example, assays which may conveniently be used to assess the activity offered by a particular compound are described in the examples below.

Anticancer Applications

The present invention also provides active compounds which are anticancer agents, and treat cancer.

Thus, the present invention also provides methods of treating cancer, comprising administering to a subject in need of treatment a therapeutically-effective amount of an active compound, as described herein, preferably in the form of a pharmaceutical composition.

One of ordinary skill in the art is readily able to determine whether or not a candidate compound treats a cancerous condition for any particular cell type. For example, assays which may conveniently be used to assess the activity offered by a particular compound are described in the examples below.

The term "anticancer agent" as used herein, pertains to a compound which treats a cancer (i.e., a compound which is useful in the treatment of a cancer). The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death). Examples of cancers are discussed below.

Anticroliferative Applications

The present invention also provides active compounds which are antiproliferative agents. The term "antiproliferative agent" as used herein, pertains to a compound which treats a proliferative condition (i.e., a compound which is useful in the treatment of a proliferative condition).

Thus, the present invention also provides methods of treating a proliferative condition, comprising administering to a subject in need of treatment a therapeutically-effective amount of an active compound, as described herein, preferably in the form of a pharmaceutical composition.

One of ordinary skill in the art is readily able to determine whether or not a candidate compound treats a proliferative condition for any particular cell type. For example, assays which may conveniently be used to assess the activity offered by a particular compound are described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

Additional Uses

Active compounds may also be used as cell culture additives to inhibit HDAC, for example, in order to regulate (e.g., inhibit) cell proliferation in vitro.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other HDAC inhibitors, other anticancer agents, other antiproliferative agents, etc.

The compounds of the present invention may also be used in methods of improving protein production by cultured cells (see, e.g., Furukawa et al., 1998).

Routes of Administration

The active compound or pharmaceutical composition comprising the active compound may be administered to a subject by any convenient route of administration, whether systemically/ peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal; intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be an animal, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

In one embodiment, the subject is a human.

Formulations

While it is possible for the active compound to be used (e.g., administered) alone, it is often preferable to present it as a formulation.

Thus, one aspect of the present invention pertains to a composition comprising a compound, as described herein, and a carrier.

In one embodiment, the composition is a pharmaceutical composition (e.g., formulation, preparation, medicament) comprising a compound, as described herein, and a pharmaceutically acceptable carrier.

In one embodiment, the composition is a pharmaceutical composition comprising at least one compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives*, 2nd Edition (eds. M. Ash and I. Ash), 2001 (Synapse Information Resources, Inc., Endicott, N.Y., USA), *Remington's Pharmaceutical Sciences*, 18th edition, Mack Publishing Company, Easton, Pa., 1990; and *Handbook of Pharmaceutical Excipients*, 2nd edition, 1994.

Another aspect of the present invention pertains to methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, lozenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, lozenges, pastilles, as well as patches, adhesive plasters, depots, and reservoirs. Lozenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, lozenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, lozenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 0.1 to about 250 mg per kilogram body weight of the subject per day. Where the active compound is a salt, an ester, an amide, a prodrug, or the like, the amount administered is calculated on the basis of the parent compound and so the actual weight to be used is increased proportionately.

Kits

One aspect of the invention pertains to a kit comprising (a) the active ingredient, preferably provided in a suitable container and/or with suitable packaging; and (b) instructions for use, for example, written instructions on how to administer the active compound, etc.

The written instructions may also include a list of indications for which the active ingredient is a suitable treatment.

EXAMPLES

The following are examples are provided solely to illustrate the present invention and are not intended to limit the scope of the invention, as described herein.

General $^1$H NMR spectra were recorded at ambient temperature with WH-90/DS or Mercury 200 (Varian) spectrometers. The HPLC measurements were performed on a Gilson Model 302 system equipped with a spectrophotometer. Elemental analyses were obtained with a Carlo Erba EA 1108 instrument. Melting points were measured on a "Boëtius" micro melting point apparatus and are uncorrected. Silicagel, 0.035-0.070 mm, (Acros) was employed for column chromatography and Kieselgel 60 F254 TLC plates (Alufolien 20×20, Merck) for TLC. All the solvents were purified before use by routine techniques. To isolate reaction products the solvents were removed by evaporation using a vacuum rotary evaporator, the water bath temperature not exceeding 40° C.

Various reagents were purchased from Sigma-Aldrich (The Old Brickyard, New Road, Gillingham, Dorset, UK), Acros Organics (Janssens Pharmaceuticalaan 3A, 2440 Geel, Belgium), and Lancaster Synthesis Ltd. (Eastgate, White Lund, Morecambe, Lancashire, LA3 3DY, UK).

Example 1

Methyl (E)-3-(2-quinolinyl)-2-propenoate (2)

To a solution of trimethyl phosphonoacetate (3.0 ml, 18.6 mmol) in tetrahydrofuran (40 ml) under argon atmosphere at 0° C., 60% sodium hydride in oil (0.73 g, 18.3 mmol) was added at once and the resulting mixture was stirred at room temperature for 1 hour. To the reaction mixture, a solution of quinolin-2-carbaldehyde (1) (1.0 g, 6.2 mmol) in tetrahydrofuran (40 ml) was added. After stirring for 1 hour at room temperature, the reaction mixture was partitioned between ethyl acetate (150 ml) and 2N HCl (150 ml). The organic layer was separated, washed with water (100 ml), brine (50 ml), and dried (Na$_2$SO$_4$). The solvent was removed in vacuum and the residue was chromatographed on silica gel with chloroform-ethyl acetate (9:1) as eluent to give the title compound (1.07 g, 81%) as oil. $^1$H NMR (DMSO-d$_6$, HMDSO), δ: 3.78 (3H, s); 7.11 (1H, d, J=16.0 Hz); 7.48-8.16 (5H, m); 7.81 (1H, d, J=16.0 Hz); 8.43 (1H, d, J=8.6 Hz).

Example 2

(E)-3-(2-Quinolinyl)-2-propenoic acid (3)

To a solution of methyl (E)-3-(2-quinolinyl)-2-propenoate (2) (1.07 g, 5.02 mmol) in methanol (24 ml), a water solution of 1N NaOH (16 ml, 16.0 mmol) was added and the reaction mixture was stirred at room temperature for 3.5 hours. The mixture was supplemented with water (40 ml) and washed with ethyl acetate (40 ml). The aqueous layer was separated and the pH of the medium was brought to 5. The mixture was extracted with ethyl acetate (3×40 ml) and the combined extracts were dried (Na$_2$SO$_4$). The solvent was evaporated and the residue was dried in vacuum to give the title compound (0.49 g, 49%) as viscous oil. $^1$H NMR (DMSO-d$_6$, HMDSO), δ: 7.02 (1H, d, J=15.7 Hz); 7.52-8.15 (5H, m); 7.75 (1H, d, J=15.7 Hz); 8.42 (1H, d, J=9.0 Hz); 12.69 (1H, br s).

Example 3

(E)-N-Hydroxy-3-(2-quinolinyl)-2-propenamide (PX117449)

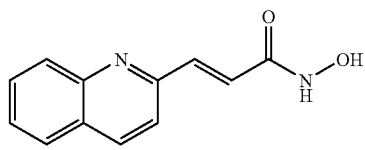

To a solution of (E)-3-(2quinolinyl)-2-propenoic acid L3) (0.4 g, 2.0 mmol) in dry dimethylformamide (3 ml), at ice bath temperature (~0° C.), under an atmosphere of argon, N,N'-carbonyldiimidazole (0.65 g, 4.0 mmol) was added over 15 minutes and the reaction mixture was stirred at this temperature for 2 hours. Triethylamine (0.85 ml, 6.0 mmol), followed by hydroxylamine hydrochloride (0.42 g, 6.0 mmol), were added to the reaction, and the obtained mixture was stirred at ice bath temperature for 1 hour, and then at room temperature overnight. The reaction mixture was poured into water (30 ml), acidified with 1 N HCl to pH 5 and extracted with ethyl acetate (3×40 ml). The combined extracts were washed with water (50 ml), brine (20 ml), and dried ($Na_2SO_4$). The solvent was evaporated and the residue was chromatographed on silica gel with acetonitrile-water (20:1) as eluent to give the title compound as white crystals. M.p. 159.5-160.5° C. $^1H$ NMR (DMSO-$d_6$, HMDSO), δ: 7.12 (1H, d, J=16.0 Hz); 7.49-8.18 (6H, m); 8.44 (1H, d, J=8.0 Hz); 10.13 (2H, br s). HPLC analysis on Symmetry $C_8$ column: impurities 2.0% (column size 3.9×150 mm; mobile phase acetonitrile—0.1M phosphate buffer, pH 2.5, 20:80; detector UV 254 nm; flow rate 1.2 ml/min; sample concentration 0.5 mg/ml). Anal. Calcd for $C_{12}H_{10}N_2O_2 \cdot H_2O$: C, 62.06; H, 5.21; N, 12.06. Found, %: C, 61.95; H, 4.91; N, 12.07.

Example 4

Methyl 3-(2-quinolinyl)propanoate (4)

To a solution of methyl (E)-3-(2-uinolinyl)-2-propenoate L2) (0.26 g 1.22 mmol) in methanol (5 ml), 5% palladium on activated carbon (0.05 g) was added and the resulting suspension was hydrogenated by vigorous stirring for 2 hours at room temperature. The reaction mixture was filtered through a short column of silica gel (ca. 2 g), the column was washed with methanol (3 ml), and the filtrate was evaporated in vacuo. The residue (0.270 g) was chromatographed on silica gel (10 g) with chloroform-ethyl acetate (9:1) as eluent to afford the title compound (0.111 g, 43%) as an oil. $^1H$ NMR ($CDCl_3$, HMDSO), δ: 2.93 (2H, t, J=7.2 Hz); 3.29 (2H, t, J=7.2 Hz); 3.67 (3H, s); 7.29-7.85 (4H, m); 7.89-8.11(2H, m).

Example 5

N-Hydroxy-3-(2-uinolinyl)propanamide (PX118828)

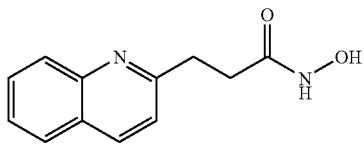

To a solution of methyl 3-(2-quinolinyl)propanoate (4) (0.111 g, 0.52 mmol) and hydroxylamine hydrochloride (0.144 g, 2.07 mmol) in methanol (3 ml), a solution of NaOH (0.165 g, 4.13 mmol) in water (0.5 ml) was added and the resulting mixture was stirred at room temperature for 30 minutes. The pH of the reaction medium was brought to 7 with saturated $KH_2PO_4$, the mixture was extracted with ethyl acetate (3×15 ml), and the combined extracts were dried ($Na_2SO_4$). The solvent was evaporated under reduced pressure, the residue was washed with small amount of ethyl acetate and crystallized from acetonitrile to give the title compound (0.054 g, 48.1%). M.p. 159-160° C. $^1H$ NMR (DMSO-$d_6$, HMDSO), δ: 2.45-2.57(m, 2H, overlapped with a signal of DMSO); 3.15(t, J=7.2 Hz, 2H); 7.44(d, J=8.4 Hz, 1H); 7.54(ddd, J=8.2, 7.6, and 1.2 Hz, 1H); 7.71(ddd, J=8.6, 7.0, and 1.4 Hz, 1H); 7.92(d, J=8.6 Hz, 2H); 8.25(d, J=8.4 Hz, 1H); 8.71 (s, 1H); 10.44(s, 1H). HPLC analysis on Omnispher 5 $C_{18}$: impurities ~2.3% (column size 4.6×150 mm; mobile phase. 5% acetonitrile+95% 0.1M phosphate buffer (pH 2.5); detector UV 230 nm; sample concentration 0.5 mg/ml; flow rate 1.5 ml/min). Anal. Calcd for $C_{12}H_{12}N_2O_2$ containing 2% of inorganic impurities: C, 65.32; H, 5.48; N, 12.70. Found, %: C, 65.42; H, 5.39; N, 12.43.

Method A

To a suspension of (E)-3-(heteroaryl)-2-propenoic acid (1.0 mmol) in methylene chloride (5 ml), oxalyl chloride (0.36 g, 3.0 mmol) and one drop of N,N-dimethylformamide is added. The reaction mixture is stirred for 1 hour at room temperature and concentrated under reduced pressure. The residue is dissolved in tetrahydrofuran (8 ml) and the obtained solution is added to a mixture of hydroxylamine hydrochloride (0.35 g, 5.0 mmol) and a saturated $NaHCO_3$ solution in water (8 ml). The resulting mixture is stirred at room temperature for 0.5 hours, poured into ethyl acetate (50 ml), washed successively with water (2×20 ml), brine (20 ml), and dried ($Na_2SO_4$). The solvent is removed under reduced pressure and the residue is crystallized from a mixture of methanol-acetonitrile to give the desired compound.

Example 6

(E)-3-(1,3-Benzoxazol-2-yl)-N-hydroxy-2-propenamide (PX118835)

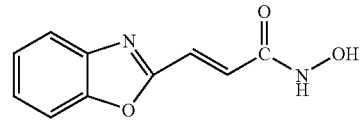

Using Method A, with (E-3-(1,3-benzoxazol-2-yl)-2-propenoic acid (5a), the title compound was obtained (0.13 g, 66%) as a white solid. M. p. 218-220° C. $^1H$ NMR (DMSO-$d_6$, HMDSO), δ: 7.05 (1H, d, J=16.0 Hz, CH); 7.38 (1H, d, J=16.0 Hz, CH); 7.34-7.67 (2H, m, $C_7H_2NO$); 7.67-8.03 (2H, m, $C_7H_2NO$); 9.44 (1H, br s, NH), 11.38 (1H, br s, OH). HPLC analysis on Alltima $C_{18}$: impurities 1.0% (column size 4.6×150 mm; mobile phase acetonitrile—0.1M phosphate buffer (pH 2.5), 30:70 detector UV 254 nm; sample concentration: 0.3 mg/ml). Anal. Calcd for $C_{10}H_8N_2O_3$: C, 58.82; H, 3.95; N, 13.72. Found: C, 58.66; H, 3.83; N, 13.37. (E)-3-(1, 3-Benzoxazol-2-yl)-2-propenoic acid (5a) was prepared from 2-aminophenol using methods as described in the literature (Ried et al., 1956).

Example 7

(E)-3-(6-Methyl-2-uinolinyl)-N-hydroxy-2-propenamide (PX118839)

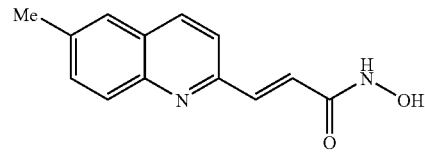

Using Method A, with (E)-3-(6-methyl-2-uinolinyl)-2-propenoic acid (5b), the title compound was obtained, in 77% yield. M.p. 200-202° C. (dec). $^1H$ NMR (DMSO-$d_6$, HMDSO), δ: 2.51 (3H, s, $CH_3$, overlapped with a signal of DMSO); 7.05 (1H, d, J=16.0 Hz, CH); 7.56-7.84 (4H, m, CH, $C_9H_4N$); 7.89 (1H, d, J=8.4 Hz, $C_9HN$); 8.28 (1H, d, J=9.2 Hz, $C_9HN$); 9.22 (1H, s, NH), 10.97 (1H, s, OH). HPLC analysis on Alltima $C_{18}$: impurities 1.0% (column size 4.6× 150 mm; mobile phase acetonitrile—0.1 M phosphate buffer (pH 2.5), 25:75; detector UV 254 nm; sample concentration 0.5 mg/ml). Anal. Calcd for $C_{13}H_{12}N_2O_2 \cdot 0.85H_2O$: C, 64.11; H, 5.67; N, 11.50. Found: C, 63.941 H, 5.56; N, 11.36. (E)-3-(6-methyl-2-quinolinyl)-2-propenoic acid (b) was prepared from 2,6-dimethylquinoline using methods as described in the literature (Ried et al., 1956).

Example 8

(E)-3-(2-Quinoxalinyl)-N-hydroxy-2-propenamide sodium salt (PX118840)

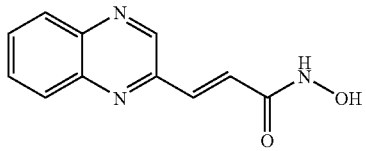

Using Method A, with (E-3-(2-quinoxalinyl)-2-propenoic acid (5c), the title compound was obtained, in 38% yield. M.p. 200-202° C. (dec). $^1$H NMR (DMSO-$d_6$, HMDSO), δ: 7.14 (1H, d, J=15.5 Hz, CH); 7.36 (1H, d, J=15.5 Hz, CH); 7.65-7.92 (2H, m, $C_8H_2N_2$); 7.92-8.25 (2H, m, $C_8H_2N_2$); 9.16 (1H, s, $C_8HN_2$). HPLC analysis on Alltima $C_{18}$: impurities 3.5% (column size 4.6×150 mm; mobile phase acetonitrile—0.2M acetate buffer (pH 5.0), 25:75; detector UV 254 nm; sample concentration 0.2 mg/ml). Anal. Calcd for $C_{11}H_8N_3NaO_2 \cdot C_{11}H_7N_3Na_2O_2 \cdot 1.2H_2O$: C, 48.97; H, 3.70; N, 15.57. Found: C, 48.80; H, 3.62; N, 15.76. (E)-3-(2-uinoxalinyl)-2-propenoic acid (5c) was prepared from 2-methylquinoxaline using methods as described in the literature (Ried et al., 1956).

Example 9

(E)-3-(4-Quinolinyl)-N-hydroxy-2-propenamide (PX118885)

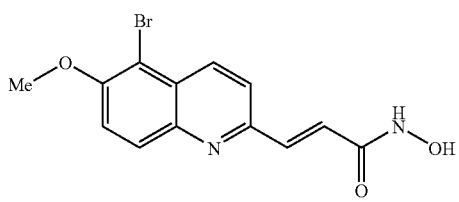

Using Method A, with (E)-3-(4-quinolinyl)-2-propenoic acid (5d), the title compound was obtained, in 51% yield. M.p. 204-206° C. $^1$H NMR (DMSO-$d_6$, HMDSO), δ: 6.73 (1H, d, J=15.8 Hz, CH); 7.62-7.92 (3H, m, $C_9H_3N$); 8.01-8.35 (3H, m, CH, $C_9H_2N$); 8.93 (1H, d, J=4.6 Hz, $C_9HN$); 9.27 (1H, s, NH); 11.05 (1H, s, OH). HPLC analysis on Alltima $C_{18}$: impurities 1.0% (column size 4.6×150 mm; mobile phase acetonitrile—0.1M phosphate buffer (pH 2.5), 30:70; detector UV 220 nm; sample concentration: 0.5 mg/ml). Anal. Calcd for $C_{12}H_{10}N_2O_2$: C, 67.28; H, 4.71; N, 13.08. Found: C, 67.05; H, 4.71; N, 12.95. (E)-3-(4-Quinolinyl)-2-propenoic acid (5d) was synthesized from quinolin-4-carbaldehyde using methods described in the literature (Phillips et al., 1948).

Example 10

(E)-3-(8-Quinolinyl)-N-hydroxy-2-propenamide (PX119071)

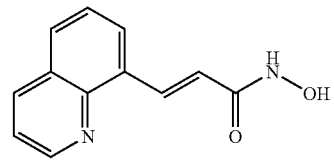

Using Method A, with (E)-3-(8quinolinyl)-2-propenoic acid (5e), the title compound was obtained, in 39% yield. M.p. 159-160° C. $^1$H NMR (DMSO-$d_6$, HMDSO), δ: 6.82 (1H, d, J=16.2 Hz, CH); 7.56-7.77 (2H, m, $C_9H_2N$); 7.98-8.15 (2H, m, $C_9H_2N$); 8.42 (1H, dd, J=1.6 Hz and J=8.4 Hz, $C_9HN$); 8.69 (1H, d, J=16.0 Hz, CH); 9.01 (1H, dd, J=1.8 Hz and J=4.1 Hz, $C_9HN$); 9.14 (1H, br s, NH); 10.91 (1H, s, OH). HPLC analysis on Omnispher 5 $C_{18}$: impurities 1.0% (column size 4.6×150 mm; mobile phase acetonitrile—0.1 M phosphate buffer (pH 2.5), 40:60; detector UV 254 nm; sample concentration 1.0 mg/ml). Anal. Calcd for $C_{12}H_{10}N_2O_2 \cdot 0.25H_2O$: C, 65.90; H, 4.84; N, 12.81. Found: C, 66.51; H, 4.64; N, 12.67. (E)-3-(Quinolin-8-yl)acrylic acid (5e) was prepared from quinoline-8-carbaldehyde using methods described in the literature (Gall et al., 1955).

Example 11

4,6-Dimethyl-2-quinolinecarbaldehyde (7a)

The title compound was prepared from 2,4,6-trimethylquinoline (6a) and selenium dioxide using methods as described in the literature for similar compounds (Mathes et al., 1957) in 61% yield. $^1$H NMR (DMSO-$d_6$, HMDSO), δ: 2.58 (3H, s); 2.72 (3H, s); 7.72 (1H, dd, J=1.8 Hz and J=8.6 Hz); 7.76 (1H, s); 7.92 (1H, unresolved d); 8.09 (1H, d, J=8.6 Hz), 10.05 (1H, s).

Method B

A solution of heteroaryl-carbaldehyde (3.2 mmol), malonic acid (0.44 g, 4.2 mmol), and piperidine (0,1 ml) in pyridine (10 ml) is refluxed for 3 hours. The solvent is removed under reduced pressure, the residue is dissolved in water, and the pH of the medium is brought to 5 by conc. HCl. The precipitate is filtered, washed with water, and dried in vacuo to give the desired compound.

Example 12

(E)-3-(4,6-Dimethyl-2-quinolinyl)-2-propenoic acid (8a)

Using Method B, with 4,6-dimethyl-2-quinolinecarbaldehyde (7a) (0.59 g, 3.2 mmol), the title compound (0.36 g, 54%) was obtained as a white solid. $^1$H NMR (DMSO-$d_6$, HMDSO), δ: 2.55 (3H, s, $CH_3$); 2.73 (3H, s); 7.03 (1H, d, J=15.5 Hz); 7.63 (1H, dd, J=2.0 Hz and J=9.0 Hz); 7.65 (1H, s); 7.74-7.92 (2H, m), 7.91 (1H, d, J=15,5 Hz).

Example 13

(E)-3-(4,6-Dimethyl-2-quinolinyl)-N-hydroxy-2-propenamide (PX118864)

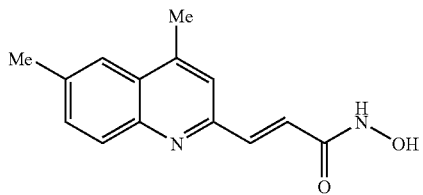

Using Method A, with (E-3-(4,6-dimethyl-2-quinolinyl)-2-propenoic acid (8a), the title compound was obtained, in 42% yield. M.p. 199-201° C. $^1$H NMR (DMSO-$d_6$, HMDSO), δ: 2.51 (3H, s, $CH_3$, overlapped with a signal of DMSO); 2.64 (3H, s, $CH_3$); 7.03 (1H, d, J=15.8 Hz, CH); 7.47-7.70 (3H, m, CH, $C_9H_2N$); 7.81 (1H, s, $C_9HN$); 7.88 (1H, d, J=8.8 Hz, $C_9HN$); 10.10 (2H, br s, NH, OH). HPLC analysis on Omnispher 5 $C_{18}$: impurities 3.5% (column size 4.6×150 mm; mobile phase acetonitrile—0.1 M phosphate buffer (pH 2.5), 25:75; detector UV 254 nm; sample concentration 0.5 mg/ml). Anal. Calcd for $C_{14}H_{14}N_2O_2$*0.2$H_2O$: C, 68.39; H, 5.90; N, 11.39. Found: C, 68.13; H, 5.75; N, 11.34.

Example 14

5-Bromo-6-methoxy-2-quinolinecarbaldehyde (7b)

The title compound was prepared from 5-bromo-6-methoxy-2-methylquinoline (6b) and selenium dioxide using methods as described in the literature for similar compounds (Mathes et al., 1957) in 75% yield. $^1$H NMR (DMSO-$d_6$, HMDSO), δ: 4.07 (3H, s); 7.92 (1H, d, J=9.0 Hz); 8.03 (1H, d, J=9.2 Hz); 8.29 (1H, d, J=9.2 Hz); 8.58 (1H, d, J=9.0 Hz), 10.09 (3H, s).

Example 15

(E)-3-(5-Bromo-6-methoxy-2-quinolinyl)-2-propenoic acid (8b)

Using Method B, with 5-bromo-6-methoxy-2-qinolinecarbaldehyde (7b), the title compound was obtained in 57% yield. $^1$H NMR (DMSO-$d_6$, HMDSO), δ: 4.05 (3H, s); 6.97 (1H, d, J=16.0 Hz); 7.69 (1H, d, J=l16 Hz); 7.78 (1H, d, J=9.0 Hz); 8.01 (1H, d, J=9.2 Hz); 8.09 (1H, d, J=9.0 Hz); 8.45 (1H, d, J=9.0 Hz).

Example 16

(E)-3-(5-Bromo-6-methoxy-2-quinolinyl)-N-hydroxy-2-propenamide (PX118865)

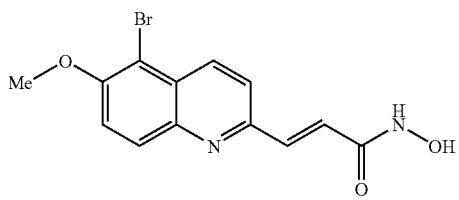

Using Method A, with (E)-3-(5-bromo-6-methoxy-2-quinolinyl)-2-propenoic acid (8b), the title compound was obtained in 26% yield. M.p. 204-206° C. $^1$H NMR (DMSO-$d_6$, HMDSO), δ: 4.03 (3H, s, $CH_3$); 7.04 (1H, d, J=15.8 Hz, CH); 7.63 (1H, d, J=15.8 Hz, CH); 7.81 (1H, d, J=9.2 Hz, $C_9HN$); 7.86 (1H, d, J=9.4 Hz, $C_9HN$); 8.08 (1H, d, J=9;2 Hz, $C_9HN$); 8.47 (1H, d, J=9.4 Hz, $C_9HN$); 10.16 (2H, br s, NH, OH). HPLC analysis on Omnispher 5 $C_{18}$: impurities <1.0% (column size 4.6×150 mm; mobile phase acetonitrile—0.1 M phosphate buffer (pH 2.5), 30:70; detector UV 254 nm; sample concentration 0.5 mg/ml). Anal. Calcd for $C_{13}H_{11}BrN_2O_3$*$(COOH)_2$*0.7$H_2O$: C, 42.31; H, 3.41; N ,6.58. Found: C, 41.96; H, 3.20; N, 6.50.

Example 17

3-Methyl-2-quinoxalinecarbaldehyde (7c)

The title compound was prepared from 2,3-dimethylquinoxaline (6c) and selenium dioxide using methods as described in the literature for similar compounds (Kepez et al., 1989) in 66% yield.

Example 18

(E)-3-(3-Methyl-2-quinoxalinyl)-2-propenoic acid (8c)

Using Method B, with 3-methyl-2-quinoxalinecarbaldehyde (7c), the title compound was obtained in 58% yield. $^1$H NMR (DMSO-$d_6$, HMDSO), δ: 2.77 (3H, s, $CH_3$); 7.18 (1H, d, J=15.8 Hz); 7.50-8.25 (4H, m), 7.85 (1H, d, J=15.8 Hz).

Example 19

(E)-N-Hydroxy-3-(3-methyl-2-quinoxalinyl)-2-propenamide (PX118866)

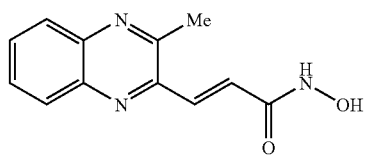

Using Method A, with (E-3-(3-methyl-2-quinoxalinyl)-2-propenoic acid (8c), the title compound was obtained in 33% yield. M.p. 170-172° C. $^1$H NMR (DMSO-$d_6$, HMDSO), δ: 2.75 (3H, s, $CH_3$); 7.13 (1H, d, J=15.6 Hz, CH); 7.56-8.23 (5H, m, CH, $C_8H_4N_2$); 9.23 (1H, br s, NH), 11.07 (1H, br s, OH). HPLC analysis on Alltima $C_{18}$: impurities <1.0% (column size 4.6×150 mm; mobile phase acetonitrile—0.1 M phosphate buffer (pH 2.5), 30:70; detector UV 240 nm; sample concentration 0.5 mg/ml). Anal. Calcd for $C_{12}H_{11}N_3O_2$*0.2 $H_2O$: C, 61.90; H, 4.94; N, 18.05. Found: C, 61.46; H, 4.77; N, 18.07.

Example 20

8-(Benzyloxy)-2-quinolinecarbaldehyde (7d)

The title compound was prepared from 8-hydroxy-2-methylquinoline (6d), benzyl bromide, and selenium dioxide using methods as described in the literature for similar compounds (Buchi et al., 1956) in 35% yield.

Example 21

(E)-3-[8-(Benzyloxy)-2-quinolinyl]-2-propenoic acid (8d)

Using Method B, with 8-(benzyloxy)-2-quinolinecarbaldehyde (7d), the title compound was obtained in 57% yield. $^1$H NMR (DMSO-$d_6$, HMDSO), δ: 5.38 (2H, s); 6.98 (1H, d, J=16.0 Hz); 7.21-7.67 (8H, m); 7.74 (1H, d, J=16.0 Hz); 7.96 (1H, d, J=9.0 Hz; 8.38 (1H, d, J=9.0 Hz).

Example 22

(E)-3-[8-(Benzyloxy)-2-quinolinyl]-N-hydroxy-2-propenamide (PX118867)

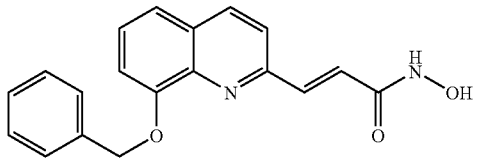

Using Method A, with (E)-3-[8-(benzyloxy)-2-quinolinyl]-2-propenoic acid (8d), the title compound was obtained in 44% yield. M.p. 180-182° C. $^1$H NMR (DMSO-$d_6$, HMDSO), δ: 5.39 (2H, s, $CH_2$); 7.01 (1H, d, J=15.7 Hz, CH); 7.25-7.60 (8H, m, $C_6H_5$, $C_9H_3N$); 7.65 (1H, d, J=15.7 Hz, CH); 7.80 (1H, d, J=8.4 Hz, $C_9HN$); 8.35 (1H, d, J=9.2 Hz, $C_9HN$); 9.18 (1H, s, NH), 11.07 (1H, s, OH). HPLC analysis on Alltima $C_{18}$: impurities 3.0% (column size 4.6×150 mm; mobile phase acetonitrile—0.1M phosphate buffer (pH 2.5), 40:60; detector UV 220 nm; sample concentration 0.5 mg/ml). Anal. Calcd for $C_{19}H_{16}N_2O_3$: C, 71.24, H, 5.03, N, 8.74. Found: C 70.82, H, 5.13, N, 8.51.

Example 23

6-Fluoro-2-quinolinecarbaldehyde (7e)

The title compound was prepared from 6-fluoro-2-methylquinoline (6e) and selenium dioxide using methods as described in the literature for similar compounds (Barbier et al., 2000) in 70% yield.

Example 24

(E)-3-(6-Fluoro-2-quinolinyl)-2-propenoic acid (8e)

Using Method B, with 6-fluoro-2-quinolinecarbaldehyde (7e), the title compound was obtained in 66% yield. $^1$H NMR (DMSO-$d_6$, HMDSO), δ: 7.05 (1H, d, J=16.0 Hz); 7.56-7.89 (2H, m); 7.76 (1H, d, J=16.0 Hz); 8.01 (1H, d, J=8.7 Hz); 8.09 (1H, dd, J=5.5 and 9.5 Hz); 8.43 (1H, d, J=8.7 Hz).

Example 25

(E)-3-(6-Fluoro-2-quinolinyl)-N-hydroxy-2-propenamide (PX118886)

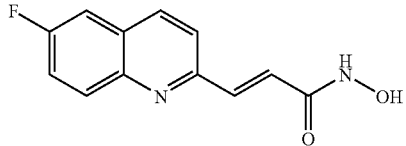

Using Method A, with (E)-3-(6-fluoro-2-quinolinyl)-2-propenoic acid (8e), the title compound was obtained in 50% yield. M.p. 200-202° C. $^1$H NMR (DMSO-$d_6$, HMDSO), δ: 7.05 (1H, d, J=15.5 Hz, CH); 7.47-7.98 (4H, m, CH, $C_9H_3N$); 7.98-8.27 (1H, m, $C_9HN$); 8.43 (1H, d, J=8.6 Hz, $C_9HN$); 10.27 (2H, br s, NH, OH). HPLC analysis on Omnispher 5 $C_{18}$: impurities 1.0% (column size 4.6×150 mm; mobile phase acetonitrile—0.1M phosphate buffer (pH 2.5), 25:75; detector UV 254 nm; sample concentration 0.5 mg/ml).

Anal. Calcd for $C_{12}H_9FN_2O_2$: C, 62.07, H, 3.91, N, 12.06. Found: C 61.88, H 3.90, N 11.95.

Example 26

7-Methyl-2-quinolinecarbaldehyde (7f)

The title compound was prepared from 2,7-dimethylquinoline (6f) and selenium dioxide using methods as described in the literature for similar compounds (Mathes et al., 1957) in 71% yield.

Example 27

(E)-3-(7-Methyl-2-quinolinyl)-2-propenoic acid (8f)

Using Method B, with 7-methyl-2-quinolinecarbaldehyde (7f), the title compound was obtained in 67% yield.

Example 28

(E)-N-Hydroxy-3-(7-methyl-2-quinolinyl)-2-propenamide (PX118869)

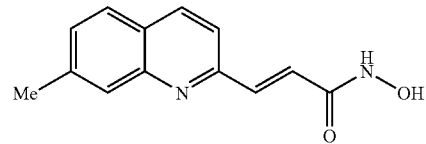

Using Method A, with (E)-3-(7-methyl-2-quinolinyl)-2-propenoic acid (8f), the title compound was obtained 28% yield. M.p. 191-193° C. $^1$H NMR (DMSO-$d_6$, HMDSO), δ: 2.51 (3H, s, $CH_3$, overlapped with a signal of DMSO); 7.06 (1H, d, J=15.6 Hz, CH); 7.47 (1H, d, J=8.2 Hz, $C_9HN$); 7.64 (1H, d, J=15.6 Hz, CH); 7.71 (1H, d, J=8.2 Hz, $C_9HN$); 7.80 (1H, s, $C_9HN$); 7.88 (1H, d, J=8.4 Hz, $C_9HN$); 8.35 (1H, d, J=8.4 Hz, $C_9HN$); 9.21 (1H, s, NH), 11.02 (1H, s, OH). HPLC analysis on Omnispher 5 $C_{18}$: impurities 2.0% (column size 4.6×150 mm; mobile phase acetonitrile—0.1M phosphate buffer (pH 2.5), 20:80; detector UV 220 nm; sample concentration 0.5 mg/ml). Anal. Calcd for $C_{13}H_{12}N_2O_2$: C 68.41, H, 5.30, N 12.27. Found: C 68.72, H, 5.22, N 12.30.

Example 29

6-Methoxy-2-quinolinecarbaldehyde (7g)

The title compound was prepared from 6-methoxy-2-methylquinoline (6g) and selenium dioxide using methods as described in the literature for similar compounds (Mathes et al., 1957) in 68% yield.

Example 30

(E)-3-(6-Methoxy-2-quinolinyl)-2-propenoic acid (8g)

Using Method B, with 6-methoxy-2-quinolinecarbaldehyde (7g), the title compound was obtained in 62% yield.

Example 31

(E)-N-Hydroxy-3-(6-methoxy-2-quinolinyl)-2-propenamide (PX118887)

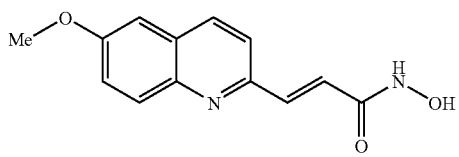

Using Method A, with (E)-3-(6-methoxy-2-quinolinyl)-2-propenoic acid (8g), the title compound was obtained in 52% yield. M.p. 172-175° C. $^1$H NMR (DMSO-$d_6$, HMDSO), δ: 3.89 (3H, s, $CH_3$); 6.99 (1H, d, J=15.5 Hz, CH); 7.25-7.49 (2H, m, $C_9H_2N$); 7.56 (1H, d, J=15.5 Hz, CH); 7.66 (1H, d, J=8.0 Hz, $C_9HN$); 7.92 (1H, d, J=9.5 Hz, $C_9HN$); 8.27 (1H, d, J=8.0 Hz, $C_9HN$); 10.01 (2H, br s, NH, OH). HPLC analysis on Alltima $C_{18}$: impurities 1.3% (column size 4.6×150 mm; mobile phase acetonitrile—0.1 M phosphate buffer (pH 2.5), 20:80; detector UV 220 nm; sample concentration 0.2 mg/ml). Anal. Calcd for $C_{13}H_{12}N_2O_3*0.5H_2O$: C 61.65, H 5.17, N 11.06. Found: C 61.79, H 4.96, N 11.06.

Example 32

1,3-Benzothiazole-2-carbaldehyde (7h)

The title compound was prepared from 2-methyl-1,3-benzothiazole (6h) and selenium dioxide using methods as described in the literature for similar compounds (Conte et al., 1967) in 41% yield.

Example 33

(E)-3-(1,3-Benzothiazol-2-yl)-2-propenoic acid (8h)

Using Method B, with 1,3-benzothiazole-2-carbaldehyde (7h), the title compound was obtained in 52% yield. $^1$H NMR (DMSO-$d_6$, HMDSO), δ: 6.83 (1H, d, J=16.0 Hz); 7.38-7.72 (2H, m); 7.74 (1H, d, J=16.0 Hz); 7.94-8.25 (2H, m).

Example 34

(E)-3-(1,3-Benzothiazol-2-yl)-N-hydroxy-2-propenamide (PX118915)

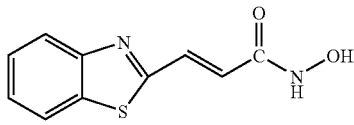

Using Method A, with (E)-3-(1,3-benzothiazol-2-yl)-2-propenoic acid (8h), the title compound was obtained in 42% yield. M.p. 163-165° C. $^1$H NMR (DMSO-$d_6$, HMDSO), δ: 6.96 (1H, d, J=16.0 Hz, CH); 7.27-7.83 (3H, m, CH, $C_7H_2NS$); 7.92-8.41 (2H, m, $C_7H_2NS$); 10.27 (2H, br s, NH, OH). HPLC analysis on Omnispher 5 $C_{18}$: impurities 1% (column size 4.6×150 mm; mobile phase acetonitrile—0.1M phosphate buffer (pH 2.5), 35:65; detector UV 254 nm; sample concentration 0.25 mg/ml). Anal. Calcd for $C_{10}H_8N_2O_2S*0.5H_2O$: C 52.39, H 3.96, N 12.22. Found: C 52.32, H 3.72, N 11.78.

Method C

To a solution of potassium tert-butoxide (0.59 g, 5.3 mmol) in dimethyl sulfoxide (10 ml), trimethyl phosphonoacetate (0.89 g, 4.9 mmol) is added and the resulting solution was stirred for 10 minutes at room temperature. Heteroaryl-carbaldehyde (3.8 mmol) is added to this solution and the obtained mixture is stirred at room temperature for 2 hours. The reaction mixture is poured into water (50 ml) and the product is extracted with diethyl ether (3×50 ml). The extract is washed with water and dried ($Na_2SO_4$). The solvent is removed under reduced pressure, and the product is dissolved in methanol (25 ml) and added to a water solution of 1N LiOH (15 ml, 15.0 mmol). The reaction mixture is stirred at room temperature for 3 hours. Methanol is removed under reduced pressure, the mixture is supplemented with water (20 ml) and washed with ether (40 ml). The aqueous layer is separated and the pH of the medium is brought to 5. The precipitate is filtered, washed with water, and dried to afford the desired product.

Example 35

(E)-3-(7-Quinolinyl)-2-propenoic acid (10a)

Using Method C, with quinoline-7-carbaldehyde (9a) (0.59 g, 3.8 mmol), the title compound was obtained (0.41 g, 55%) as a white solid. $^1$H NMR (DMSO-$d_6$, HMDSO), δ: 6.72 (1H, d, J=16.0 Hz); 7.54 (1H, dd, J=4.2 Hz and J=8.0 Hz); 7.83 (1H, d, J=16.0 Hz); 7.91 (2H, s); 8.85 (1H. s); 8.34 (1H, d, J=8.0 Hz); 8.94 (1H, d, J=1.5 Hz and J=4.0 Hz); 12.47 (1H, br s). Quinoline-7-carbaldehyde (9a) was prepared from 7-methylquinoline using methods described in the literature (Kloc et al., 1984).

Example 36

(E)-N-Hydroxy-3-(7-quinolinyl)-2-propenamide (PX119068)

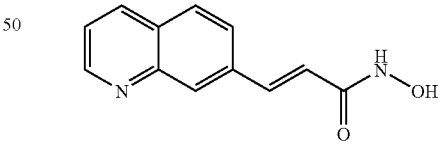

Using Method A, with (E)-3-(7-quinolinyl)-2-propenoic acid (10a), the title compound was obtained in 55% yield. M.p. 203-205° C. $^1$H NMR (DMSO-$d_6$, HMDSO), δ: 6.68 (1H, d, J=15.6 Hz, CH); 7.54 (1H, dd, J=4.0 Hz and J=8.2 Hz, $C_9HN$); 7.69 (1H, d, J=15.8 Hz, CH); 7.81 (1H, d, J=8.2 Hz, $C_9HN$); 8.01 (1H, d, J=8.8 Hz, $C_9HN$); 8.17 (1H, s, $C_9HN$); 8.37 (1H, d, J=7.8 Hz, $C_9HN$); 8.92 (1H, d, J=3.6 Hz, $C_9HN$); 9.16 (1H, s, NH), 10.84 (1H, s, OH). HPLC analysis on Alltima $C_{18}$: impurities 1% (column size 4.6×150 mm; mobile phase acetonitrile—0.1M phosphate buffer (pH 2.5), 20:80; detector UV 254 nm; sample concentration 0.5 mg/ml). Anal. Calcd for $C_{12}H_{10}N_2O_2*0.1H_2O$: C 66.72, H 4.76, N 12.97. Found: C 66.30, H 4.54, N 12.89.

Example 37

(E)-3-(6-Quinolinyl)-2-propenoic acid (10b).

Using Method C, with quinoline-6-carbaldehyde (9b), the title compound was obtained in 71% yield. $^1$H NMR (DMSO-$d_6$, HMDSO), δ: 6.74 (1H, d, J=16.0 Hz); 7.61 (1H, dd, J=4.4 and 8.2 Hz); 7.77 (1H, d, J=16.0 Hz); 7.87-8.56 (4H, m); 8.94 (1H, d, J=4.4 Hz); 12.54 (1H, br s). Quinoline-6-carbaldehyde (9b) was prepared from 6-methylquinoline using methods described in the literature (Kloc et al., 1984).

Example 38

(E)-N-Hydroxy-3-(6-quinolinyl)-2-propenamide (PX119039)

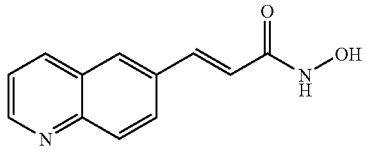

Using Method A, with (E)-3-(6-quinolinyl)-2-propenoic acid (10b), the title compound was obtained in 61% yield. M.p. 125-127° C. $^1$H NMR (DMSO-$d_6$, HMDSO), δ: 6.65 (1H, d, J=15.8 Hz, CH); 7.48-7.65 (1H, m, $C_9$HN); 7.65 (1H, d, J=15.8 Hz, CH); 7.91-8.10 (2H, m, $C_9H_2$N); 8.15 (1H, s, $C_9$HN); 8.38 (1H, d, J=8.4 Hz, $C_9$HN); 8.91 (1H, d, J=2.6 Hz, $C_9$HN); 10.10 (2H, br s, NH, OH). HPLC analysis on Aqueous $C_{18}$: impurities 3.7% (column size 4.6×150 mm; mobile phase acetonitrile—0.1M phosphate buffer (pH 2.5), 7:93; detector UV 230 nm; sample concentration 0.5 mg/ml). Anal. Calcd for $C_{14}H_{14}N_2O_3*0.6H_2O$: C 64.05, H, 5.02, N 12.45. Found: C 64.12, H, 5.02, N 12.09.

Example 39

Methyl 3-(8-hydroxy-2-quinolinyl)propanoate (11)

To a solution of (E)-3-[8-(benzyloxy)-2-quinolinyl]-2-propenoic acid (8d) (0.3 g, 0.98 mmol) in methanol (15 ml), 5% palladium on activated carbon (0.03 g) was added and the resulting suspension was hydrogenated by vigorous stirring for 2 hours at room temperature. The reaction mixture was filtered through a short column of silica gel (ca. 2 g) and the column was washed with methanol (10 ml). To the obtained filtrate, at room temperature, thionyl chloride (0.2 g, 1.7 mmol) was added with vigorous stirring. The reaction mixture was stirred overnight and then evaporated in vacuo. To the residue, a solution of 5% NaHCO$_3$ (20 ml) was added and the mixture was extracted with ethyl acetate (50 ml). The extract was dried (Na$_2$SO$_4$) and evaporated in vacuo. The residue was chromatographed on silica gel with ether-petrol ether (1:2) as eluent to afford the title compound (0.158 g, 70%) as an oil. $^1$H NMR (CDCl$_3$, HMDSO), δ: 2.89 (2H, t, J=7.0 Hz); 3.32 (2H, t, J=7.0 Hz); 3.65 (3H, s); 7.09 (1H, dd, J=2.0 and J=6.0 Hz); 7.16-7.49 (3H, m); 8.01 (1H, d, J=8.6 Hz).

Method D

To a solution of hydroxylamine hydrochloride (0.18 g, 2.6 mmol) in methanol (10 ml), a solution of sodium methylate (3.9 mmol) in methanol (3 ml) is added. The reaction mixture is stirred for 10 minutes and the precipitate is filtered off. To the filtrate, methyl 3-(heteroaryl)-propanoate (11) (0.65 mmol) is added and the solvent is removed under reduced pressure. The residue is dissolved in water (15 ml) and the mixture is acidified with acetic acid. The precipitate is filtered and the obtained solid is crystallized from acetonitrile to give the desired product.

Example 40

N-Hydroxy-3-(8-hydroxy-2-quinolinyl)propanamide (PX119095)

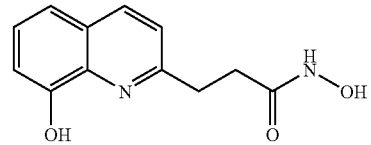

Using Method D, with methyl 3-(8-hydroxy-2-quinolinyl)-propanoate (11) (0.15 g, 0.65 mmol), the title compound was obtained (0.10 g, 66%). M.p. 165-167° C. $^1$H NMR (DMSO-$d_6$, HMDSO), δ: 2.60 (2H, J=7.3 Hz, CH$_2$); 3.19 (2H, J=7.3 Hz, CH$_2$); 7.07 (1H, dd, J=2.4 Hz and J=6.2 Hz, CH); 7.31-7.49 (3H, m, $C_9H_3$N); 8.20 (1H, d, J=8.8 Hz, CH); 8.70 (1H, s, NH), 9.22 (1H, s, OH), 10.46 (1H, s, OH). HPLC analysis on Alltima $C_{18}$: impurities 1% (column size 4.6×150 mm; mobile phase acetonitrile—0.1M phosphate buffer (pH 2.5), 10:90; detector UV 254 nm; sample concentration 1.0 mg/ml). Anal. Calcd for $C_{12}H_{12}N_2O_3$: C 62.06, H, 5.21, N 12.06. Found: C 62.06, H 5.14, N 12.12

Example 41

Ethyl 3-(3-oxo-3,4-dihydro-2-quinoxalinyl)propanoate (12)

The title compound was prepared from 1,2-phenylenediamine and diethyl 2-oxopentanedioate using methods as described in the literature for similar compounds (Weygand et al., 1962) in 72% yield.

Example 42

N-Hydroxy-3-(3-oxo-3,4-dihydro-2-quinoxalinyl) propanamide (PX119094)

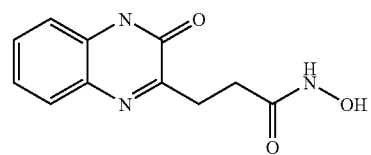

Using Method D, with ethyl 3-(3-oxo-3,4-dihydro-2-quinoxalinyl)propanoate (12), the title compound was obtained in 71% yield. M.p. 213-214° C. $^1$H NMR (DMSO-$d_6$, HMDSO), δ: 2.45 (2H, t, J=7.4 Hz, $CH_2$);); 3.01 (2H, t, J=7.4 Hz, $CH_2$); 7.21-7.36 (2H, m, $C_8H_2N_2$); 7.47 (1H, dt, J=1.2 and 7.6 Hz, $C_8HN_2$); 7.69 (1H, dd, J=1.7 and 8.2 Hz, $C_8HN_2$); 8.72 (1H, s, NH), 10.46 (1H, s, OH), 12.32 (1H, s, NH). HPLC analysis on Omnispher $C_{18}$: impurities 1.5% (column size 4.6×150 mm; mobile phase acetonitrile—0.1M phosphate buffer (pH 2.5), 15:85; detector UV 210 nm; sample concentration 1.0 mg/ml). Anal. Calcd for $C_{11}H_{11}N_3O_3$: C 56.65, H 4.75, N 18.02. Found: C 56.61, H 4.69, N 17.91.

Example 43

Methyl 4-(2-quinolinylmethoxy)benzoate (13)

The title compound was prepared from methyl 4-hydroxybenzoate and 2-chloromethylquinoline using methods as described in the literature for similar compounds (Musser et al., 1990) in 88% yield.

Example 44

N-Hydroxy-4-(2-quinolinylmethoxy)benzamide (PX119141)

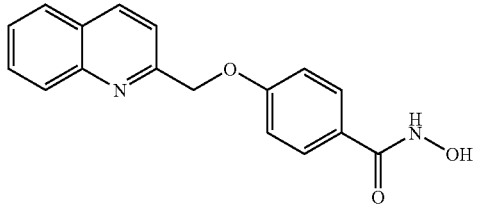

Using Method D, with methyl 4-(2-quinolinylmethoxy)benzoate (13), the title compound was obtained in 51% yield. M.p. 202-204° C. $^1$H NMR (DMSO-$d_6$, HMDSO), δ: 5.43 (2H, s, $CH_2$); 7.12 (2H, d, J=8.8 Hz, $C_6H_2$); 7.62 (1H, t, J=7.7 Hz, $C_9HN$); 7.67 (1H, d, J=8.5 Hz, $C_9HN$); 7.73 (2H, d, J=8.8 Hz, $C_6H_2$); 7.80 (1H, t, J=7.4 Hz, $C_9HN$); 7.99 (1H, d, J=8.2 Hz, $C_9HN$); 8.03 (1H, d, J=7.5 Hz, $C_9HN$); 8.42 (1H, d, J=8.5 Hz, $C_9HN$); 8.93 (1H, s, NH); 11.07 (1H, s, OH). HPLC analysis on Kromasil 100 $C_{18}$: impurities 1% (column size 4.6×150 mm; mobile phase acetonitrile—0.1M phosphate buffer (pH 2.5), 30:70; detector UV 254 nm; sample concentration 0.5 mg/ml). Anal. Calcd for $C_{17}H_{14}N_2O_3*0.1H_2O$: C 68.96, H 4.83, N 9.46. Found: C 68.95, H 4.68, N 9.47.

Example 45

Methyl (E)-3-(3-quinolinyl)-2-propenoate (17a)

The title compound was prepared from 3-bromoquinoline (16a) and methyl acrylate using methods as described in the literature for similar compounds (Frank et al., 1978) in 67% yield.

Method E

To a solution of methyl (E)-3-(heteroaryl)-2-propenoate (3.5 mmol) in methanol (25 ml), a water solution of 1 N LiOH (15 ml, 15.0 mmol) is added, and the reaction mixture is stirred at room temperature until the starting material disappears. The methanol is evaporated, the residue is supplemented with water (20 ml), and washed with diethyl ether (40 ml). The aqueous layer is separated and the pH of the medium is brought to 5 by conc. HCl. The precipitate is filtered, washed with water, and dried to afford the desired compound as a white solid.

Example 46

(E)-3-(3-Quinolinyl)-2-propenoic acid (18a)

Using Method E, with methyl (E)-3-(3-quinolinyl)-2-propenoate (17a) (0.747 g, 3.5 mmol), the title compound was obtained (0.502 g, 72%) as a white solid. $^1$H NMR (DMSO-$d_6$, HMDSO), δ: 6.69 (1H, d, J=16.0 Hz); 7.32-8.05 (4H, m); 7.61 (1H, d, J=16.0 Hz); 8.45 (1H, d, J=1.8 Hz); 8.98 (1H, d, J=1.8 Hz).

Example 47

(E)-N-Hydroxy-3-(3-uinolinyl)-2-propenamide (PX118987)

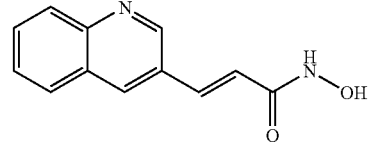

Using Method A, with (E)-3-(3-quinolinyl)-2-propenoic acid (18a), the title compound was obtained in 64% yield. M.p. 205-207° C. $^1$H NMR (DMSO-$d_6$, HMDSO), δ: 6.76 (1H, d, J=16.0 Hz, CH); 7.57-7.87 (3H, m, $C_9H_2N$, CH); 7.94-8.13 (2H, m, $C_9H_2N$); 8.34 (1H, s, $C_9HN$); 9.15 (1H, d, J=1.6 Hz, $C_9HN$); 9.17 (1H, s, NH), 10.89 (1H, s, OH). HPLC analysis on Alltima $C_{18}$: impurities <1% (column size 4.6×150 mm; mobile phase acetonitrile—0.1M phosphate buffer (pH 2.5), 15:85; detector UV 254 nm; sample concentration 0.3 mg/ml). Anal. Calcd for $C_{12}H_{10}N_2O_2$: C 67.28, H 4.71, N 13.08. Found: C 67.26, H 4.68, N 13.13.

Example 48

Methyl (E)-3-(6-methoxy-2-methyl-5-quinolinyl)-2-propenoate (17b)

The title compound was prepared from 5-bromo-6-methoxy-2-methylquinoline (6b) and methyl acrylate using methods as described in the literature for similar compounds (Frank et al., 1978) in 71% yield. $^1$H NMR (DMSO-$d_6$, HMDSO), δ: 2.63 (3H, s); 3.76 (3H, s); 4.01 (3H, s); 6.71 (1H, d, J=15.5 Hz); 7.43 (1H, d, J=8.5 Hz); 7.64 (1H, d, J=8.8 Hz); 8.02 (1H, d, J=8.8 Hz); 8.16 (1H, d, J=15.5 Hz); 8.42 (1H, d, J=8.5 Hz).

Example 49

(E)-3-(6-Methoxy-2-methyl-5-quinolinyl)-2-propenoic acid (18b)

Using Method E, with methyl (E)-3-(6-methoxy-2-methyl-5-quinolinyl)-2-propenoate (17b), the title compound was obtained in 68% yield. $^1$H NMR (DMSO-$d_6$, HMDSO), δ: 2.61 (3H, s); 3.98 (3H, s); 6.49 (1H, d, J=15.5 Hz); 7.38 (1H, d, J=8.2 Hz); 7.65 (1H, d, J=9.0 Hz); 7.81 (1H, d, J=15.5 Hz); 7.94 (1H, d, J=9.0 Hz); 8.44 (1H, d, J=8.2 Hz).

Example 50

(E)-N-Hydroxy-3-(6-methoxy-2-methyl-5-quinolinyl)-2-propenamide (PX119038)

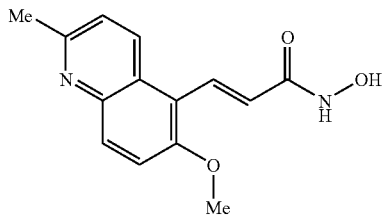

Using Method A, with (E)-3-(6-methoxy-2-methyl-5-quinolinyl)-2-propenoic acid (18b), the title compound was obtained in 58% yield. M.p. 225-227° C. $^1$H NMR (DMSO-$d_6$, HMDSO), δ: 2.62 (3H, s, $CH_3$); 3.99 (3H, s, $CH_3O$); 6.66 (1H, d, J=16.8 Hz, CH); 7.43 (1H, d, J=8.8 Hz, $C_9HN$); 7.67 (1H, d, J=9.4 Hz, $C_9HN$); 7.94 (1H, d, J=16.8 Hz, $C_9HN$); 7.96 (1H, d, J=8.8 Hz, $C_9HN$); 8.40 (1H, d, J=8.8 Hz, $C_9HN$); 9.09 (1H, s, NH); 10.84 (1H, s, OH). HPLC analysis on Alltima $C_{18}$: impurities <1% (column size 4.6×150 mm; mobile phase acetonitrile—0.1M phosphate buffer (pH 2.5), 10:90; detector UV 254 nm; sample concentration 0.5 mg/ml). Anal. Calcd for $C_{14}H_{14}N_2O_3$*0.3$H_2O$: C 63.77, H, 5.58, N 10.62. Found: C 63.81, H 5.61, N 10.33.

Example 51

Methyl (E)-3-(5-quinolinyl)-2-propenoate (17c)

The title compound was prepared from 5-bromoquinoline (16c) and methyl acrylate using methods as described in the literature for similar compounds (Frank et al., 1978). 5-Bromoquinoline (16c) was prepared from quinoline using methods as described in the literature (Gordon et al., 1964).

Example 52

(E)-3-(5-Quinolinyl)-2-propenoic acid (18c)

Using Method E, with methyl (E)-3-(5-quinolinyl)-2-propenoate (17c), the title compound was obtained in 88% yield. $^1$H NMR (DMSO-$d_6$, HMDSO), δ: 6.65 (1H, d, J=15.5 Hz); 7.58 (1H, dd, J=4.0 and 9.0 Hz); 7.38 (1H, d, J=8.2 Hz); 7.78-8.21 (2H, m); 8.32 (1H, d, J=15.5 Hz); 8.65 (1H, d, J=1.8 Hz); 8.94 (1H, dd, J=1.8 and 4.4 Hz).

Example 53

(E)-N-Hydroxy-3-(5-quinolinyl)-2-propenamide (PX119088)

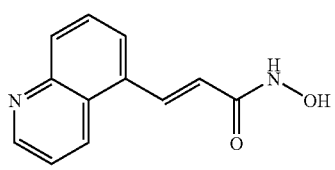

Using Method A, with (E)-3-(5quinolinyl)-2-propenoic acid (18c), the title compound was obtained in 64% yield. M.p. 211-213° C. $^1$H NMR (DMSO-$d_6$, HMDSO), δ: 6.59 (1H, d, J=16.0 Hz, CH); 7.62 (1H, dd, J=4.2 and 8.6 Hz, $C_9HN$); 7.74-7.93 (2H, m, $C_9H_2N$); 8.06 (1H, d, J=8.0 Hz, $C_9HN$); 8.20 (1H, d, J=16.0 Hz, CH); 8.66 (1H, d, J=8.2 Hz, $C_9HN$); 8.96 (1H, dd, J=1.4 and 4.1 Hz, $C_9HN$); 9.18 (1H, br s, NH); 10.90 (1H, br s, OH). HPLC analysis on Omnispher 5 $C_{18}$: impurities 1.6% (column size 4.6×150 mm; mobile phase acetonitrile—0.1M phosphate buffer (pH 2.5), 40:60; detector UV 215 nm; sample concentration 1.0 mg/ml). Anal. Calcd for $C_{12}H_{10}N_2O_2$*0.15$H_2O$: C 66.44, H 4.79. N 12.91. Found: C 66.46, H 4.72, N 12.67.

Example 54

Methyl 2-(2zquinolinyl)acetate (20)

The title compound was prepared from quinoline 1-oxide (19) using methods as described in the literature for similar compounds (Iwao et al., 1978) in 42% yield.

Example 55

Methyl 2-(hydroxyimino)-2-(2-quinolinyl)acetate (21)

The title compound was prepared from methyl 2-(2quinolinyl)acetate (20) using methods as describe in the literature for similar compounds (Kolar et al., 1991) in 81% yield.

Example 56

N-Hydroxy-2-(hydroxyimino)-2-(2-quinolinyl)acetamide (PX119137)

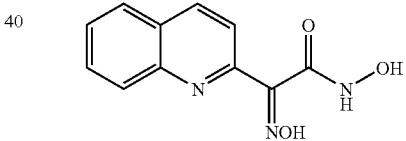

Using Method D, with methyl 2-(hydroxyimino)-2-(2-quinolinyl)acetate (21), the title compound was obtained in 64% yield. M.p. 178-180° C. $^1$H NMR (DMSO-$d_6$, HMDSO), δ: 7.62 (1H, t, J=7.3 Hz, $C_9HN$); 7.78 (1H, t, J=7.5 Hz, $C_9HN$); 7.88-8.07 (3H, m, $C_9H_3N$); 8.37 (1H, d, J=8.6 Hz, $C_9HN$): 9.30 (1H, br s, NH), 11.56 (2H, br s, OH, OH). HPLC analysis on Alltima-$C_{18}$: impurities <1% (column size 4.6×150 mm; mobile phase acetonitrile—0.1 M phosphate buffer (pH 2.5), 15:85; detector UV 210 nm; sample concentration 0.5 mg/ml). Anal. Calcd for $C_{11}H_9N_3O_3$: C 57.14., H, 3.92, N 18.17. Found: C 57.04, H 3.80, N 18.22.

Method F

To a solution of 3-(heteroaryl)propanoic acid (1.58 mmol), in methanol (15 ml), at room temperature, thionyl chloride (0.2 g, 1.7 mmol) is added with vigorous stirring. The reaction mixture is stirred overnight, evaporated in vacuo, and to the mixture a solution of 5% $NaHCO_3$ (20 ml) is added. The precipitate is filtered, washed, and dried in vacuo to give the desired product as a solid.

Example 57

Methyl (E)-3-(6-fluoro-2quinolinyl)-2-propenoate (22a)

Using Method F, with (E)-3-(6-fluoro-2-quinolinyl)-2-propenoic acid (8e), the title compound was obtained. $^1$H NMR (DMSO-d$_6$, HMDSO), δ: 3.73 (3H, s); 7.09 (1H, d, J=16.0 Hz); 7.56-7.93 (3H, m); 7.93-8.25 (2H, m); 8.42 (1H, d, J=8.7 Hz).

Method G

To a solution of methyl (E)-3-(heteroaryl)-2-propenoate (0.87 mmol) in methanol (15 ml), 5% palladium on activated carbon (0.02 g) is added and the resulting suspension is hydrogenated by vigorous stirring at room temperature until the starting compound disappears (ca. 2 hours). The reaction mixture is filtered through a short column of silica gel (ca. 2 g) and the column is washed with methanol (10 ml). To the resulting filtrate, a solution of hydroxylamine prepared from sodium methylate (5.2 mmol) in methanol (3 ml) and hydroxylamine hydrochloride (0.24 g, 3.5 mmol) in methanol (10 ml) is added. Methanol is removed under reduced pressure, and the residue is dissolved in water (15 ml) and acidified with acetic acid. The precipitate is filtered, washed and crystallized from acetonitrile to give the title compound.

Example 58

3-(6-Fluoro-2-quinolinyl)-N-hydroxypropanamide (PX119133)

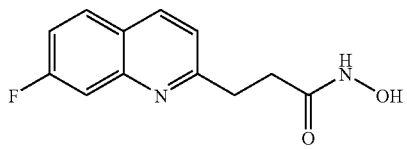

Using Method G, with methyl (E)-3-(6-fluoro-2-quinolinyl)-2-propenoate (22a) (0.2 g, 0.87 mmol), the title compound was obtained (0.10 g, 51%). M.p. 208-210° C. $^1$H NMR (DMSO-d$_6$, HMDSO), δ: 2.50 (2H, t, J=7.5 Hz, CH$_2$, overlapped with a signal of DMSO); 3.15 (2H, t, J=7.5 Hz, CH$_2$); 7.47 (1H d, J=8.7 Hz, C$_9$HN); 7.62 (1H, dt, J=2.9 and 8.9 Hz, C$_9$HN); 7.73 (1H, dd, J=2.9 and 9.4 Hz, C$_9$HN); 7.99 (1H, dd, J=5.5 and 9.1 Hz, C$_9$HN); 8.26 (1H, d, J=8.7 Hz, C$_9$HN); 8.73 (1H, s, NH), 10.44 (1H, s, OH). HPLC analysis on Omnispher 5 C$_{18}$: impurities <1% (column size 4.6×150 mm; mobile phase acetonitrile—0.1M phosphate buffer (pH 2.5), 10:90; detector UV 210 nm; sample concentration 0.33 mg/ml). Anal. Calcd for C$_{12}$H$_{11}$FN$_2$O$_2$: C 61.53, H 4.73, N 11.96. Found: C 61.47, H 4.65, N 11.93.

Example 59

Methyl (E)-3-(4,6-dimethyl-2-quinolinyl)-=2-propenoate (22b)

Using Method F, with (E)-3-(4,6-dimethyl-2-quinolinyl)-2-propenoic acid (8a), the title compound was obtained. $^1$H NMR (DMSO-d$_6$, HMDSO), δ: 2.42-2.59 (3H, s, overlapped with a signal of DMSO); 2.73 (3H, s); 3.76 (3H, s); 7.04 (1H, d, J=16.0 Hz); 7.63 (1H, dd, J=1.8 and 8.4 Hz); 7.65 (1H, s); 7.74-7.92 (2H, m); 7.88 (1H, d, J=16.0 Hz).

Example 60

3-(4,6-Dimethyl-2-qinolinyl)-N-hydroxypropanamide (PX119138)

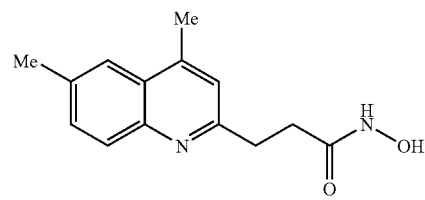

Using Method G, with methyl (E)-3-(4,6-dimethyl-2-quinolinyl)-2-propenoate (22b), the title compound was obtained in 56% yield. TLC: single spot at R$_f$0.45 (methanol-chloroform-acetic acid, 20:80:5), detection—UV-254 nm. M.p. 192-194° C. $^1$H NMR (DMSO-d$_6$, HMDSO), δ: 2.30-2.60 (5H, m, CH$_3$, CH$_2$, overlapped with a signal of DMSO); 2.60 (3H, s, CH$_3$); 3.07 (2H, t, J=7.7 Hz, CH$_2$); 7.23 (1H, s, C$_9$HN); 7.53 (1H, dd, J=1.6 and 8.4 Hz, C$_9$HN); 7.79 (1H, s, C$_9$H$_2$N); 7.81 (1H, d, J=8.4 Hz, C$_9$HN); 8.75 (1H, s, NH); 10.46 (1H, s, OH). Anal. Calcd for C$_{14}$H$_{16}$N$_2$O$_2$*0.1 H$_2$O: C 68.33, H 6.64, N 11.38. Found: C 68.03, H 6.55, N 11.23.

Example 61

(E)-3-(2-Quinolinyl)-2-propenal (23)

The title compound was prepared from quinoline-2-carbaldehyde (1) using methods as described in the literature for similar compounds (Fakhfakh et al., 2002).

Example 62

Methyl (2E,4E)-5-(2-quinolinyl)-2,4-pentadienoate (24)

A solution of (E)-3-(2-quinolinyl)-2-propenal (23) and methyl (triphenylphrophoranylidene) acetate (1.10 g, 3.27 mmol) in benzene (15 ml) was stirred for 6 hours at room temperature. The solvent was evaporated in vacuo and the residue was chromatographed on silica gel with diethyl ether-petrol ether (1:2) as eluent to give the title compound (0.44 g, 56%). $^1$H NMR (DMSO-d$_6$, HMDSO), δ: 3.72 (3H, s); 6.32 (1H, d, J=16.0 Hz); 7.45 (1H, d, J=10.0 Hz); 7.52-7.85 (5H, m); 7.85-7.18 (2H, m); 8.35 (1H, d, J=9.0 Hz).

Example 63

(2E,4E)-N-Hydroxy-5-(2-quinolinyl)-2,4-pentadienamide (PX119135)

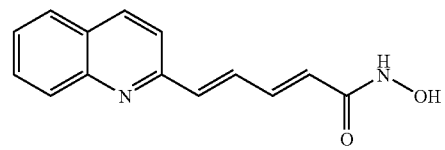

Using Method D, with methyl (2E,4E)-5-(2-quinolinyl)-2,4-pentadienoate (24), the title compound was obtained in 45% yield. M.p. 160-162° C. $^1$H NMR (DMSO-$d_6$, HMDSO), δ: 6.20 (1H, d, J=14.8 Hz, CH); 7.18 (1H, d, J=15.4 Hz, CH); 7.34 (1H, dd, J=11.3 Hz and J=14.8 Hz, CH); 7.47-7.66 (2H, m, CH, C$_9$HN); 7.76 (1H, dt, J=1.0 and 7.5 Hz, C$_9$HN); 8.85 (1H, d, J=8.6 Hz, C$_9$HN); 7.90-8.04 (2H, m, C$_9$H$_2$N); 8.35 (1H, d, J=8.6 Hz, C$_9$HN); 9.92 (2H, br s, NH, OH). HPLC analysis on Alitima C$_{18}$: impurities 2% (column size 4.6×150 mm; mobile phase acetonitrile—0.1 M phosphate buffer (pH 2.5), 15:85; detector UV 210 nm; sample concentration 0.5 mg/ml). Anal. Calcd for C$_{14}$H$_{12}$N$_2$O$_2$: C 69.99, H 5.03, N 11.66. Found: C 69.62, H 5.05, N 11.67.

Example 64

Ethyl (E)-2-methyl-3-(2-quinolinyl)-2-propenoate (25a)

Ethyl (Z)-2-methyl-3-(2-quinolinyl)-2-propenoate (25b)

To a solution of potassium tert-butylate (0.5 g, 4.5 mmol) in dimethyl sulfoxide (10 ml), triethyl 2-phosphonopropionate (0.99 g, 4.2 mmol) was added and the resulting solution was stirred for 10 minutes at room temperature. Quinolin-2-carbaldehyde (1) (0.5 g, 3.2 mmol) was added to this solution, and the resulting mixture was stirred at room temperature for 2 hours. The reaction mixture was poured into water (50 ml) and the product was extracted with diethyl ether (3×50 ml). The extract was washed with water and dried (Na$_2$SO$_4$). The solvent was removed under reduced pressure and isomers of the reaction product were separated on silica gel with acetate—hexane (1:7) as eluent affording the (E)-isomer (25a) (0.59 g, 77%) and the (Z)-isomer (25b) (0.08 g, 10%) as oils. (E)-isomer (25a): $^1$H NMR (DMSO-$d_6$, HMDSO), δ: 1.29 (3H, t, J=7.5 Hz, CH$_3$); 2.41 (3H, d, J=0.9 Hz, CH$_3$); 4.25 (2H, q, J=7.5 Hz, CH$_2$); 7.52-7.92 (4H, m, C$_9$H$_3$N, CH); 7.92-8.12 (2H, m, C$_9$H$_2$N); 8.41 (1H, d, J=9.5Hz, C$_9$H$_2$N). (Z)-isomer (25b): $^1$H NMR (DMSO-$d_6$, HMDSO), δ: 1.05 (3H, t, J=7.0 Hz, CH$_3$); 2.08 (3H, d, J=1.8 Hz, CH$_3$); 4.19 (2H, q, J=7.0 Hz, CH$_2$); 6.83 (1H, q, J=1.8 Hz, CH=); 7.45 (1H, d, J=8.5 Hz, C$_9$HN); 7.49-8.01 (4H, m, C$_9$H$_4$N); 8.27 (1H, d, J=8.5Hz, C$_9$HN).

Example 65

N-Hydroxy-2-methyl-3-(2-quinolinyl)propenamide (PX119092)

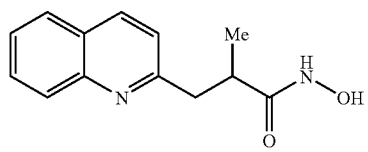

Using Method G, with a mixture of (E) and (Z)-ethyl 2-methyl-3-(2-quinolinyl)2-propenoate (25a,b), the title compound was obtained in 42% yield. M.p. 182-183° C. $^1$H NMR (DMSO-$d_6$, HMDSO), δ: 2.50 (3H, d, J=6.2 Hz, CH$_3$); 2.72-2.98 (2H, m, CH$_2$); 3.08-3.26 (1H, m, CH); 7.38 (1H, d, J=8.2 Hz, C$_9$HN); 7.49-7.62 (1H, m, C$_9$HN); 7.66-7.79 (1H, m, C$_9$HN); 7.88-8.02 (2H, m, C$_9$HN$_2$); 8.25 (1H, d, J=8.8 Hz, C$_9$HN); 8.70 (1H, s, NH), 10.46 (1H, s, OH). HPLC analysis on Omnispher C$_{18}$: impurities <1% (column size 4.6×150 mm; mobile phase acetonitrile—0.1 M phosphate buffer (pH 2.5), 35:65; detector UV 210 nm; sample concentration 1.0 mg/ml). Anal. Calcd for C$_{13}$H$_{14}$N$_2$O$_2$: C 67.81, H 6.13, N 12.17. Found: C 67.81, H 6.15, N 11.99.

Additional compounds falling within the scope of the claims were also prepared and characterised by analogous methods.

Biological Activity

Candidate compounds were assessed for their ability to inhibit deacetylase activity (biochemical assays) and to inhibit cell proliferation (cell-based antiproliferation assays), as described below.

Primary Assay (1): Deacetylase Activity

Briefly, this assay relies on the release of radioactive acetate from a radioactively labelled histone fragment by the action of HDAC enzyme. Test compounds, which inhibit HDAC, reduce the yield of radioactive acetate. Signal (e.g., scintillation counts) measured in the presence and absence of a test compound provide an indication of that compound's ability to inhibit HDAC activity. Decreased activity indicates increased inhibition by the test compound.

The histone fragment was an N-terminal sequence from histone H4, and it was labelled with radioactively labelled acetyl-groups using tritiated acetylcoenzyme A (coA) in conjunction with an enzyme which is the histone acetyltransferase domain of the transcriptional coactivator p300. 0.33 mg of peptide H4 (the N-terminal 20 amino acids of histone H4, synthesized using conventional methods) were incubated with His6-tagged p300 histone acetyltransferase domain (amino acids 1195-1673, expressed in E. coli strain BLR (DE3)pLysS (Novagen, Cat. No. 69451-3) and 3H-acetyl coA (10 μL of 3.95 Ci/mmol; from Amersham) in a total volume of 300 μL of HAT buffer (50 mM TrisCl pH 8, 5% glycerol, 50 mM KCl, 0.1 mM ethylenediaminetetraacetic acid (EDTA), 1 mM dithiothreitol (DTT) and 1 mM 4-(2-aminoethyl)-benzenesulfonylfluoride (AEBSF)). The mixture was incubated at 30° C. for 45 min after which the His-p300 was removed using nickel-trinitriloacetic acid agarose (Qiagen, Cat No. 30210). The acetylated peptide was then separated from free acetyl coA by size exclusion chromatography on Sephadex G-15 (Sigma G-15-120), using distilled H$_2$O as the mobile phase.

After purification of the radiolabelled histone fragment, it was incubated with a source of HDAC (e.g., an extract of HeLa cells (a rich source of HDAC), recombinantly produced HDAC1 or HDAC2) and any released acetate was extracted into an organic phase and quantitatively determined using scintillation counting. By including a test compound with the source of HDAC, that compound's ability to inhibit the HDAC was determined.

Primary Assay (2): Deacetylase Activity: Fluorescent Assay

Alternatively, the activity of the compounds as HDAC inhibitors was determined using a commercially available fluorescent assay kit: (Fluor de Lys™, BioMol Research Labs, Inc., Plymouth Meeting, USA). HeLa extract was incubated for 1 hour at 37° C. in assay buffer (25 mM HEPES, 137 mM NaCl, 2.7 mM KCl, 1 mM MgCl$_2$, pH 8.0) with 15 μM acetylated substrate in the presence of test compound (HDAC inhibitor). The extent of deacetylation was determined by the addition of 50 μL of a 1-in-500 dilution of Developer, and measurement of the fluorescence (excitation 355 nm, emission 460 nm), according to the instructions provided with the kit.

Extensive comparative studies have shown that Primary Assay (1) and Primary Assay (2), discussed above, yield equivalent results. Primary Assay results reported herein are (a) exclusively from (1); (b) exclusively from (2); or (c) from both (1) and (2).

HeLa Cell Extract

The HeLa cell extract was made from HeLa cells (ATCC Ref. No. CCL-2) by freeze-thawing three times in 60 mM TrisCl pH 8.0, 450 mM NaCl, 30% glycerol. Two cell volumes of extraction buffer were used, and particulate material was centrifuged out (20800 g, 4° C., 10 min). The supernatant extract having deacetylase activity was aliquotted and frozen for storage.

Percent activity (% activity) for each test compound was calculated as:

$$\% \text{ activity} = \{(S^c - B)/(S^o - B)\} \times 100$$

wherein $S^c$ denotes signal measured in the presence of enzyme and the compound being tested, $S^o$ denotes signal measured in the presence of enzyme but in the absence of the compound being tested, and B denotes the background signal measured in the absence of both enzyme and compound being tested. The IC50 corresponds to the concentration which achieves 50% activity.

IC50 data for several compounds of the present invention, as determined using this assay, are also shown in Table 1, below.

Measurement of cell viability in the presence of increasing concentration of test compound at different time points is used to assess both cytotoxicity and the effect of the compound on cell proliferation.

Secondary Assay: Cell Proliferation

Compounds with HDAC inhibition activity, as determined using the primary assay, were subsequently evaluated using secondary cell-based assays. The following cell lines were used:

HeLa—Human cervical adenocarcinoma cell line (ATCC ref. No. CCL-2).

K11—HPV E7 transformed human keratinocyte line provided by Pidder Jansen-Duerr, Institut für Biomedizinische Alternsforschung, Innsbruck, Austria.

NHEK-Ad—Primary human adult keratinocyte line (Cambrex Corp., East Rutherford, N.J., USA).

JURKAT—Human T-cell line (ATCC no. TIB-152).

Assay Method

Cells were cultured, exposed to candidate compounds, and incubated for a time, and the number of viable cells was then assessed using the Cell Proliferation Reagent WST-1 from Boehringer Mannheim (Cat. No. 1 644 807), described below.

Cells were plated in 96-well plates at 3-10×10³ cells/well in 100 µL of culture medium. The following day, different concentrations of candidate compounds were added and the cells incubated at 37° C. for 48 h. Subsequently, 10 µL/well of WST-1 reagent was added and the cells reincubated for 1 hour. After the incubation time, absorbance was measured.

WST-1 is a tetrazolium salt which is cleaved to formazan dye by cellular enzymes. An expansion in the number of viable cells results in an increase in the overall activity of mitochondrial dehydrogenases in the sample. This augmentation in the enzyme activity leads to an increase in the amount of formazan dye formed, which directly correlates to the number of metabolically active cells in the culture. The formazan dye produced is quantified by a scanning multiwell spectrophotometer by measuring the absorbance of the dye solution at 450 nm wavelength (reference wavelength 690 nm).

Percent activity (% activity) in reducing the number of viable cells was calculated for each test compound as:

$$\% \text{ activity} = \{(S^c - B)/(S^o - B)\} \times 100$$

wherein $S^c$ denotes signal measured in the presence of the compound being tested, $S^o$ denotes signal measured in the absence of the compound being tested, and B denotes the background signal measured in blank wells containing medium only. The IC50 corresponds to the concentration which achieves 50% activity. IC50 values were calculated using the software package Prism 3.0 (GraphPad Software Inc., San Diego, Calif.), setting top value at 100 and bottom value at 0.

IC50 data for several compounds of the present invention, as determined using this assay, are also shown in Table 2, below.

Measurement of cell viability in the presence of increasing concentration of test compound at different time points is used to assess both cytotoxicity and the effect of the compound on cell proliferation.

Biological Data

IC50 (or percent activity) data for several compounds of the present invention, as determined using the assays described above are summarised in Table 1, below.

TABLE 1

| No. | Ref. | Biochemical Assay Data HDAC Inhibition (IC50) HeLa | Cell-Based Antiproliferation Assay Data Cell Proliferation Inhibition WST-1 (IC50) | | |
|---|---|---|---|---|---|
| | | | HeLa | K11 | Jurkat |
| — | TSA | 5 nM | 350 nM | 0.38 µM | 42 nM |
| — | Oxamflatin | — | — | 4.82 µM | 170 nM |
| — | MS-275 | — | — | 9.16 µM | 365 nM |
| — | SAHA | 189 nM | — | 6.82 µM | 750 nM |
| 1. | PX117449 | 35 nM | 1.8 µM | 12.4 µM | 1.0 µM |
| 2. | PX118839 | 40 nM | 2.4 µM | — | — |
| 3. | PX118828 | 250 nM | 27.2 µM | — | — |
| 4. | PX118864 | 609 nM | 1.3 µM | — | — |
| 5. | PX118865 | 218 nM | 1.4 µM | — | — |
| 6. | PX118867 | 262 nM | 3.9 µM | — | — |
| 7. | PX118869 | 38 nM | 1.5 µM | — | — |
| 8. | PX118886 | 44 nM | 2.6 µM | — | — |
| 9. | PX118887 | 28 nM | 1.8 µM | — | — |
| 10. | PX119092 | — | — | — | — |
| 11. | PX119095 | — | 22.3 □M | — | — |
| 12. | PX119137 | — | — | — | — |
| 13. | PX119133 | 1000 nM | — | — | — |
| 14. | PX119135 | 330 nM | — | — | — |
| 15. | PX119138 | 619 nM | — | — | — |
| 16. | PX118987 | 197 nM | 3.7 µM | — | — |
| 17. | PX118885 | 68 nM | 2.7 | — | — |
| 18. | PX119038 | — | — | — | — |
| 19. | PX119088 | — | 17.8 µM | — | — |
| 20. | PX119039 | 265 nM | 14.1 | — | — |
| 21. | PX119068 | 111 nM | 6.7 µM | — | — |
| 22. | PX119071 | — | — | — | — |
| 23. | PX118840 | 42 nM | 2.1 µM | — | — |
| 24. | PX118866 | — | 33.1 µM | — | — |
| 25. | PX119094 | — | — | — | — |
| 26. | PX118835 | 32 nM | 1.7 µM | — | — |
| 27. | PX118915 | 30 nM | 7.2 µM | — | — |
| 28. | PX119141 | 186 nM | — | — | — |

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention as defined by the appended claims.

REFERENCES

A number of patents and publications are cited herein in order to more fully describe and disclose the invention and the state of the art to which the invention pertains. Full citations for these references are provided herein. Each of these references is incorporated herein by reference in its entirety into the present disclosure.

Andrews et al., 2000, *Int. J. Parasitol.*, Vol. 30, No. 6, pp. 761-768.

Babichev et al., 1968, "Benzo-2-thiazolyl)alkane(arene) carboxylic acids and their derivatives. VII. Hydrazides, hydroxamic acids, nitriles and thioamides from (benzo-2-thiazolyl)alkanecarboxylic acids," *Ukrainskii Khimicheskii Zhurnal*, Vol. 34, No. 9, pp. 933-936.

Bair et al., 2002, "Deacetylase Inhibitors," published international (PCT) patent application number WO 02/22577, published 21 Mar. 2002.

Barbier C., Arnaud J., Commercon A., Riou J. F., Huet F., 2000, *Heterocycles*, Vol. 5, p. 37.

Baxter, A. D., et al., 2000, "Preparation of hydroxamic and carboxylic acid derivatives for treating conditions associated with matrix metalloprotease, ADAM or ADAM-TS enzymes," published international (PCT) patent application number WO 00/069827, published 23 Nov. 2000.

Bernhard, D. et al., 1999, "Apoptosis induced by the histone deacetylase inhibitor sodium butyrate in human leukemic lymphoblasts," *FASEB J.*, Vol. 13, No. 14, pp. 1991-2001.

Bernstein et al., 2000, *Proc. Natl. Acad. Sci. USA*, Vol. 97, No. 25, pp. 13708-13713.

Brehm, A., et al., 1998, "Retinoblastoma protein recruits histone deacetylase to repress transcription," *Nature*, 1998, Vol. 391, pp. 597-601.

Buchi J., Achi A., Deflorin A., Hurni H., 1956, *Helv. Chim. Acta*, Vol. 39, p. 1676.

Buchwald, S. L., et al., 2000a, *J. Org. Chem.*, Vol. 65, p. 1144;

Buchwald, S. L., et al., 2000b, *J. Org. Chem.*, Vol. 65, p. 1158;

Buchwald, S. L., et al., 2001, *J. Org. Chem.*, Vol. 66, p. 3820;

Chang et al., 2000, *Nucleic Acids Res.*, Vol. 28, No. 20, pp. 3918-3925.

Conte, M., 1967, *Bull. Soc. Chim. Fr., p.* 2834.

Corneil et al., 1998, published Japanese patent application, publication number JP 10114681 A2.

Dangond et al., 1998, *Biochem. Biophys. Res. Commun.*, Vol. 242, No. 3, pp. 648-652.

David, G., et al., 1998, *Oncogene*, Vol.16(19), pp. 2549-2556.

Davie, J. R., 1998, "Covalent modifications of histones: expression from chromatic templates," *Curr. Opin. Genet. Dev.*, Vol. 8, pp. 173-178.

Desai et al., 1999, *Proc. AACR*, Vol. 40, abstract #2396.

Emiliani, S., et al., 1998, "Characterization of a human RPD3 ortholog, HDAC3," *Proc. Natl. Acad. Sci. USA*, Vol. 95, p. 2795-2800.

Fauran, C., et al., 1974, "Pharmaceutical 4,8-dimethoxy-furo[3,2-f]benzoxazole-2-acetohydroxamic acid," German Patent Application No. DE 1974-2404413.

Fakhfakh M. A., Franck X., Fournet A., Hocquemiller R., Figadere B., 2002, *Synth. Commun.*, Vol. 32, p. 2863.

Finnin et al., 1999, *Nature*, Vol. 401, pp. 188-193.

Fort, Y. et al., 2001, *Tetrahedron*, Vol. 57, p. 7657.

Franke, U., Roder. E., 1977, "Synthese von 3-(2-lndoly)-acrylsaurederivaten,"Arch. Pharm. (Weinheim), Vol. 310, pp. 975-979.

Frank W. C., Kim Y. C., Heck R. F., 1978, *J. Org. Chem.*, Vol. 43, p. 2247.

Furukawa et al., 1998, U.S. Pat. No. 5,834,249, "Process for production of protein," 10 Nov. 1998.

Gall R., Erlenmeyer H., 1955, *Helv. Chim. Acta*, Vol. 38, p. 1422.

Geerts et al., 1998, European patent publication no. EP 0 827 742 A1, published 11 Mar. 1998.

Gordon M., Pearson D. E., 1964, *J. Org. Chem.*, Vol. 39, p. 329.

Grozinger et al., 1999, *Proc. Natl. Acad. Sci. USA*, Vol. 96, pp. 4868-4873.

Guines, H. S., et al. (Fac. Pharm., Ede Univ., Bornova-Izmir, Turkey), 1992, "Synthesis of some hydroxamic acid derivatives of benzimidazole and their antibacterial and antifungal activities," *Arzneimittel-Forschung*, Vol. 42, No. 8, pp. 1045-1048.

Hartwig, J. F., et al., 1999, *J. Org. Chem.*, Vol. 64, p. 5575.

Hoshikawa,Y., et al., 1994, *Exp. Cell. Res.*, Vol. 214(1), pp. 189-197.

Howe, L., et al., 1999, *Crit. Rev. Eukarvot. Gene Expr.*, Vol. 9(3-4), pp. 231-243.

Iavarone et al., 1999, *Mol. Cell Biol.*, Vol. 19, No. 1, pp. 916-922.

Iwao M., Kuraishi T., 1978, *J. Heteroc. Chem.*, Vol. 15, p. 1425.

Kao et al., 2000, *Genes & Dev.*, Vol. 14, p. 55-66.

Kato, K., et al., 1996, "Preparation of aromatic hydroxamic acid compounds for preventing and treating neurodegenerative diseases," published European Patent Application No. EP 0737671.

Kepez M., 1989, *Monatsh. Chem.*, Vol. 120, pp. 127-130.

Kijima et al., 1993, *J. Biol. Chem.*, Vol. 268, pp. 22429-22435.

Kim et al., 1999, *Oncogene*, Vol. 18(15), pp. 2461-2470.

Kim et al., 2001, *Nature Medicine*, Vol. 7, No. 4, pp. 437-443.

Kim, M. S., et al., 2001 "Histone deacetylases induce angiogenesis by negative regulation of tumour suppressor genes," *Nature Medicine*, Vol 7. No. 4 pp. 437-443.

Kimura et al., 1994, *Biol. Pharm. Bull.*, Vol. 17, No. 3, pp. 399-402.

Kitamura, K., et al., 2000, *Br. J. Haematol.*, Vol. 108(4), pp. 696-702.

Kloc, K., Kubitz, E., Mlochowski J., 1984, *Heterocycles*, Vol. 22, p. 2517.

Kolar P., Petric A., Tisler M., Felluga F., 1991, *J. Heteroc. Chem.*, Vol. 28, p.1715.

Kouzarides, T., 1999, "Histone acetylases and deacetylases in cell proliferation," *Curr. Opin. Genet. Dev.*, Vol. 9, No. 1, pp. 40-48.

Kuusisto et al., 2001, *Biochem. Biophys. Res. Commun.*, Vol. 280, No. 1, pp. 223-228.

Kwon et al., 1998, *Proc. Natl. Acad. Sci. USA*; Vol. 95, pp. 3356-3361.

Laherty, C. D., et al., 1997, *Cell*, Vol. 89(3), pp. 349-356.

Lea and Tulsyan, 1995, *Anticancer Res.*, Vol. 15, pp. 879-883.

Lea et al., 1999, *Int. J. Oncol.*, Vol. 2, pp. 347-352.

Lin, R. J., etal., 1998, *Nature*, Vol. 391(6669), pp. 811-814.

Mathes S., 1957, *Chem. Ber.*, Vol. 90, p. 758.

McCaffrey et al., 1997, *Blood*, Vol. 90, No. 5, pp. 2075-2083.

Mielnicki, L. M., et al., 1999, *Exp. Cell. Res.*, Vol. 249(1), pp. 161-176.

Musser et al., 1998, "Quinolinyl benzene hydroxamic acids as anti-inflammatory/antiallergic agents," U.S. Pat. No. 4,769,461, issued 06 Sep. 1998.

Musser J. H., Kreft A. F., Bender R. H. W., Kubrak D. M., Grimes D., 1990, *J. Med. Chem.*, Vol. 33, p. 240.

Ng, H. H. and Bird, A., 2000, *Trends Biochem. Sci.*, Vol. 25(3), pp. 121-126.

Niki et al., 1999, *Hepatology*, Vol. 29, No. 3, pp. 858-867.

Nokajima et al., 1998, *Exp. Cell Res.*, Vol. 241, pp. 126-133.

Onishi et al., 1996, *Science*, Vol. 274, pp. 939-940.

Pazin, M. J., et al., 1997, "What's up and down with histone deacetylation and transcription?," *Cell*, Vol. 89, No. 3, pp. 325-328.

Phillips A. P., 1948, *J. Am. Chem. Soc.*, Vol. 70, p. 452.

Richon et al, 1996, *Proc. Natl. Acad. Sci. USA*, Vol. 93, pp. 5705-5708.

Richon et al., 1998, "A class of hybrid poler inducers of transformed cell differentiation inhibits histone deacetylases," *Proc. Natl. Acad. Sci. USA*, Vol. 95, pp. 3003-3007.

Ried, W., Keller, H., 1956, "Uber heterocyclisch substituierte Aminosaeuren, V. Mitteil: Synthesen einiger β-heterocyclisch substituierter Acryl- and β-Aminosaeuren," Chem. Ber., Vol. 89, No. 11, pp. 2578-2583.

Saito et al., 1999, *Proc. Natl. Acad. Sci. USA*, Vol. 96, pp. 4592-4597.

Saunders, N. et al, 1999 "Histone deacetylase inhibitors as potential anti-skin cancer agents," *Cancer Res.*, Vol. 59, No. 2 pp. 399-404.

Sonoda, H. et al., 1996, *Oncopene*, Vol. 13, pp. 143-149.

Spencer, V. A. and Davie, J. R., 1999, *Gene*, Vol. 240 (1), pp. 1-12.

Stefan, J., et al., 2002, "Method for treating neurodegenerative, psychiatric and other disorders with deacetylase inhibitors," published international (PCT) patent application number WO 02/090534.

Strakov, A. Ya., et al. (Rizh. Politeckh. Inst., Riga, USSR), 1972, "Hydrolytic cleavage of 3,3,6-trimethyl-2,3,4,5-tetrahydro-1H-dibenzo(b,e)-1,4-diazepin-5-one," *Latvijas PSR Zinatnu Akademijas Vestis, Kimijas Serija*, Vol. 3, pp. 355-359.

Suzuki et al., 1999, "Synthesis and histone deactylase inhibitory activity of new benzamide derivatives," *J. Med. Chem.*, Vol. 42, pp. 3001-3003.

Takahashi et al., 1996, *J. Antibiot.* (*Tokyo*), Vol. 49, No. 5, pp. 453457.

Takahashi, I., et al, 1996, "Selective inhibition of IL-2 gene expression by trichostatin A, a potent inhibitor of mammalian histone deacetylase," *J. Antibiot.* (*Tokyo*), Vol. 49, No. 5, pp. 453457.

Taunton, J., et al., 1996, "A mammalian histone deacetylase related to the yeast transcriptional regulator Rpd3p," *Science*, Vol. 272, pp. 408-411.

Tsuji et al., 1976, *J. Antibiot.* (*Tokyo*), Vol. 29, No.1, pp. 1-6.

Turin, M., et al., 1976, "Furobenzoxazolylacethydroxamic acids," French Patent Application No. 1976-1055.

Ueda, H., et al., 1994, *J. Antibiot.* (*Tokyo*), Vol. 47 (3), pp. 315-323.

Van den Wyngaert et al., 2000, *FEBS*, Vol. 478, pp. 77-83.

Venkatesan, A. M., et al., 2001, "N-Hydroxy-2-(alkyl, aryl or heteroaryl sulfanyl, sulfinyl or sulfonyl)-3-substituted alkyl, aryl or heteroaryl amides as matrix metalloprotease inhibitors," U.S. Pat. No. 6,172,057 granted 09 Jan. 2001.

Vigushin et al., 2001, *Clin. Cancer Res.*, Vol. 7, No. 4, pp. 971-976.

Warrell et al., 1998, *J. Natl. Cancer Inst.*, Vol. 90, pp. 1621-1625.

Watkins, C., et al., 2002a, "Carbamic acid compounds comprising a sulfonamide linkage as HDAC inhibitors," published international (PCT) patent application number WO 02/30879(PCT/GB01/04326) published 27 Sep. 2002.

Watkins, C., et al., 2002b, "Carbamic acid compounds comprising an ether linkage as HDAC inhibitors," published international (PCT) patent application number WO 02/26703 (PCT/GB01/04327) published 27 Sep. 2002.

Watkins, C., et al., 2002c, "Carbamic acid compounds comprising an amide linkage as HDAC inhibitors," published international (PCT) patent application number WO 02/26696 (PCT/GB01/04329) published 27 Sep. 2002.

Watkins, C., et al., 2003, "Carbamic acid compounds comprising a piperazine linkage as HDAC inhibitors," published international (PCT) patent application number WO 03/082288 (PCT/GB03/01463) published 09 Oct. 2003.

Weygand F., 1962, *Justus Liebias Ann. Chem.*, Vol. 658, p. 128.

Wong, J., et al., 1998, *EMBO J.*, Vol. 17(2), pp. 520-534.

Yang, W. M., et al., 1996, "Transcriptional repression of YY1 is mediated by interaction with a mammalian homolog of the yeast global regulator RPD3," *Proc. Natl. Acad. Sci. USA*, Vol. 93, pp. 12845-12850.

Yang, W. M., et al., 1997, "Isolation and characterization of cDNAs corresponding to an additional member of the human histone deacetylase gene family," *J. Biol. Chem.*, Vol 272, pp. 28001-28007.

Yoshida et al., 1995, *Bioessays*, Vol. 17, pp.423-430.

Yoshida, M. and Horinouchi, S., 1999, *Ann. N.Y. Acad. Sci.*, Vol. 886, pp. 23-36.

Yoshida, M., Beppu, T., 1988, "Reversible arrest of proliferation of rat 3Y1 fibroblasts in both G1 and G2 phases by trichostatin A," *Exp. Cell. Res.*, Vol. 177, pp.122-131.

Yoshida, M., et al., 1990a, *J. Biol. Chem.*, Vol. 265(28), pp. 17174-17179.

Yoshida, M., et al., 1990b, *J. Antibiot.* (*Tokyo*), Vol. 43(9), pp. 1101-1106.

The invention claimed is:

1. A compound selected from compounds of the following formula and pharmaceutically acceptable salts thereof:

$$A-Q-\underset{H}{\overset{O}{\underset{\|}{C}}}-N-OH \quad (1)$$

wherein:

A is an unsubstituted or substituted quinoline;

Q is independently a saturated or unsaturated $C_{1-7}$ alkylene group having a backbone length of 4 or less;

wherein backbone atoms of Q, which link A and —C(=O)NHOH, are denoted α, β, γ, and δ, starting with the backbone atom adjacent to —C(=O)NHOH;

wherein Q is unsubstituted or substituted with one or more substituents independently selected from —CONH$_2$,—CONMe$_2$, —C(=O)Me, —F, —Cl, —Br, —I, —NO$_2$, —OH, —OMe, —OEt, —O(iPr), —NH$_2$, —NMe$_2$, —NEt$_2$, morpholino, —NHCOMe, -Ph, =O, =NH, =NMe, and =NOH;

with the proviso that if A is unsubstituted quinolin-6-yl, then Q is unsubstituted at the α-position.

2. A compound according to claim 1, wherein A is quinolin-2-yl; quinolin-3-yl; quinolin-4-yl; quinolin-5-yl; quinolin-6-yl; or quinolin-7-yl; quinolin-8-yl; and is unsubstituted or substituted.

3. A compound according to claim 2, wherein A is: unsubstituted; or
substituted with one or more substituents independently selected from carboxylic acid; ester; amido; acyl; halo; cyano; nitro; hydroxy; ether; thiol; thioether; acyloxy; amino; acylamino; aminoacylamino; sulfonamino; sulfonyl; sulfonate; sulfonamido; $C_{5-20}$ aryl-$C_{1-7}$alkyl; $C_{5-20}$aryl; $C_{3-20}$heterocyclyl; $C_{1-7}$alkyl; oxo; imino; and hydroxyimino.

4. A compound according to claim 2, wherein A is: unsubstituted; or
substituted with one or more substituents independently selected from —C(=O)OMe, —C(=O)O(Pr), —C(=O)NHMe, —C(=O)Et, —C(=O)Ph, —F, —Cl, —NO$_2$, —OMe, —OEt, —OPh, —OCH$_2$CH$_2$OH, —O—CH$_2$-Ph, —NMe$_2$, —SO$_2$Me, —SO$_2$Me$_2$, —CH$_2$-Ph, -Ph,-PhF, -Ph- Cl, —Me, -Et, -nPr, iPr, —CF$_3$, —CH$_2$CH$_2$OH, and —CH$_2$CH$_2$NMe$_2$.

5. A compound according to claim 2, wherein A is: unsubstituted; or
substituted with one or more substituents independently selected from —F, —Cl, —OMe, —OEt, —OPh, —O—CH$_2$-Ph, —CH$_2$-Ph, -Ph —Me, and -Et.

6. A compound according to claim 2, wherein A is unsubstituted.

7. A compound according to claim 2, wherein Q is independently an unsubstituted or substituted, saturated $C_{1-7}$alkylene group; and has a backbone length of 4 or less.

8. A compound according to claim 2, wherein Q is independently an unsubstituted or substituted, unsaturated $C_{2-7}$alkylene group; and has a backbone length of 4 or less.

9. A compound according to claim 2, wherein Q is independently an unsubstituted or substituted, saturated aliphatic $C_{1-7}$alkylene group; and has a backbone length of 4 or less.

10. A compound according to claim 2, wherein Q is independently an unsubstituted or substituted, unsaturated aliphatic $C_{2-7}$alkylene group; and has a backbone length of 4 or less.

11. A compound according to claim 2, wherein Q has a backbone length of from 2 to 4 atoms.

12. A compound according to claim 2, wherein Q has a backbone length of from 2 to 3 atoms.

13. A compound according to claim 2, wherein Q has a backbone length of 2 atoms.

14. A compound according to claim 2, wherein Q is unsubstituted at the α-position.

15. A compound according to claim 2, wherein Q is unsubstituted at the α-position and the β-position.

16. A compound according to claim 2, wherein Q is unsubstituted.

17. A compound according to claim 2, wherein Q is —CH=CH—, —CH$_2$—CH$_2$—, —CH(CH$_3$)—CH$_2$—, or —CH$_2$—CH(CH$_3$)—.

18. A compound according to claim 2, wherein Q is —CH=CH— or —CH$_2$—CH$_2$—.

19. A compound according to claim 2, wherein Q is —CH=CH—.

20. A compound according to claim 2, wherein Q is —CH$_2$—CH$_2$—.

21. A pharmaceutical composition comprising a compound as defined in claim 1 and a pharmaceutically acceptable carrier.

22. A compound according to claim 2, selected from the following compounds, and pharmaceutically acceptable salts thereof:

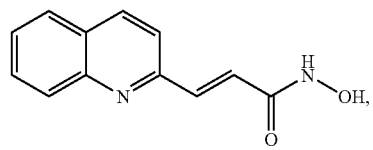

(PX117449)

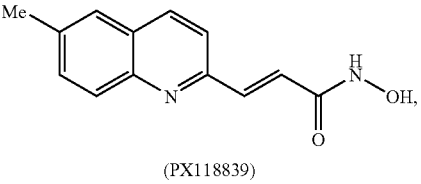

(PX118839)

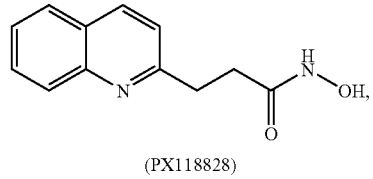

(PX118828)

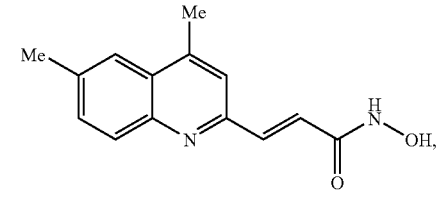

(PX118864)

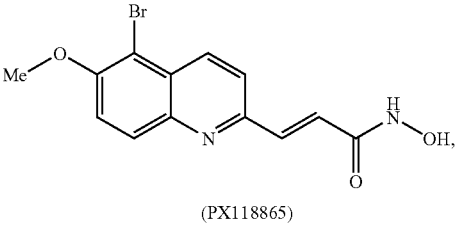

(PX118865)

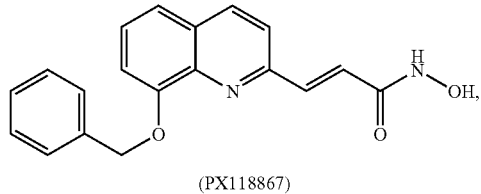

(PX118867)

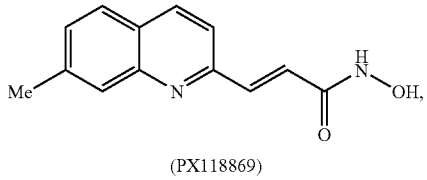

(PX118869)

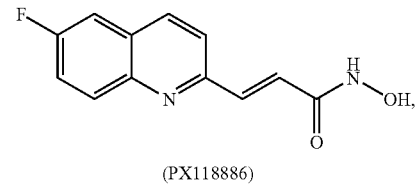

(PX118886)

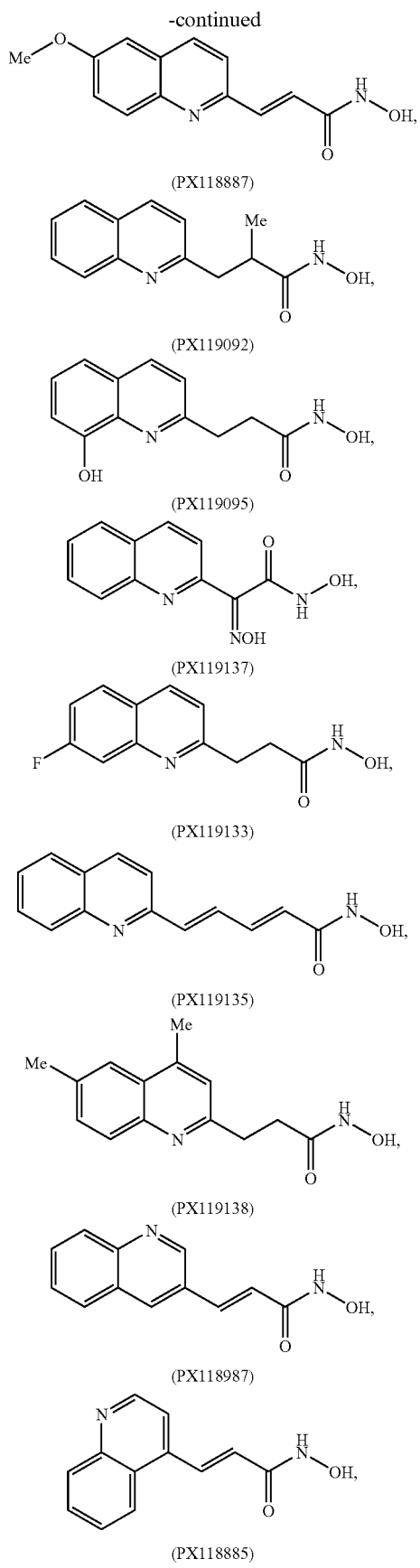
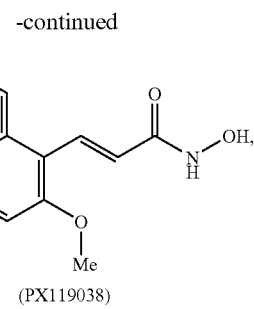

23. A pharmaceutical composition comprising a compound as defined in claim 2 and a pharmaceutically acceptable carrier.

24. A method of inhibiting HDAC in a cell comprising contacting said cell with an effective amount of a compound as defined in claim 2.

25. A method for the treatment of a proliferative condition comprising administering to a subject suffering from a proliferative condition a therapeutically-effective amount of a compound as defined in claim 2.

26. A method for the treatment of cancer comprising administering to a subject suffering from cancer a therapeutically-effective amount of a compound as defined in claim 2.

27. A method for the treatment of an inflammatory disease comprising administering to a subject suffering from an inflammatory disease a therapeutically-effective amount of a compound as defined in claim 2.

28. A compound selected from compounds of the following formula and pharmaceutically acceptable salts thereof:

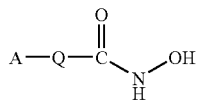

wherein:

A is independently quinolin-2-yl; quinolin-3-yl; quinolin-4-yl; quinolin-5-yl; quinolin-6-yl; quinolin-7-yl; or quinolin-8-yl; and is unsubstituted or substituted with one or more substituents independently selected from —C(=O)OMe, —C(=O)O(Pr), —C(=O)NHMe, —C(=O)Et, —C(=O)Ph, —F, —Cl, —$NO_2$, —OMe, —OEt, —OPh, —$OCH_2CH_2OH$, —O—$CH_2$-Ph, —$NMe_2$, —$SO_2Me$, —$SO_2Me_2$, —$CH_2$-Ph, -Ph, -Ph-F, -Ph-Cl, -Me, -Et, -nPr, -iPr, —$CF_3$, —$CH_2CH_2OH$, and $NH_2CH_2NMe_2$; and Q is independently —CH=CH— or —$CH_2$—$CH_2$—.

29. A compound according to claim 28, wherein A is independently quinolin-2-yl; quinolin-3-yl; quinolin-4-yl; quinolin-5-yl; quinolin-6-yl; quinolin-7-yl; or quinolin-8-yl; and is unsubstituted or substituted with one or more substituents independently selected from —F, —Cl, —OMe, —OEt, —OPh, —O—$CH_2$-Ph, —$CH_2$-Ph, -Ph, -Me, and -Et.

30. A compound according to claim 28, wherein Q is independently —CH=CH—.

31. A compound according to claim 29, wherein Q is independently —CH=CH—.

32. A compound according to claim 28, wherein Q is independently —$CH_2$—$CH_2$—.

33. A compound according to claim 29, wherein Q is independently —$CH_2$—$CH_2$—.

34. A pharmaceutical composition comprising a compound as defined in claim 28 and a pharmaceutically acceptable carrier.

35. A method inhibiting HDAC in a cell comprising contacting said cell with an effective amount of a compound as defined in claim 28.

36. A method for the treatment of a proliferative condition comprising administering to a subject suffering from a proliferative condition a therapeutically-effective amount of a compound as defined in claim 28.

37. A method for the treatment of cancer comprising administering to a subject suffering from cancer a therapeutically-effective amount of a compound as defined in claim 28.

38. A method for the treatment of an inflammatory disease comprising administering to a subject suffering from an inflammatory disease a therapeutically-effective amount of a compound as defined in claim 28.

* * * * *